(12) United States Patent
Gavai et al.

(10) Patent No.: US 9,273,075 B2
(45) Date of Patent: Mar. 1, 2016

(54) PRODRUGS OF 1,4-BENZODIAZEPINONE COMPOUNDS

(71) Applicant: BRISTOL-MYERS SQUIBB COMPANY, Princeton, NJ (US)

(72) Inventors: Ashvinikumar V. Gavai, Princeton Junction, NJ (US); Wen-Ching Han, Newtown, PA (US); Brian E. Fink, Yardley, PA (US); Victor R. Guarino, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/429,930

(22) PCT Filed: Sep. 20, 2013

(86) PCT No.: PCT/US2013/060832
§ 371 (c)(1),
(2) Date: Mar. 20, 2015

(87) PCT Pub. No.: WO2014/047391
PCT Pub. Date: Mar. 27, 2014

(65) Prior Publication Data
US 2015/0232491 A1 Aug. 20, 2015

Related U.S. Application Data

(60) Provisional application No. 61/703,906, filed on Sep. 21, 2012.

(51) Int. Cl.
| | |
|---|---|
| C07D 243/18 | (2006.01) |
| C07D 243/26 | (2006.01) |
| C07F 9/645 | (2006.01) |
| A61K 31/675 | (2006.01) |
| C07D 243/24 | (2006.01) |
| A61K 31/5513 | (2006.01) |
| C07D 401/12 | (2006.01) |
| A61K 45/06 | (2006.01) |

(52) U.S. Cl.
CPC .............. *C07F 9/645* (2013.01); *A61K 31/5513* (2013.01); *A61K 31/675* (2013.01); *A61K 45/06* (2013.01); *C07D 243/24* (2013.01); *C07D 401/12* (2013.01)

(58) Field of Classification Search
CPC .............................. C07D 243/19; C07D 243/26
See application file for complete search history.

(56) References Cited

U.S. PATENT DOCUMENTS

| | | | |
|---|---|---|---|
| 4,981,847 A | 1/1991 | Sato et al. | |
| 5,322,842 A | 6/1994 | Sato et al. | |
| 5,324,726 A | 6/1994 | Bock et al. | |
| 5,852,010 A | 12/1998 | Graham et al. | |
| 5,998,407 A | 12/1999 | Graham et al. | |
| 6,331,408 B1 | 12/2001 | Zaczek et al. | |
| 6,495,540 B2 | 12/2002 | Thompson | |
| 6,503,901 B1 | 1/2003 | Thompson et al. | |
| 6,503,902 B2 | 1/2003 | Olson et al. | |
| 6,509,333 B2 | 1/2003 | Olson | |
| 6,525,044 B2 | 2/2003 | Olson et al. | |
| 6,544,978 B2 | 4/2003 | Wu et al. | |
| 6,632,812 B2 | 10/2003 | Han et al. | |
| 6,653,303 B1 | 11/2003 | Wu et al. | |
| 6,713,476 B2 | 3/2004 | Yang et al. | |

(Continued)

FOREIGN PATENT DOCUMENTS

| | | |
|---|---|---|
| EP | 0669334 | 8/1995 |
| WO | WO 97/36879 | 10/1997 |
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047370 | 3/2014 |
| WO | WO 2014/047374 | 3/2014 |
| WO | WO 2014/047390 | 3/2014 |
| WO | WO 2014/047392 | 3/2014 |
| WO | WO 2014/047393 | 3/2014 |
| WO | WO 2014/047397 | 3/2014 |

OTHER PUBLICATIONS

U.S. Appl. No. 14/627,573, filed Feb. 20, 2015, Gavai et al.

(Continued)

*Primary Examiner* — Bruck Kifle
(74) *Attorney, Agent, or Firm* — Gary D. Greenblatt

(57) ABSTRACT

Disclosed are compounds of Formula (I) and salts thereof, wherein: a) $R_1$ is H or $CH_3$, and $R_2$ is $R_y$; or b) $R_1$ is Rx and $R_2$ is H; wherein $R_x$ and $R_y$ are disclosed herein. Also disclosed are methods of using such compounds to inhibit the Notch receptor, and pharmaceutical compositions comprising such compounds. These compounds are prodrugs of compounds that are useful in treating, preventing, or slowing the progression of diseases or disorders in a variety of therapeutic areas, such as cancer.

9 Claims, 1 Drawing Sheet

(56) References Cited

U.S. PATENT DOCUMENTS

| | | | |
|---|---|---|---|
| 6,737,038 B1 | 5/2004 | Zaczek et al. |
| 6,756,511 B2 | 6/2004 | Castro Pineiro et al. |
| 6,759,404 B2 | 7/2004 | Olson et al. |
| 6,794,381 B1 | 9/2004 | Olson et al. |
| 6,878,363 B2 | 4/2005 | Zaczek et al. |
| 6,900,199 B2 | 5/2005 | Han et al. |
| 6,958,329 B2 | 10/2005 | Olson |
| 6,960,576 B2 | 11/2005 | Olson et al. |
| 6,962,913 B2 | 11/2005 | Olson et al. |
| 6,984,626 B2 | 1/2006 | Nadin et al. |
| 7,001,901 B2 | 2/2006 | Yang |
| 7,053,081 B2 | 5/2006 | Olson et al. |
| 7,053,084 B1 | 5/2006 | Olson |
| 7,101,870 B2 | 9/2006 | Olson et al. |
| 7,105,509 B2 | 9/2006 | Castro Pineiro et al. |
| 7,112,583 B2 | 9/2006 | Olson et al. |
| 7,125,866 B1 | 10/2006 | Glick et al. |
| 7,153,491 B2 | 12/2006 | Zaczek et al. |
| 7,160,875 B2 | 1/2007 | Flohr et al. |
| 7,276,495 B2 | 10/2007 | Han et al. |
| 7,276,496 B2 | 10/2007 | Olson et al. |
| 7,304,049 B2 | 12/2007 | Olson |
| 7,304,055 B2 | 12/2007 | Olson et al. |
| 7,304,056 B2 | 12/2007 | Olson et al. |
| 7,342,008 B2 | 3/2008 | Olson et al. |
| 7,354,914 B2 | 4/2008 | Olson |
| 7,375,099 B2 | 5/2008 | Galley et al. |
| 7,390,802 B2 | 6/2008 | Han et al. |
| 7,390,896 B2 | 6/2008 | Olson et al. |
| 7,423,033 B2 | 9/2008 | Olson et al. |
| 7,456,172 B2 | 11/2008 | Olson |
| 7,456,278 B2 | 11/2008 | Olson |
| 7,498,324 B2 | 3/2009 | Han et al. |
| 7,528,249 B2 | 5/2009 | Olson et al. |
| 7,544,679 B2 | 6/2009 | Flohr et al. |
| 7,582,624 B2 | 9/2009 | Carter et al. |
| 7,655,647 B2 | 2/2010 | Han et al. |
| 7,718,795 B2 | 5/2010 | Olson |
| 8,629,136 B2 | 1/2014 | Gavai et al. |
| 8,822,454 B2 | 9/2014 | Gavai et al. |
| 8,999,918 B2 | 4/2015 | Gavai et al. |
| 2007/0185094 A1 | 8/2007 | Lattmann et al. |
| 2009/0181944 A1 | 7/2009 | Boylan et al. |
| 2014/0357805 A1 | 12/2014 | Gavai et al. |

OTHER PUBLICATIONS

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

Seiffert, D., et al., "Presenilin-1 and -2 Are Molecular Targets for gamma-Secretase Inhibitors," The Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-$N$-((S,Z)-3-methyl-4-oxo-4,5-dihydro-3$H$-benzo[$d$][1,2]diazepin-5-yl)propanamide (BMS-433796): A gamma-secretase inhibitor with with A beta lowering activity in a transgenic mouse model of Alzheimer's disease," Bioorganic & Medicinal Chemistry Letters 17 pp. 4006-4011 (2007).

Jun, H.T., et al., "Top Notch Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060832 International Search Report mailed Nov. 7, 2013.

PCT/US2013/060832 Preliminary Report on Patentability mailed Apr. 2, 2015.

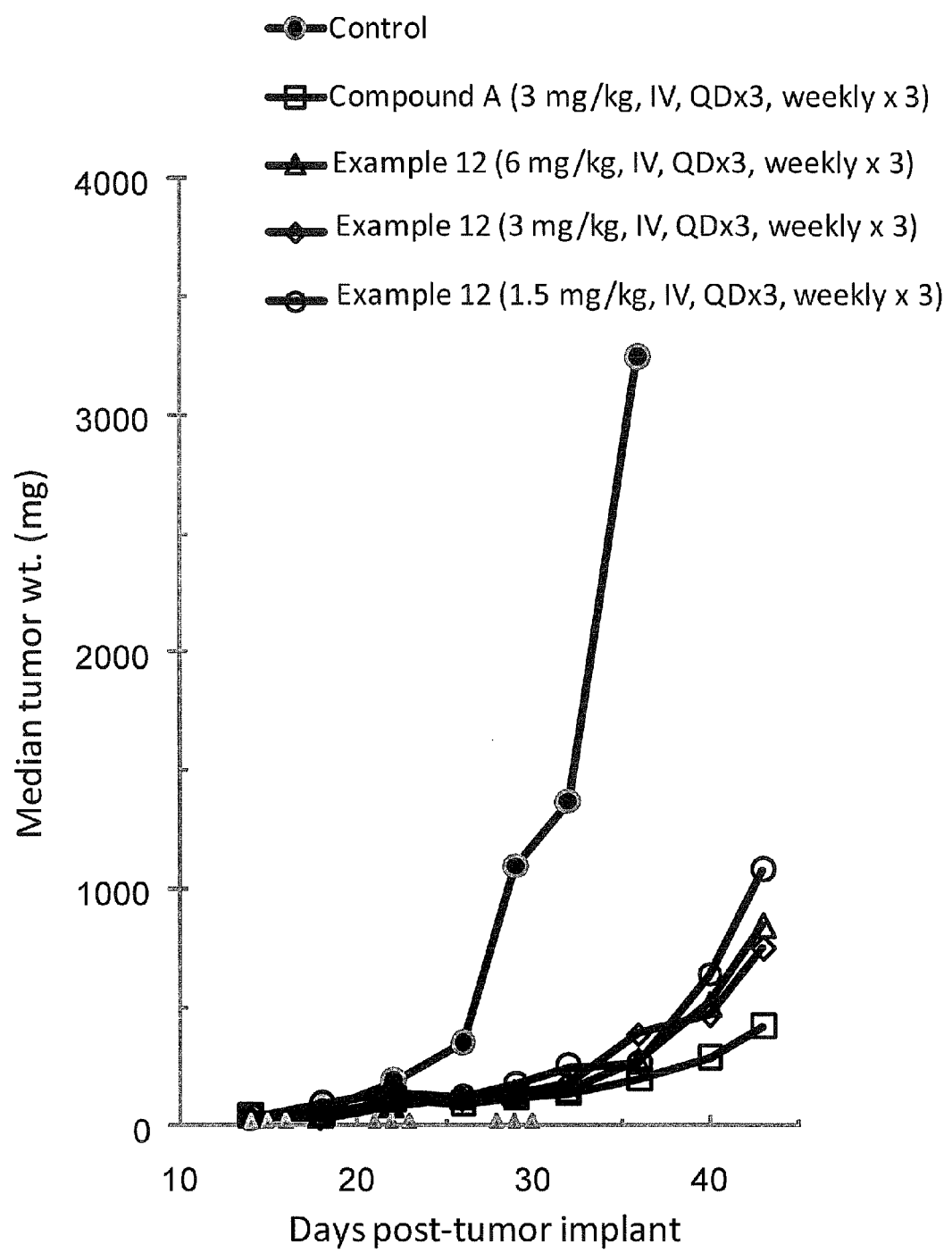

PRODRUGS OF 1,4-BENZODIAZEPINONE COMPOUNDS

CROSS REFERENCE TO RELATED APPLICATIONS

This application is a national phase application under 35 U.S.C. §371 of International Patent Application No. PCT/US2013/060832, filed Sep. 20, 2013, which claims priority to U.S. Provisional Application 61/703,906, filed Sep. 21, 2012, which are expressly incorporated fully herein by reference.

The present invention generally relates to benzodiazepinone compounds useful as prodrugs of Notch inhibitors. The invention further pertains to pharmaceutical compositions comprising at least one compound according to the invention that is useful as a prodrug of a compound for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell*, 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al. *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

The compounds (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide, having the structure of Formula (A):

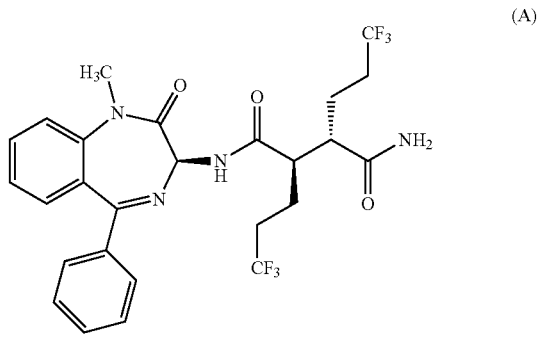 [SMILES: CN1C(=O)[C@@H](NC(=O)[C@H](CCC(F)(F)F)[C@H](CCC(F)(F)F)C(N)=O)N=C(c2ccccc2)c2ccccc21]

and (2R,3S)—N-((3S)-2-oxo-5-phenyl-2,3-dihydro-1H-1,4-benzodiazepin-3-yl)-2,3-bis(3,3,3-trifluoropropyl)succinamide, having the structure for Formula (B):

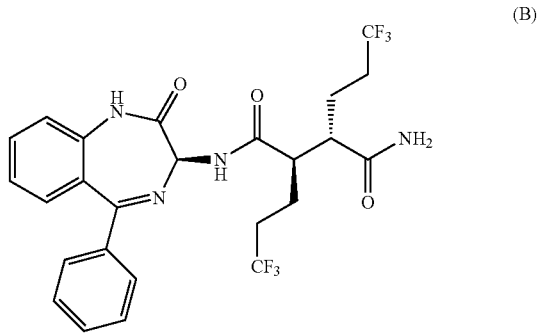 [SMILES: NC(=O)[C@@H](CCC(F)(F)F)[C@@H](CCC(F)(F)F)C(=O)N[C@H]1N=C(c2ccccc2)c2ccccc2NC1=O]

have activity as inhibitors of the Notch pathway, thus making them useful as anti-cancer agents. These compounds, preparation processes, and methods of using these compounds are disclosed in U.S. patent application Ser. No. 13/426,730. This reference is assigned to the present assignee and is incorporated herein by reference in its entirety.

As may be appreciated, there remains a need for improved delivery of Compounds (A) and (B) to the patient.

Applicants have found prodrugs of Compounds (A) and (B) useful for the administration of Compounds (A) and (B), respectively. The prodrugs have better solubility at physiological important pH values than Compounds (A) and (B), and surprisingly allow the administration of Compounds (A) and (B) with a wider dosage range and/or a broader range of pharmaceutical formulations. These prodrug compounds are provided to be useful as pharmaceuticals with desirable stability, bioavailability, therapeutic index, and toxicity values that are important to their drugability.

SUMMARY OF THE INVENTION

The present invention fills the foregoing need by providing prodrug compounds of (2R,3S)—N-((3S)-2-oxo-5-phenyl-2,3-dihydro-1H-1,4-benzodiazepin-3-yl)-2,3-bis(3,3,3-trifluoropropyl)succinamide and (2R,3S)—N-((3S)-1-methyl- 2-oxo-5-phenyl-2,3-dihydro-1H-1,4-benzodiazepin-3-yl)-2,3-bis(3,3,3-trifluoropropyl)succinamide, which are useful as selective inhibitors of Notch signaling pathway, including salts of the prodrug compounds.

The present invention also provides pharmaceutical compositions comprising a pharmaceutically acceptable carrier; and at least one compound of Formula (I), or pharmaceutically acceptable salts thereof.

The present invention also provides a method of treating a disease or disorder associated with the activity of the Notch receptor, the method comprising administering to a mammalian patient a compound of Formula (I) or pharmaceutically acceptable salts thereof.

The present invention also provides processes and intermediates for making the compounds of Formula (I) or salts thereof.

The present invention also provides the compounds of Formula (I) or pharmaceutically acceptable salts thereof, for use in therapy.

The present invention also provides the use of the compounds of Formula (I) or pharmaceutically acceptable salts thereof, for the manufacture of a medicament for the treatment of cancer.

The compounds of Formula (I) are prodrugs of Notch inhibitors, which may be used in treating, preventing or curing various Notch receptor-related conditions. Pharmaceutical compositions comprising these prodrug compounds are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawings described below.

FIG. 1 shows the antitumor efficacy of Compound A and Example 12, a prodrug of Compound A, against TALL1 Human T-cell acute lymphoblastic leukemia. Dosed intravenously QD×3, weekly×3. Each symbol represents the median tumor burden of a group of 8 mice. (•) Control; (□) Compound A, 3 mg/kg; (○) Example 12, 1.5 mg/kg; (◇) Example 12, 3 mg/kg; (Δ) Example 12, 6 mg/kg.

DETAILED DESCRIPTION

The first aspect of the present invention provides a compound of Formula (I):

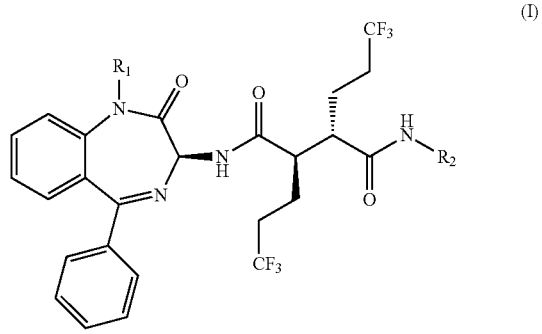

(I)

or a salt thereof, wherein:
a) $R_1$ is H or —$CH_3$, and $R_2$ is $R_y$; or
b) $R_1$ is $R_x$ and $R_2$ is H;

$R_x$ is —$CH_2OC(O)$—$(CH_2)_n$—$(CR_aR_b)_n$—X;
X is —$NR_eR_f$, —$OP(=O)(OH)_2$,

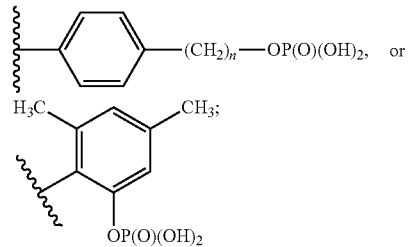

$R_a$ and $R_b$ are independently H and/or $C_{1-3}$ alkyl, or together with the carbon atom to which they are attached form a $C_{3-5}$ cycloalkyl ring;
each n is independently zero and/or 1;
$R_y$ is Z or —S—Z;
Z is $C_{1-6}$ alkyl substituted with —$NR_cR_d$ and/or —$CO_2R_g$;
$R_c$ and $R_d$ are independently H and/or $C_{1-4}$ alkyl, or together with the nitrogen to which they are attached form a heterocycle containing 1 to 2 nitrogen atoms, wherein said heterocycle is substituted with zero to 2 substituents independently selected from —OH, $C_{1-4}$ alkyl, and/or $NR_eR_f$;
$R_e$ and $R_f$ are independently H and/or $C_{1-4}$ alkyl; and
$R_g$ is H or $C_{1-4}$ alkyl.

One embodiment provides a compound of Formula (I) or a salt thereof, wherein:
a) $R_1$ is H or —$CH_3$, and $R_2$ is $R_y$; or
b) $R_1$ is $R_x$ and $R_2$ is H;
$R_x$ is: —$CH_2OC(O)C(CH_3)_2NH_2$, —$CH_2OC(O)CH(CH_3)NH_2$, —$CH_2OC(O)CH(CH(CH_3)_2)NH_2$,

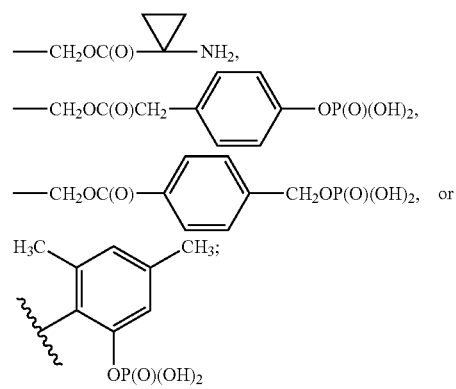

and
$R_y$ is: —$SCH_2CH_2NH_2$, —$SCH_2CH_2N(CH_3)_2$, —$SCH_2CH(NH_2)C(O)OH$, —$SCH_2CH(NH_2)C(O)OCH_3$, —$CH_2NHCH_2CH(CH_3)_2$,

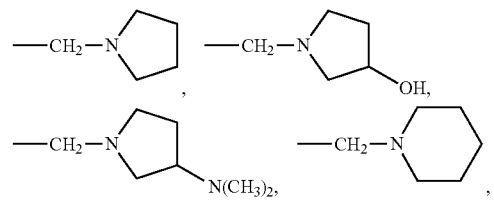

-continued

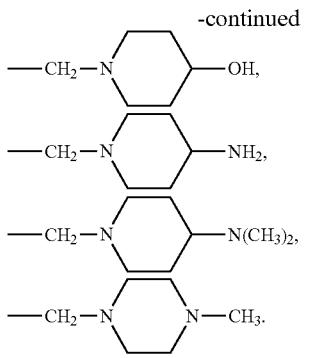

One embodiment provides a compound of Formula (I) or a salt thereof, wherein $R_1$ is H or —$CH_3$; $R_2$ is $R_y$; and $R_y$ is defined in the first aspect. This compound has the structure of Formula (II):

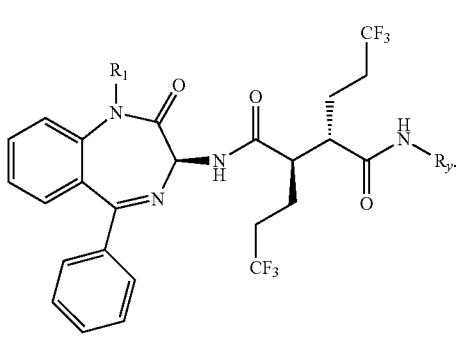

One embodiment provides a compound of Formula (II) or a salt thereof, wherein $R_y$ is Z or —S—Z; Z is $C_{1-6}$ alkyl substituted with —$NR_cR_d$ and/or —$CO_2R_g$; $R_c$ and $R_d$ are independently H and/or $C_{1-4}$ alkyl, or together with the nitrogen to which they are attached form a 5- to 6-membered heterocycle containing nitrogen heteroatom and zero to 1 additional heteroatom, wherein said heterocycle is substituted with zero to 2 substituents independently selected from —OH, $C_{1-4}$ alkyl, and/or $NR_eR_f$; and $R_e$ and $R_f$ are defined in the first aspect. Included in this embodiment are compounds in which the 5- to 6-membered heterocycle contains a nitrogen heteroatom and zero to 1 additional heteroatom selected from nitrogen or oxygen. Also included in this embodiment are compounds in which the 5- to 6-membered heterocycle is selected from pyrrolidine, piperidine, piperazine, and morpholine.

One embodiment provides a compound of Formula (II) or a salt thereof, wherein $R_1$ and $R_y$ are defined in the first aspect; and $R_c$ and $R_d$ are independently H and/or $C_{1-4}$ alkyl. Included in the embodiment are compounds in which $R_c$ and $R_d$ are independently H and/or $C_{1-2}$ alkyl. Also included in this embodiment are compounds in which $R_c$ and $R_d$ are independently H and/or —$CH_3$.

One embodiment provides a compound of Formula (II) or a salt thereof, wherein $R_1$ and $R_y$ are defined in the first aspect; and $R_c$ and $R_d$ together with the nitrogen to which they are attached form a 5- to 6-membered heterocycle containing nitrogen heteroatom and zero to 1 additional heteroatom, wherein said heterocycle is substituted with zero to 2 substituents independently selected from —OH, $C_{1-4}$ alkyl, and/or $NR_eR_f$. Included in this embodiment are compounds in which the 5- to 6-membered heterocycle contains a nitrogen heteroatom and zero to 1 additional heteroatom selected from nitrogen or oxygen. Also included in this embodiment are compounds in which the 5- to 6-membered heterocycle is selected from pyrrolidine, piperidine, piperazine, and morpholine.

One embodiment provides a compound of Formula (I) or a salt thereof, wherein $R_1$ and $R_2$ are defined in the first aspect; and $R_e$ and $R_f$ are independently H and/or $C_{1-2}$ alkyl. Included in this embodiment are compounds in which $R_e$ and $R_f$ are independently H or —$CH_3$. Also included in this embodiment are compounds in which $R_e$ is H and $R_f$ is H.

One embodiment provides a compound of Formula (II) or a salt thereof, wherein $R_1$ and $R_y$ are defined in the first aspect; and $R_g$ is H or $C_{1-2}$ alkyl. Included in this embodiment are compounds in which $R_g$ is H or —$CH_3$.

One embodiment provides a compound of Formula (I) or a salt thereof, wherein $R_1$ is H and $R_2$ is $R_y$. This compound has the structure of Formula (III):

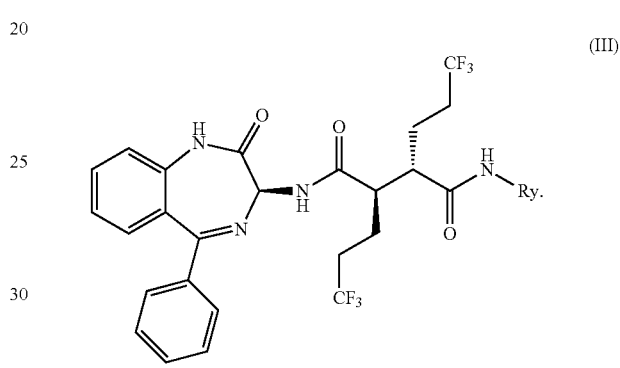

Included in this embodiment are compounds of Formula (III) or salts thereof wherein $R_y$ is —$SCH_2CH_2NH_2$ or —$SCH_2CH(NH_2)C(O)OH$.

One embodiment provides a compound of Formula (III) or a salt thereof selected from:

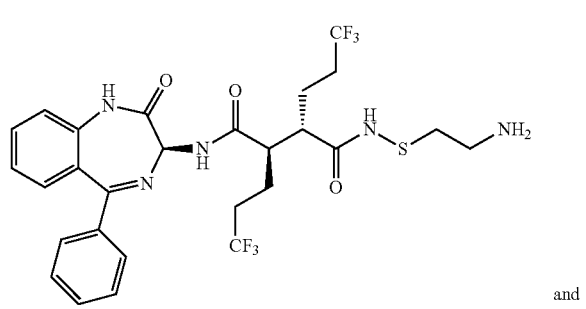

and

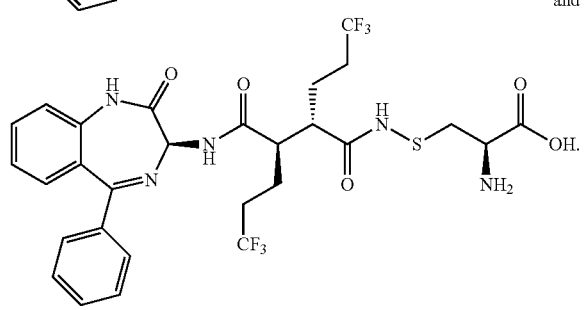

One embodiment provides a compound of Formula (I) or a salt thereof, wherein $R_1$ is —$CH_3$ and $R_2$ is $R_y$. This compound has the structure of Formula (IV):

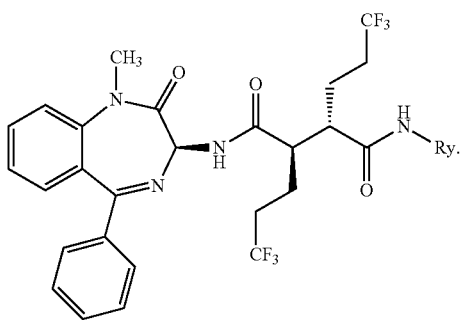

One embodiment provides a compound of Formula (IV) or a salt thereof, wherein $R_y$ is —CH$_2$NHCH$_2$CH(CH$_3$)$_2$, —SCH$_2$CH$_2$NH$_2$, —SCH$_2$CH$_2$N(CH$_3$)$_2$, —SCH$_2$CH(NH$_2$)C(O)OH, —SCH$_2$CH(NH$_2$)C(O)OCH$_3$,

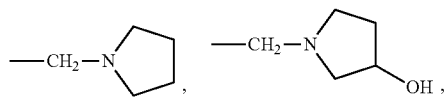

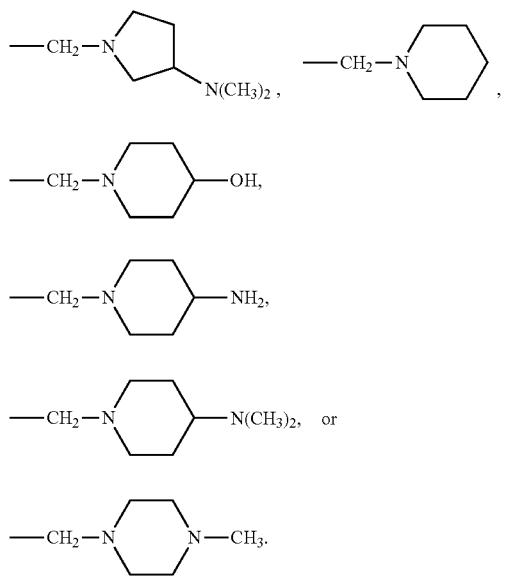

One embodiment provides a compound of Formula (III) or a salt thereof, selected from:

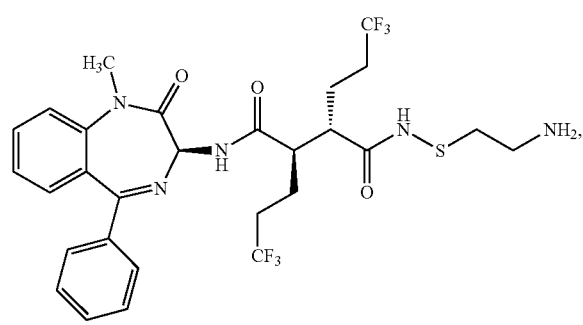

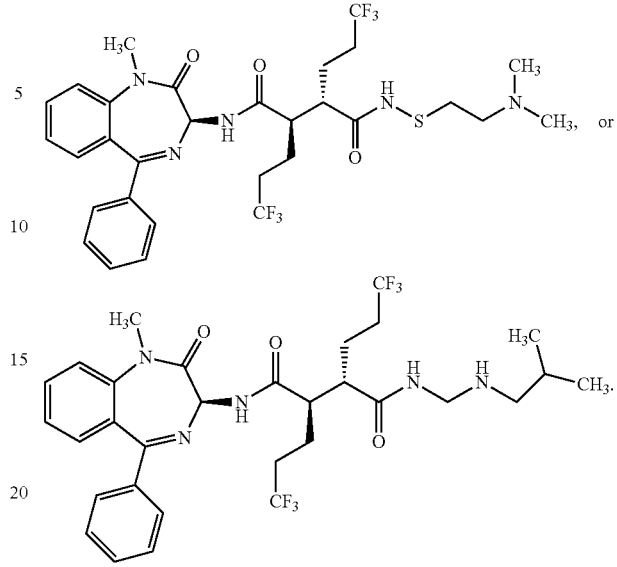

One embodiment provides a compound of Formula (III) or a salt thereof, selected from:

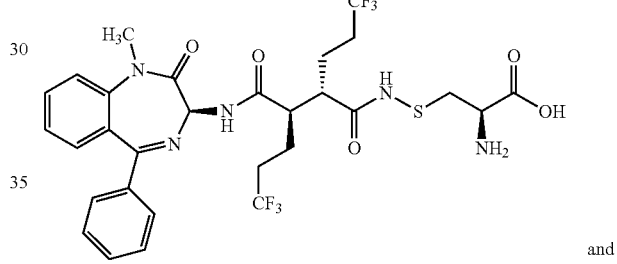

and

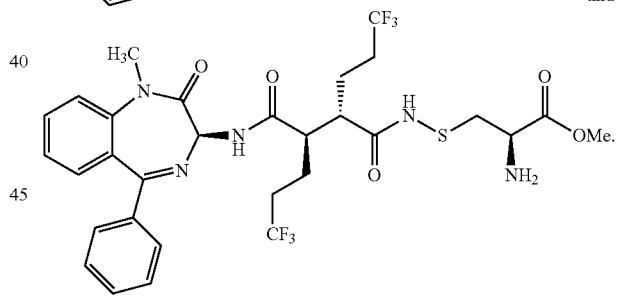

One embodiment provides a compound of Formula (III) or a salt thereof, selected from:

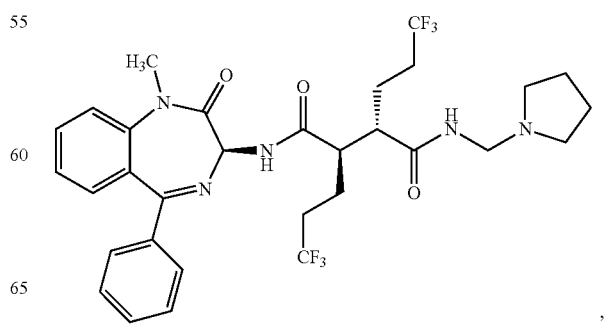

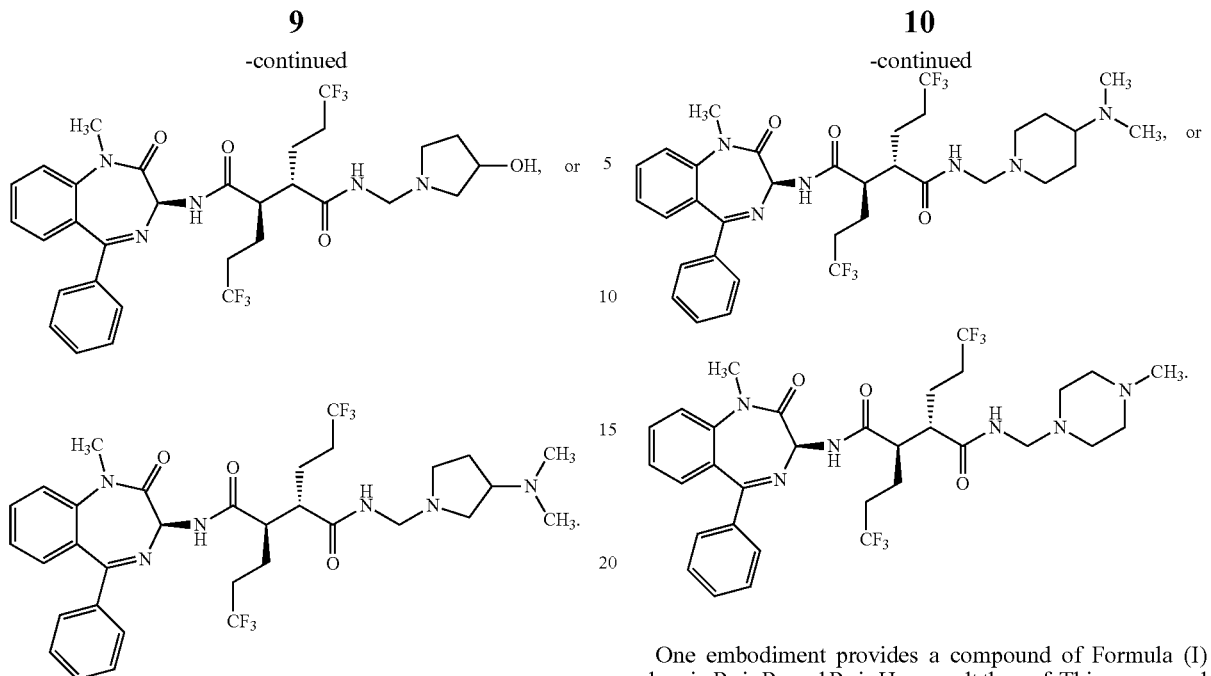

One embodiment provides a compound of Formula (III) or a salt thereof, selected from:

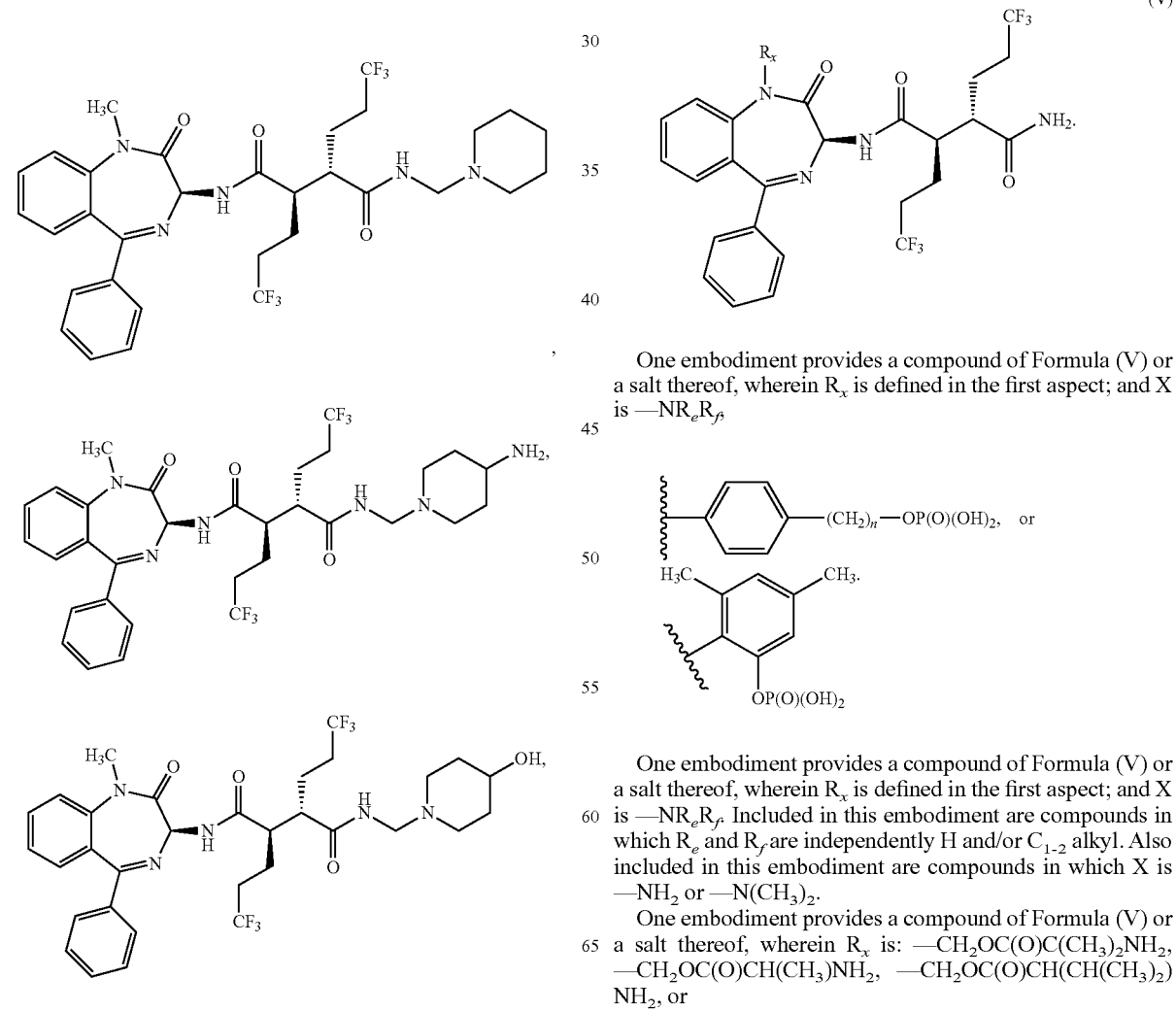

One embodiment provides a compound of Formula (I) wherein $R_1$ is $R_x$ and $R_2$ is H; or a salt thereof. This compound has the structure of Formula (V):

One embodiment provides a compound of Formula (V) or a salt thereof, wherein $R_x$ is defined in the first aspect; and X is $-NR_eR_f$.

One embodiment provides a compound of Formula (V) or a salt thereof, wherein $R_x$ is defined in the first aspect; and X is $-NR_eR_f$. Included in this embodiment are compounds in which $R_e$ and $R_f$ are independently H and/or $C_{1-2}$ alkyl. Also included in this embodiment are compounds in which X is $-NH_2$ or $-N(CH_3)_2$.

One embodiment provides a compound of Formula (V) or a salt thereof, wherein $R_x$ is: $-CH_2OC(O)C(CH_3)_2NH_2$, $-CH_2OC(O)CH(CH_3)NH_2$, $-CH_2OC(O)CH(CH(CH_3)_2)NH_2$, or

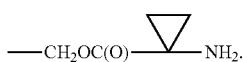

One embodiment provides a compound of Formula (V) or a salt thereof, wherein $R_x$ is defined in the first aspect; and X is:

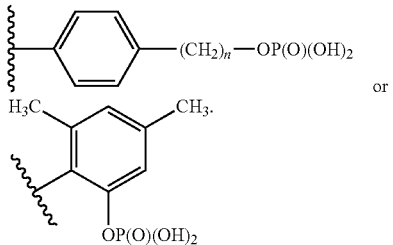

One embodiment provides a compound of Formula (V) or a salt thereof, wherein $R_x$ is:

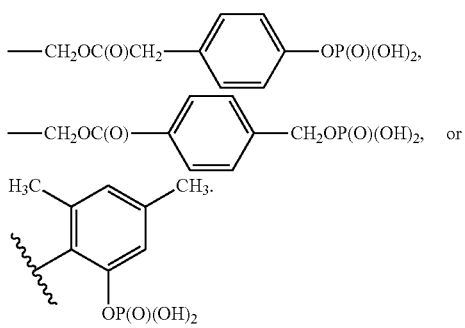

One embodiment provides at least one compound of Formula (I) and/or at least one salt thereof selected from: ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl(4-(phosphonooxy)phenyl)acetate (1); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 4-((phosphonooxy)methyl)benzoate (2); (3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 3-(2,4-dimethyl-6-(phosphonooxy)phenyl)-3-methylbutanoate (3); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 2-methylalaninate (4); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl L-alaninate (5); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl L-valinate (6); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 1-aminocyclopropanecarboxylate (7); (2S,3R)—N-((2-aminoethyl)sulfanyl)-N'-((3S)-2-oxo-5-phenyl-2,3-dihydro-1H-1,4-benzodiazepin-3-yl)-2,3-bis(3,3,3-trifluoropropyl)succinamide (8); S-(((2S,3R)-6,6,6-trifluoro-3-(((3S)-2-oxo-5-phenyl-2,3-dihydro-1H-1,4-benzodiazepin-3-yl)carbamoyl)-2-(3,3,3-trifluoropropyl)hexanoyl)amino)-L-cysteine (9); (2S,3R)—N-((isobutylamino)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (10); (2S,3R)—N-((2-aminoethyl)sulfanyl)-N'-((3S)-1-methyl-2-oxo-5-phenyl-2,3-dihydro-1H-1,4-benzodiazepin-3-yl)-2,3-bis(3,3,3-trifluoropropyl)succinamide (11); S-(((2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoyl)amino)-L-cysteine (12); (2S,3R)—N-((2-(dimethylamino)ethyl)sulfanyl)-N'-((3S)-1-methyl-2-oxo-5-phenyl-2,3-dihydro-1H-1,4-benzodiazepin-3-yl)-2,3-bis(3,3,3-trifluoropropyl)succinamide (13); Methyl S-(((2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoyl)amino)-L-cysteinate (14); (2R,3S)—N-((3S)-1-methyl-2-oxo-5-phenyl-2,3-dihydro-1H-1,4-benzodiazepin-3-yl)-N-((4-methyl-1-piperazinyl)methyl)-2,3-bis(3,3,3-trifluoropropyl)succinamide (15); (2R,3S)—N-((3S)-1-methyl-2-oxo-5-phenyl-2,3-dihydro-1H-1,4-benzodiazepin-3-yl)-N'-(1-piperidinylmethyl)-2,3-bis(3,3,3-trifluoropropyl)succinamide (16); (2S,3R)—N-((4-amino-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (17); (2S,3R)—N-((4-(dimethylamino)-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (18); (2S,3R)—N-((4-hydroxy-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (19); (2S,3R)—N-((3-hydroxy-1-pyrrolidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (20); (2S,3R)—N-((3-(dimethylamino)-1-pyrrolidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (21); and (2R,3S)—N-((3S)-1-methyl-2-oxo-5-phenyl-2,3-dihydro-1H-1,4-benzodiazepin-3-yl)-N'-(1-pyrrolidinylmethyl)-2,3-bis(3,3,3-trifluoropropyl)succinamide (22).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 6 carbon atoms, from 1 to 4 carbon atoms, and from 1 to 2 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

The term "cycloalkyl" refers to a fully saturated hydrocarbon group containing from 1 ring and 3 to 6 carbons per ring. The term "$C_{3-6}$ cycloalkyl" is intended to include $C_3$, $C_4$, $C_5$, and $C_6$ cycloalkyl groups. Exemplary cycloalkyl groups include, but are not limited to, cyclopropyl, cyclobutyl, cyclopentyl, and cyclohexyl. Branched cycloalkyl groups such as 1-methylcyclopropyl and 2-methylcyclopropyl are included in the definition of "cycloalkyl".

The term "heterocyclo" or "heterocyclyl" may be used interchangeably and refer to non-aromatic 3- to 7-membered monocyclic groups, in which at least one of the rings has at least one heteroatom (O, S or N), said heteroatom containing ring preferably having 1 to 3 heteroatoms independently selected from O, S, and/or N. The nitrogen atoms may optionally be quaternized.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

A prodrug is a compound that can be converted in vivo to provide a bioactive agent.

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a Notch receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of Formula (I) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s)" may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising the compound of Formula (I) or salt thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I), or a salt thereof, and optionally an additional agent selected from any pharmaceutically acceptable carrier, adjuvant, and vehicle. Alternate compositions of this invention comprise a compound of the Formula (I) described herein, or a salt thereof, and a pharmaceutically acceptable carrier, adjuvant, or vehicle.

Utility

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I) or a salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a salt thereof, wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a salt thereof, wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a salt thereof, wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a salt thereof, wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a salt thereof, wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a salt thereof, wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of a compound of Formula (I) or a salt thereof, in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment provides a compound of Formula (I) or a salt thereof, for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient a compound of Formula (I) or a salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof a compound of Formula (I) or a salt thereof; and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of a compound of Formula (I) or salt thereof in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof a compound of Formula (I) or a salt thereof; administering dasatinib; and optionally, one or more additional anticancer agents.

In one embodiment, a method is provided for treating cancer comprising administering to a mammal in need thereof a compound of Formula (I) or a salt thereof; administering paclitaxel; and optionally, one or more additional anticancer agents.

In one embodiment, a method is provided for treating cancer comprising administering to a mammal in need thereof a compound of Formula (I) or a salt thereof; administering tamoxifen; and optionally, one or more additional anticancer agents.

In one embodiment, a method is provided for treating cancer comprising administering to a mammal in need thereof a compound of Formula (I) or a salt thereof; administering a glucocorticoid; and optionally, one or more additional anticancer agents. An example of a suitable glucocorticoid is dexamethasone.

In one embodiment, a method is provided for treating cancer comprising administering to a mammal in need thereof a compound of Formula (I) or a salt thereof; administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising a compound of Formula (I) or salt thereof; one or more additional agents selected from a kinase inhibitory agent (small molecule, polypeptide, and antibody), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the compound of Formula (I) is administered continuously to a patient in need thereof, one or more times daily. For example, a therapeutically effective amount of the compound of Formula (I) is administered to a patient in need thereof, one or more times daily for continuous days.

In one embodiment, the compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, the compound of Formula (I) is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) and/or at least one salt thereof is administered on one day, followed by 6 days of rest, and repeated on a weekly schedule.

In one embodiment, at least one compound of Formula (I) and/or at least one salt thereof is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) and/or at least one salt thereof is administered on two consecutive days, followed by 5 days of rest, and repeated on a weekly schedule.

In one embodiment, at least one compound of Formula (I) and/or at least one salt thereof is administered on three consecutive days followed by four days of rest, and repeated on a weekly schedule.

In one embodiment, at least one compound of Formula (I) and/or at least one salt thereof is administered on one day, followed by 10 to 13 days of rest.

In one embodiment, at least one compound of Formula (I) and/or at least one salt thereof is administered once each day (QD). This embodiment include once daily oral administration.

In one embodiment, at least one compound of Formula (I) and/or at least one salt thereof is administered twice each day (BID). This embodiment include twice daily oral administration.

In one embodiment, at least one compound of Formula (I) and/or at least one salt thereof is administered on alternate days: one day on followed by one day of rest. This two day cycle can be repeated one or more times.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 8 (Guarino, V. R. et al., *Prodrugs: Challenges and Rewards*, Stella, V. J. et al. eds., Springer: New York (2007), Part 2, pp 133-187 and references cited therein).

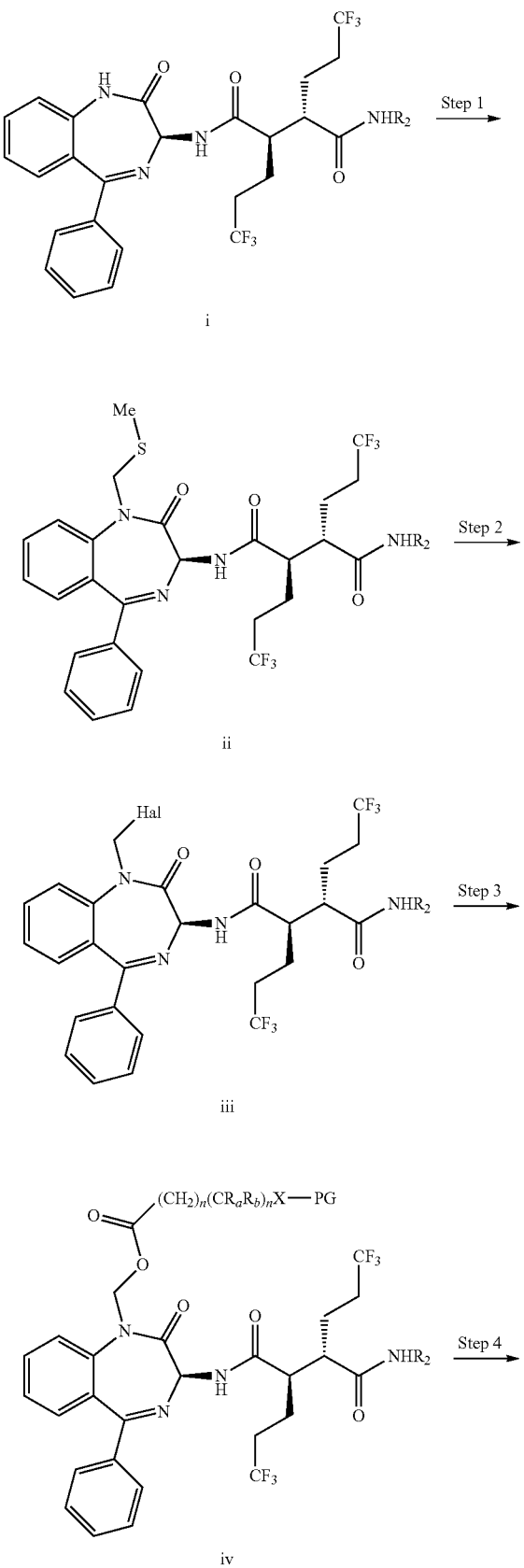

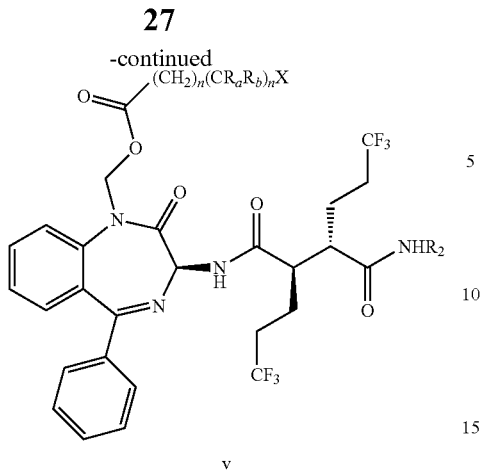

v

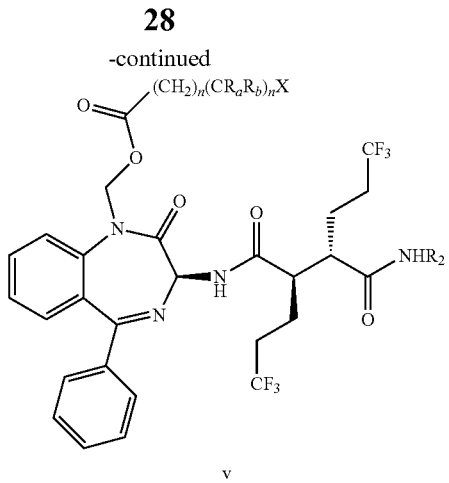

v

Step 1: Various methods known in the art may be employed to prepare compounds v. For example, as shown in Scheme 1, an appropriately substituted benzodiazepine (i) may be treated with a haloalkyl thioether such as (chloromethyl)(methyl)sulfane in the presence of a base, such as cesium carbonate in an appropriate solvent such as N,N-dimethylformamide (DMF) to afford compounds of formula ii.

Step 2: Treatment of compound ii with a reagent such as sulfuryl chloride in the presence of an amine salt, such as triethylammonium chloride in an aprotic solvent such as dichloromethane (DCM) may be used to effect the transformation to compounds of formula iii (Hal=chlorine).

Step 3: Compounds of formula iv may be prepared from compound iii by treatment with an appropriately substituted carboxylic acid or carboxylate salt in the presence of a base (when starting from a carboxylic acid) such as potassium carbonate in an aprotic solvent such as acetonitrile or DMF.

Step 4: The deprotection of compound iv may be accomplished in several ways known to one skilled in the art. For example, where PG=tBu or Boc, compound iv may be treated with a reagent such as trifluoroacetic acid in a solvent such as DCM to afford compound v.

An additional method to prepare compound v is shown in Scheme 2.

Step 1: An appropriately functionalized carboxylic acid (PG-X-(CR$_a$R$_b$)$_n$(CH$_2$)—CO$_2$H) or carboxylate salt (vi) may be treated with an alkylating agent, such as chloromethyl chlorosulfate, in the presence of a base, such as Na$_2$CO$_3$, and a quaternary ammonium salt, such as tetrabutyl ammonium sulfate in a biphasic mixture of water and an appropriate organic solvent, such as DCM at low temperature, such as 0° C., to afford compound vi.

Step 2: Treatment of compound vi with compound i in an appropriate solvent, such as DCM, in the presence of a base, such as K$_2$CO$_3$ affords compound iv.

Step 3: The deprotection of compound iv may be accomplished in several ways known to one skilled in the art. For example, where PG=tBu or Boc, compound iv may be treated with a reagent such as trifluoroacetic acid in a solvent such as DCM to afford compound v.

The preparation of sulfenamide-based prodrugs of the parent compound i is shown in Scheme 3.

Scheme 2

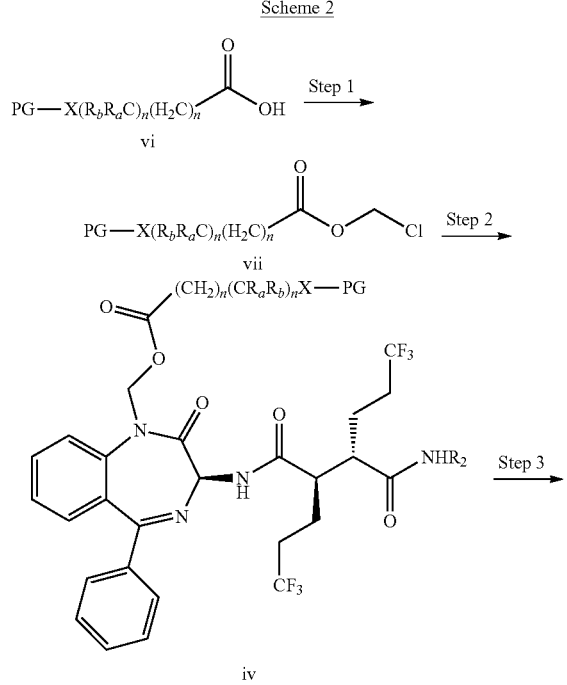

Scheme 3

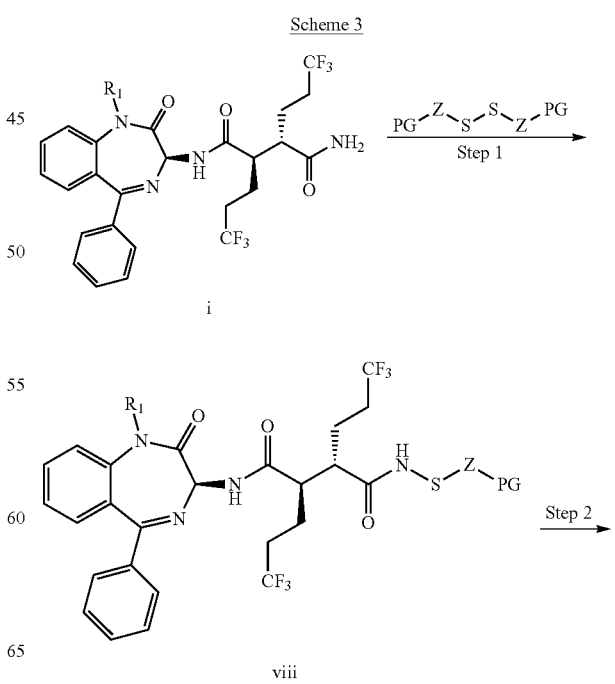

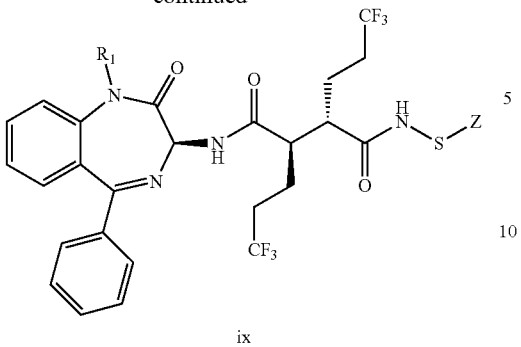

ix

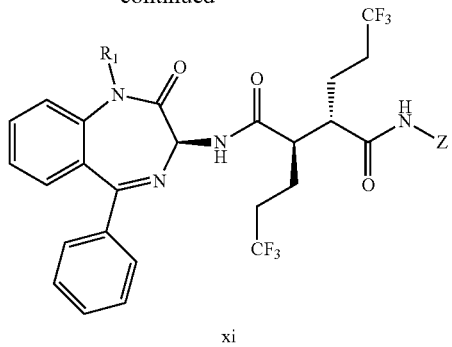

xi

Step 1: A mixture of a silver salt, such as silver nitrate, and a disulfide, such as tert-butyl 2,2'-disulfanediylbis(ethane-2,1-diyl)dicarbamate in an alcoholic solvent, such as MeOH may be treated with compound i in the presence of a base, such as triethylamine, to afford compound viii.

Step 2: The deprotection of compound viii may be accomplished in several ways known to one skilled in the art. For example, where PG=tBu or Boc, compound viii may be treated with a reagent such as trifluoroacetic acid in a solvent such as DCM to afford compound ix.

Mannich-base type pro-drugs of compound xi may be prepared by methods known to one skilled in the art (Scheme 4).

Scheme 4

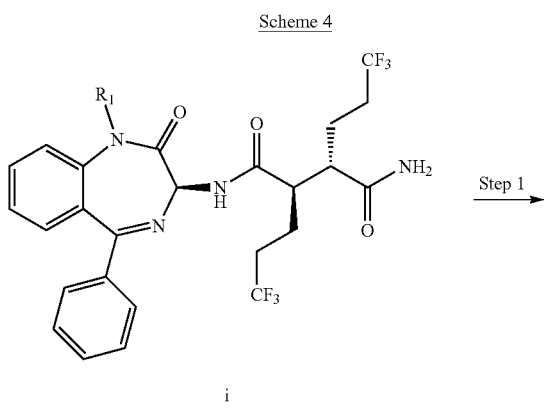

i

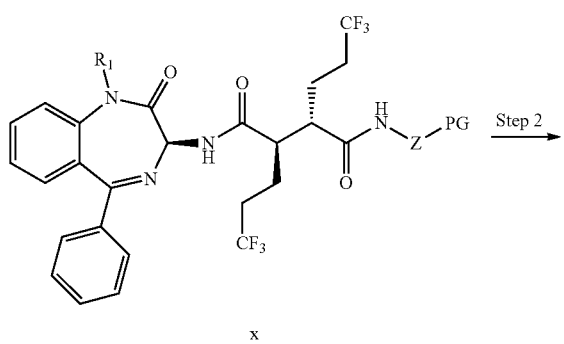

x

Step 1: For example, compound i may be reacted with formaldehyde, an amine, such as pyrrolidine, in an appropriate solvent, such as MeOH to afford compound x.

Step 2: The deprotection of compound x may be accomplished in several ways known to one skilled in the art. For example, where PG=tBu or Boc, compound x may be treated with a reagent such as trifluoroacetic acid in a solvent such as DCM or anhydrous HCl in a solvent such as diethyl ether to afford compound xi.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

ACN acetonitrile
Bn benzyl
Boc tert-butoxycarbonyl
Boc$_2$O di-tert-butyl dicarbonate
CBz benzyloxycarbonyl
DCM dichloromethane
DEA diethylamine
dil. dilute
DMF dimethylformamide
DMSO dimethyl sulfoxide
EDCI 1-(3-dimethylaminopropyl)-3-ethylcarbodiimide hydrochloride
EtOH ethanol
EtOAc ethyl acetate
equiv. equivalence
g gram
h or hr hour(s)
HOBt hydroxybenzotriazole
HPLC high pressure liquid chromatography
IPA isopropyl alcohol
LCMS Liquid Chromatography-Mass Spectroscopy
LDA lithium diisopropylamide
LAH lithium aluminum hydride
MeOH methanol
min minute(s)
mL milliliter
mmol millimolar n-BuLi n-butyl lithium
NaHMDS sodium bis(trimethylsilyl)amide
NH$_4$OAc ammonium acetate
RT retention time
t-Bu tertiary butyl
TBTU O-(1H-benzotriazol-1-yl)-N,N,N',N'-tetramethyluronium tetrafluoroborate
TEA triethylamine
TFA trifluoroacetic acid
Tf$_2$O trifluoromethylsulfonic anhydride
THF tetrahydrofuran
TLC thin layer chromatography
μL microliter Compound A (2R,3S)—N-((3S)-1-Methyl-2-oxo-5-phenyl-2,3-dihydro-1H-1,4-benzodiazepin-3-yl)-2,3-bis(3,3,3-trifluoropropyl)succinamide

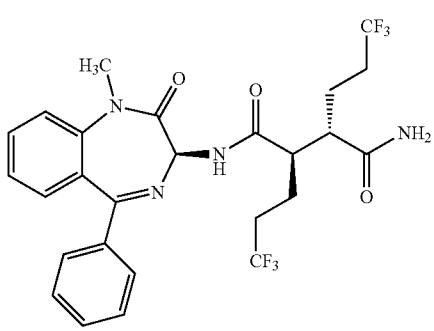

(A)

Preparation A-1A: tert-Butyl 5,5,5-trifluoropentanoate

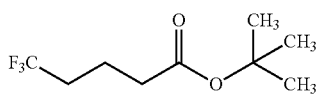

(A-1A)

To a stirred solution of 5,5,5-trifluoropentanoic acid (5 g, 32.0 mmol) in THF (30 mL) and hexane (30 mL) at 0° C., was added tert-butyl 2,2,2-trichloroacetimidate (11.46 mL, 64.1 mmol). The mixture was stirred for 15 min at 0° C. Boron trifluoride etherate (0.406 mL, 3.20 mmol) was added and the reaction mixture was allowed to warm to room temperature overnight. To the clear reaction mixture was added solid NaHCO$_3$ (5 g) and it was stirred for 30 min. The mixture was then filtered through MgSO$_4$ and washed with hexanes (200 mL). The solution was allowed to rest for 45 min, and the resulting solid material was removed by filtering through the same MgSO$_4$ filter again. The filter cake was washed with hexanes (100 mL) and the filtrate was concentrated under reduced pressure without heat. The volume was reduced to about 30 mL, and the mixture was filtered through a clean fritted funnel, washed with hexane (5 mL), and then concentrated under reduced pressure without heat. The resulting neat oil was filtered through a 0.45 μm nylon membrane filter disk to provide Preparation A-1A (6.6 g, 31.4 mmol 98% yield) as a colorless oil: $^1$H NMR (400 MHz, CDCl$_3$) δ ppm 1.38 (s, 9H) 1.74-1.83 (m, 2H) 2.00-2.13 (m, 2H) 2.24 (t, J=7.28 Hz, 2H).

Preparation A-1B: (4S)-4-(Propan-2-yl)-3-(5,5,5-trifluoropentanoyl)-1,3-oxazolidin-2-one

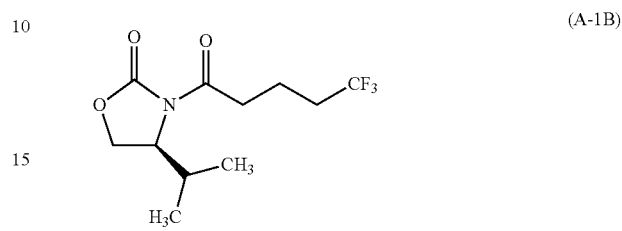

(A-1B)

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min and the solution was stirred until all bubbling subsided. The reaction mixture was concentrated under reduced pressure to give pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (2.5M in hexane) (13.0 mL, 32.5 mmol) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH$_4$Cl, and the mixture was then extracted with EtOAc (2×). The combined organics were washed with brine, dried (Na$_2$SO$_4$), filtered and concentrated under reduced pressure. The crude material was purified by flash chromatography (Teledyne ISCO CombiFlash Rf, 5% to 60% solvent A/B=hexanes/EtOAc, REDISEP® SiO$_2$ 120 g). Concentration of appropriate fractions provided Preparation A-1B (7.39 g, 86%) as a colorless oil: $^1$H NMR (400 MHz, CDCl$_3$) δ ppm 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Preparation A-1C: (2S,3R)-tert-Butyl 6,6,6-trifluoro-3-((S)-4-isopropyl-2-oxooxazolidine-3-carbonyl)-2-(3,3,3-trifluoropropyl)hexanoate, and Preparation A-1D: (2R,3R)-tert-Butyl 6,6,6-trifluoro-3-((S)-4-isopropyl-2-oxooxazolidine-3-carbonyl)-2-(3,3,3-trifluoropropyl)hexanoate

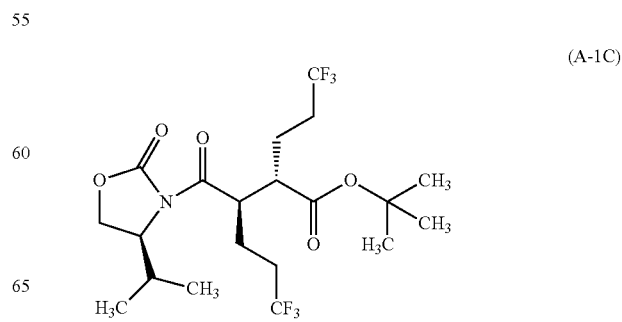

(A-1C)

33
-continued (A-1D)

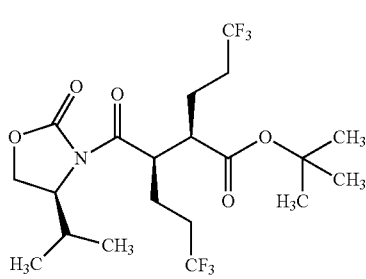

To a cold (−78° C.), stirred solution of diisopropylamine (5.3 mL, 37.2 mmol) in THF (59 mL) under a nitrogen atmosphere was added n-BuLi (2.5M in hexane) (14.7 mL, 36.8 mmol), and then the mixture was warmed to 0° C. to give a 0.5M solution of LDA. A separate vessel was charged with Preparation A-1B (2.45 g, 9.17 mmol), the material was azeotroped twice with benzene (the RotoVap air inlet was fitted with nitrogen inlet to completely exclude humidity), and then toluene (15.3 mL) was added. This solution was added to a flask containing dry lithium chloride (1.96 g, 46.2 mmol). To the resultant mixture, cooled to −78° C., was added the above LDA solution (21.0 mL, 10.5 mmol) and the mixture was stirred at −78° C. for 10 min, warmed to 0° C. for 10 min and then cooled to −78° C. To a separate reaction vessel containing Preparation A-1A (3.41 g, 16.07 mmol), also azeotroped twice with benzene, was added toluene (15.3 mL). The mixture was cooled to −78° C. and LDA (37.0 mL, 18.5 mmol) was added, and the resulting solution was stirred at −78° C. for 25 min. At this time, the enolate derived from the ester was transferred via cannula into the solution of the oxazolidinone enolate and stirred at −78° C. for an additional 5 min. The septum was removed and solid powdered bis(2-ethylhexanoyloxy)copper (9.02 g, 25.8 mmol) was rapidly added to the reaction vessel and the septum replaced. The vessel was immediately removed from the cold bath and immersed into a warm water bath (40° C.) with rapid swirling with a concomitant color change from the initial turquoise to brown. The reaction mixture was stirred for 20 min, was poured into 5% aqueous NH$_4$OH (360 mL) and extracted with EtOAc (2×). The combined organics were washed with brine, dried (Na$_2$SO$_4$), filtered and concentrated under reduced pressure. The residue was purified by flash chromatography (Teledyne ISCO CombiFlash Rf, 0% to 60% solvent A/B=hexanes/EtOAc, REDISEP® SiO$_2$ 120 g). Concentration of appropriate fractions provided Preparation A-1C (2.87 g, 66%) as a pale yellow viscous oil. $^1$H NMR showed the product was a 1.6:1 mixture of diastereoisomers 1C:1D as determined by the integration of the multiplets at 2.74 and 2.84 ppm: $^1$H NMR (400 MHz, CDCl$_3$) δ ppm 4.43-4.54 (2H, m), 4.23-4.35 (5H, m), 4.01 (1H, ddd, J=9.54, 6.27, 3.51 Hz), 2.84 (1H, ddd, J=9.41, 7.28, 3.64 Hz), 2.74 (1H, ddd, J=10.29, 6.27, 4.02 Hz), 2.37-2.48 (2H, m, J=10.38, 6.98, 6.98, 3.51, 3.51 Hz), 2.20-2.37 (3H, m), 1.92-2.20 (8H, m), 1.64-1.91 (5H, m), 1.47 (18H, s), 0.88-0.98 (12H, m).

34

Preparation A-1E: (2R,3S)-3-(tert-Butoxycarbonyl)-6,6,6-trifluoro-2-(3,3,3-trifluoropropyl)hexanoic acid, and Preparation A-1F: (2R,3R)-3-(tert-Butoxycarbonyl)-6,6,6-trifluoro-2-(3,3,3-trifluoropropyl)hexanoic acid (A-1E)

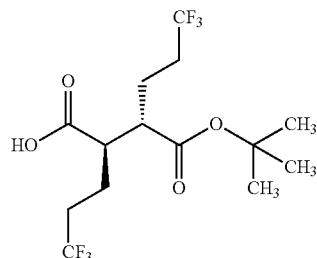

(A-1F)

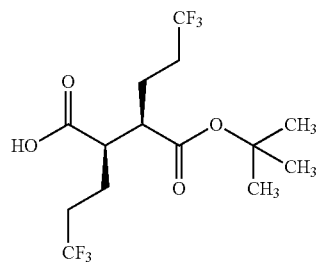

To a cool (0° C.), stirred solution of Preparation A-1C and 1D (4.54 g, 9.51 mmol) in THF (140 mL) and water (42 mL) was sequentially added hydrogen peroxide (30% in water) (10.3 g, 91 mmol) and LiOH (685.3 mg, 28.6 mmol) and the mixture was stirred for 1 hr. At this time the reaction vessel was removed from the cold bath and then stirred for 1.5 hr. To the reaction mixture was added saturated NaHCO$_3$ (45 mL) and saturated Na$_2$SO$_3$ (15 mL), and then partially concentrated under reduced pressure. The resulting crude solution was extracted with DCM (3×). The aqueous phase was acidified to pH-1-2 with 1N HCl, and then extracted with DCM (3×) and EtOAc (1×). The combined organics were washed with brine, dried (Na$_2$SO$_4$), filtered and concentrated under reduced pressure to provide a mixture of Preparation A-1E and 1F (3.00 g, 86%) as colorless oil: $^1$H NMR (400 MHz, CDCl$_3$) δ ppm 2.76-2.84 (1H, m, diastereoisomer 2), 2.64-2.76 (3H, m), 2.04-2.35 (8H, m), 1.88-2.00 (4H, m), 1.71-1.83 (4H, m), 1.48 (9H, s, diastereoisomer 1), 1.46 (9H, s, diastereoisomer 2); $^1$H NMR showed a 1.7:1 mixture of A-1E:A-1F by integration of the peaks for the t-butyl groups.

Preparation A-1E: (2R,3S)-3-(tert-Butoxycarbonyl)-6,6,6-trifluoro-2-(3,3,3-trifluoropropyl)hexanoic acid, and Preparation A-1F: (2R,3R)-3-(tert-Butoxycarbonyl)-6,6,6-trifluoro-2-(3,3,3-trifluoropropyl)hexanoic acid (A-1E)

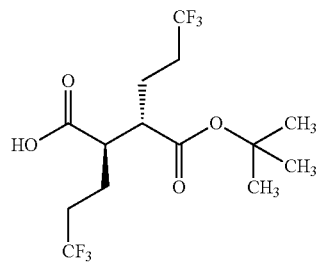

(A-1F)

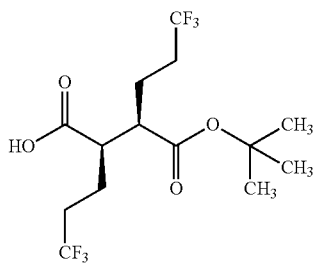

To a cold (−78° C.), stirred solution of diisopropylamine (1.7 mL, 11.93 mmol) in THF (19 mL) under a nitrogen atmosphere was added n-BuLi (2.5M in hexanes) (4.8 mL, 12.00 mmol). The mixture was stirred for 5 min and then warmed to 0° C. In a separate vessel, to a cold (−78° C.) stirred solution of the mixture of Preparation A-1E and 1F (1.99 g, 5.43 mmol) in THF (18 mL) was added the LDA solution prepared above via cannula slowly over 25 min. The mixture was stirred for 15 min, then warmed to room temperature (placed in a 24° C. water bath) for 15 min, and then again cooled to −78° C. for 15 min. To the reaction mixture was added $Et_2AlCl$ (1M in hexane) (11.4 mL, 11.40 mmol) via syringe. The resulting mixture was stirred for 10 min, warmed to room temperature for 15 min and then cooled back to −78° C. for 15 min. Methanol (25 mL) was rapidly added, and the mixture was swirled vigorously while warming to room temperature. The resulting mixture was then concentrated to ~¼ original volume. The mixture was dissolved in EtOAc and washed with 1N HCl (50 mL) and ice (75 g). The aqueous phase was separated and extracted with EtOAc (2×). The combined organics were washed with a mixture of KF (2.85 g in 75 mL water) and 1N HCl (13 mL) [resulting solution pH 3-4], then with brine, then dried ($Na_2SO_4$), filtered and concentrated under reduced pressure to give a 9:1 (A-1E:A-1F) enriched diastereoisomeric mixture (as determined by $^1$H NMR) of Preparation A-1E and Preparation A-1F (2.13 g, >99%) as a pale yellow viscous oil: $^1$H NMR (400 MHz, $CDCl_3$) δ ppm 2.64-2.76 (2H, m), 2.04-2.35 (4H, m), 1.88-2.00 (2H, m), 1.71-1.83 (2H, m), 1.48 (9H, s).

Preparation A-1G: (3S)-3-Amino-1-methyl-5-phenyl-1,3-dihydro-2H-1,4-benzodiazepin-2-one, and Preparation A-1H: (3R)-3-Amino-1-methyl-5-phenyl-1,3-dihydro-2H-1,4-benzodiazepin-2-one (A-1G)

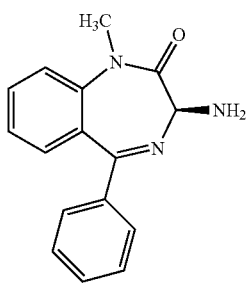

(A-1H)

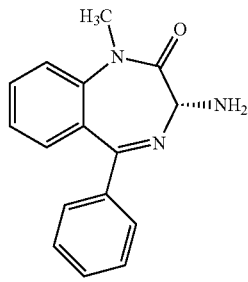

Racemic 3-amino-1-methyl-5-phenyl-1,3-dihydro-2H-1,4-benzodiazepin-2-one (Rittle, K. E. et al., *Tetrahedron Letters*, 28(5):521-522 (1987)) was prepared according to the literature procedure. The enantiomers were separated under chiral-SFC conditions using the following method: CHIRALPAK® AS-H 5×25; Mobile Phase: 30% MeOH+ 0.1% DEA in $CO_2$; Flow rate: 280 mL/min; Pressure: 100 bar; Temperature: 35° C.

Obtained the S-enantiomer (Preparation A-1G): HPLC: RT=1.75 min (30% MeOH+0.1% DEA in $CO_2$ on CHIRAL-PAK® AS-H 4.6×250 mm, 3 mL/min, 35° C., 100 bar, 230 nm, 10 μl injection); $^1$H NMR (400 MHz, $CDCl_3$) δ ppm 7.58-7.63 (2H, m), 7.55 (1H, ddd, J=8.50, 7.11, 1.76 Hz), 7.40-7.47 (1H, m), 7.34-7.40 (3H, m), 7.31 (1H, dd, J=7.81, 1.51 Hz), 7.14-7.22 (1H, m), 4.46 (1H, s), 3.44 (3H, s), 3.42 (2H, s); $[α]_D$=−155° (c=1.9, MeOH) (Lit. Rittle, K. E. et al., *Tetrahedron Letters*, 28(5):521-522 (1987):) [α]D=−236°.

Also obtained the R-enantiomer (Preparation A-1H): HPLC:RT=1.71 min; $[α]_D$=+165° (c=2.1, MeOH) (Lit $[α]_D$=)+227°.

Alternate Procedure to Make Preparation A-1G

Preparation A-1G•CSA salt: (3S)-3-Amino-1-methyl-5-phenyl-1,3-dihydro-2H-1,4-benzodiazepin-2-one, (1S)-(+)-10-camphorsulfonic acid salt (A-1G•CSA)

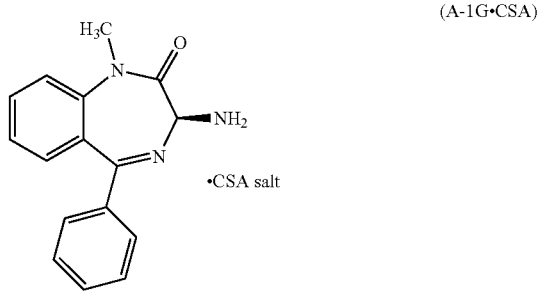

Preparation A-1G•CSA was prepared from racemic 3-amino-1-methyl-5-phenyl-1,3-dihydro-2H-1,4-benzodiazepin-2-one (9.98 g, 37.6 mmol) (prepared according to the literature as shown above) according to the literature procedure (Reider, P. J. et al., *J. Org. Chem.*, 52:955-957 (1987)). Preparation A-1G•CSA (16.91 g, 99%) was obtained as a colorless solid: Optical Rotation: $[α]_D$=−26.99° (c=1, $H_2O$) (Lit. $[α]_D$=−27.8° (c=1, $H_2O$)).

Preparation A-1I: tert-Butyl (2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoate, and Preparation A-1J: tert-Butyl (2R,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoate Preparation A-1K: (2S,3R)-6,6,6-Trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoic acid, and Preparation A-1L: (2R,3R)-6,6,6-Trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoic acid

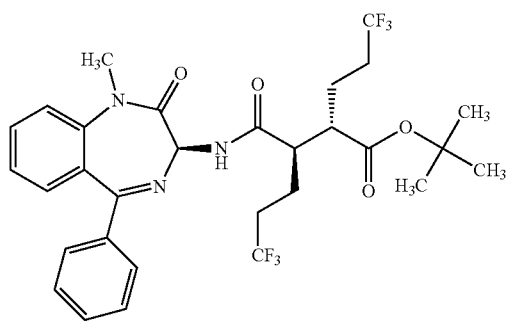

(A-1I)

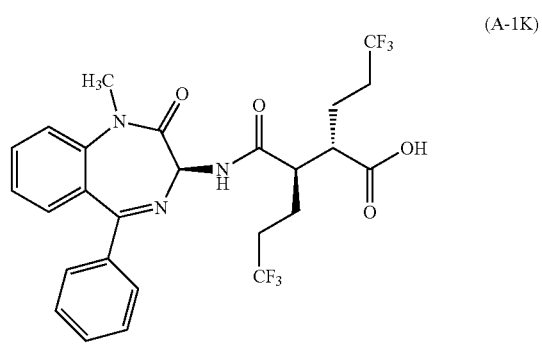

(A-1K)

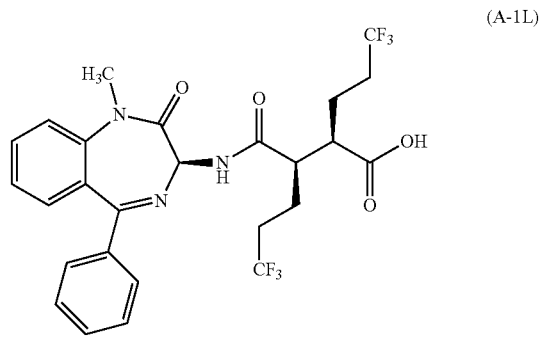 [SMILES: CN1C(=O)[C@@H](NC(=O)[C@H](CCC(F)(F)F)[C@H](CCC(F)(F)F)C(N)=O)N=C(c2ccccc2)c2ccccc21]

(A-1L)

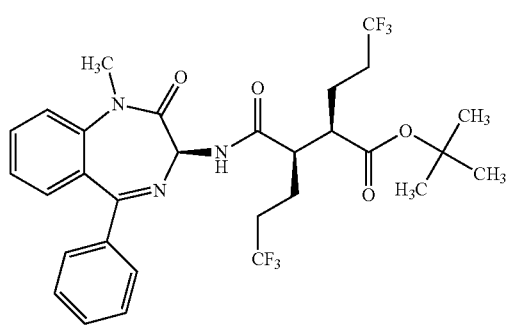

(A-1J)

To a stirred solution of Preparation A-1G (1.45 g, 5.47 mmol) and a 9:1 mixture of Preparation A-1E and 1F (1.989 g, 5.43 mmol) in DMF (19 mL) was added 0-benzotriazol-1-yl-N,N,N',N'-tetra-methyluronium tetrafluoroborate (1.79 g, 5.57 mmol) and triethylamine (3.0 mL, 21.52 mmol) and the mixture was stirred overnight. The reaction mixture was then poured into water (125 mL) and the precipitated solid was collected by filtration, washed with water and air dried to provide an 8:1 mixture of Preparation A-1I and Preparation A-1J (2.95 g, 89%) as a cream solid: MS(ES): m/z=614 [M+H]⁺; ¹H NMR (400 MHz, CDCl₃) δ ppm 7.55-7.65 (3H, m), 7.44-7.52 (2H, m), 7.35-7.45 (4H, m), 5.52 (1H, d, J=8.03 Hz), 3.48 (3H, s), 2.63 (2H, ddd, J=9.35, 3.95, 3.76 Hz), 2.14-2.25 (4H, m), 1.90-2.03 (3H, m), 1.69-1.82 (1H, m), 1.51 (9H, s).

To a cool (0° C.), stirred solution of a mixture of Preparation A-1I and Preparation A-1J (2.95 g, 4.81 mmol) in DCM (20 mL) was added TFA (20 mL, 260 mmol). The reaction mixture was stirred for 1 hr, and then allowed to warm to room temperature and stirred for 2.5 hr. The reaction mixture was diluted with toluene (50 mL) and concentrated under reduced pressure. The resulting residue was redissolved in toluene (50 mL) and concentrated under reduced pressure and then dried under high vacuum. The crude product was dissolved in DCM, SiO₂ (15 g) was added, the slurry was concentrated, and then purified by flash chromatography (Teledyne ISCO CombiFlash Rf, 0% to 45% solvent A/B=DCM/EtOAc, REDISEP® SiO₂ 80 g). Concentration of appropriate fractions provided a mixture of Preparation A-1K and Preparation A-1L (2.00 g, 75%) as a cream solid: HPLC:RT=2.770 min (CHROMOLITH® SpeedROD 4.6×50 mm (4 min grad) eluting with 10-90% aqueous MeOH over 4 minutes containing 0.1% TFA, 4 mL/min, monitoring at 254 nm); MS(ES): m/z=558 [M+H]⁺; ¹H NMR (400 MHz, CDCl₃) δ ppm 8.32 (1H, d, J=8.03 Hz), 7.65-7.71 (1H, m), 7.50-7.60 (3H, m), 7.41-7.49 (2H, m), 7.39 (1H, dd, J=7.91, 1.63 Hz), 7.23-7.35 (2H, m), 5.59 (1H, d, J=8.03 Hz), 3.51 (3H, s), 2.81 (1H, ddd, J=10.54, 6.90, 3.64 Hz), 2.67-2.76 (1H, m), 2.22-2.33 (3H, m), 1.99-2.12 (3H, m), 1.85-1.94 (1H, m), 1.79 (1H, ddd, J=13.87, 7.84, 3.64 Hz).

Compound A

To a stirred solution of an 8:1 mixture of Preparation A-1K and Preparation A-1L (3.46 g, 6.21 mmol) in DMF (25 mL) under a nitrogen atmosphere was added ammonium chloride (3.32 g, 62.1 mmol), EDCI (3.55 g, 18.52 mmol), HOBT (2.85 g, 18.61 mmol), and triethylamine (16 mL, 115 mmol) and the mixture was stirred overnight. The reaction mixture was poured into water (200 mL) with vigorous swirling and then allowed to sit. The resulting solid was collected by filtration, washed with water, and allowed to dry to afford 3.6 g of a colorless solid. The solid was purified by preparative SFC chromatography (Lux-Cellulose-2 (3×25 cm), 8% methanol in $CO_2$, 140 ml/min @220 nm and 35° C.; Sample: 3.6 g in 50 cc methanol, conc.=70 mg/ml, Stack injection: 0.5 cc/9.2 min). Fractions containing desired product were concentrated and dried overnight under vacuum. Obtained Compound A (2.74 g, 79%) as a colorless solid: HPLC:RT=9.601 min ($H_2O/CH_3CN$ with TFA, SunFire C18 3.5 um, 4.6×150 mm, 4.6×150 mm, gradient=15 min, wavelength=220 and 254 nm). MS(ES): m/z=557 $[M+H]^+$; $^1H$ NMR (400 MHz, DMSO-$d_6$) δ ppm 9.54 (1H, d, J=7.28 Hz), 7.71-7.80 (1H, m), 7.68 (2H, d, J=8.78 Hz), 7.50-7.62 (3H, m), 7.45 (2H, t, J=7.28 Hz), 7.29-7.40 (2H, m), 7.15 (1H, br. s.), 5.30 (1H, d, J=7.28 Hz), 3.39 (3H, s), 2.74-2.86 (1H, m), 2.02-2.32 (3H, m), 1.45-1.79 (4H, m);

Alternate Procedure to Make Compound A

Preparation A-1M: 3,3,3-Trifluoropropyl trifluoromethanesulfonate

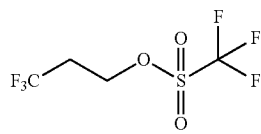

(A-1M)

To a cold (−25° C.), stirred solution of 2,6-lutidine (18.38 mL, 158 mmol) in $CH_2Cl_2$ (120 mL) was added $Tf_2O$ (24.88 mL, 147 mmol) over 3 min, and the mixture was stirred for 5 min. To the reaction mixture was added 3,3,3-trifluoropropan-1-ol (12 g, 105 mmol) over an interval of 3 min. After 2 hr, the reaction mixture was warmed to room temperature and stirred for 1 hr. The reaction mixture was then concentrated to half its volume and was then purified by loading directly on a silica gel column (330 g ISCO) and eluting with $CH_2Cl_2$. Obtained Preparation A-1M (13.74 g, 53%) as a colorless oil. $^1H$ NMR (400 MHz, CDCl$_3$) δ ppm 4.71 (2H, t, J=6.15 Hz), 2.49-2.86 (2H, m).

Preparation A-1N: (4S)-4-Benzyl-3-(5,5,5-trifluoropentanoyl)-1,3-oxazolidin-2-one

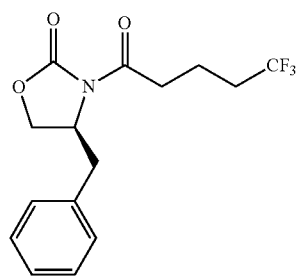

(A-1N)

Preparation A-1N was prepared from 5,5,5-trifluoropentanoic acid (3.35 g, 21.46 mmol) and (4S)-4-benzyl-1,3-oxazolidin-2-one (3.80 g, 21.46 mmol) by the general methods shown for Preparation A-1B. Preparation A-1N (5.67 g, 84%) was obtained as a colorless viscous oil: $^1H$ NMR (400 MHz, CDCl$_3$) δ ppm 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Preparation A-1O: tert-Butyl (3R)-3-(((4S)-4-benzyl-2-oxo-1,3-oxazolidin-3-yl)carbonyl)-6,6,6-trifluorohexanoate

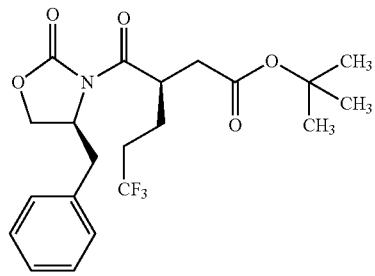

(A-1O)

To a cold (−78° C.), stirred solution of Preparation A-1N (3.03 g, 9.61 mmol) in THF (20 mL) was added NaHMDS (1.0M in THF) (10.6 mL, 10.60 mmol) under a nitrogen atmosphere. After 2 hours, tert-butyl 2-bromoacetate (5.62 g, 28.8 mmol) was added neat via syringe at −78° C. and stirring was maintained at the same temperature. After 6 hours, the reaction mixture was warmed to room temperature. The reaction mixture was partitioned between saturated $NH_4Cl$ and EtOAc. The organic phase was separated, and the aqueous layer was extracted with EtOAc (3×). The combined organics were washed with brine, dried ($Na_2SO_4$), filtered and concentrated under reduced pressure. The residue was purified by flash chromatography (Teledyne ISCO CombiFlash Rf, 5% to 100% solvent A/B=hexanes/EtOAc, REDISEP® $SiO_2$ 120 g). Concentration of appropriate fractions provided Preparation A-1O (2.79 g, 67.6%) as a colorless viscous oil: $^1H$ NMR (400 MHz, CDCl$_3$) δ ppm 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Preparation A-1P: (2R)-2-(2-tert-Butoxy-2-oxoethyl)-5,5,5-trifluoropentanoic acid

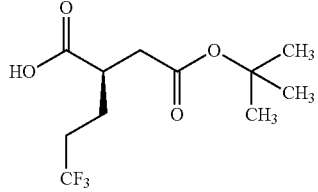

(A-1P)

Preparation A-1P was prepared from Preparation A-1O (2.79 g, 6.50 mmol) by the general methods shown for Preparation A-1E. Preparation A-1P (1.45 g, 83%) was obtained as a colorless oil: ¹H NMR (400 MHz, CDCl₃) δ ppm 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Preparation A-1E: (2R,3S)-3-(tert-Butoxycarbonyl)-6,6,6-trifluoro-2-(3,3,3-trifluoropropyl)hexanoic acid, and Preparation A-1F: (2R,3R)-3-(tert-Butoxycarbonyl)-6,6,6-trifluoro-2-(3,3,3-trifluoropropyl)hexanoic acid

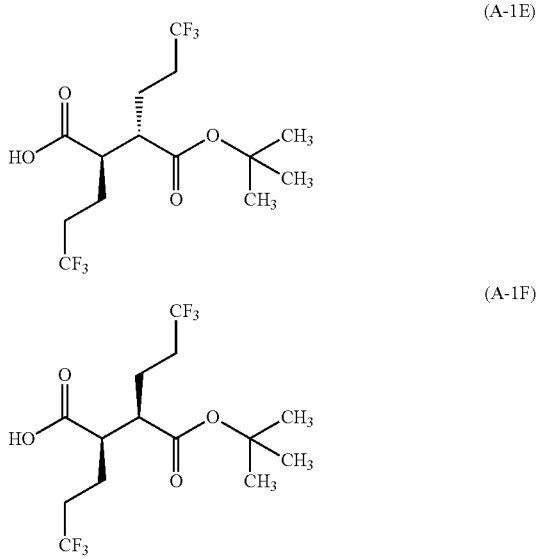

(A-1E)

(A-1F)

To a cold (−78° C.), stirred solution of Preparation A-1P (5.44 g, 20.13 mmol) in THF (60 mL) was slowly added LDA (24.60 mL, 44.3 mmol) over 7 min. After stirring for 2 hr, Preparation A-1M (6.44 g, 26.2 mmol) was added to the reaction mixture over 3 min. After 45 min, the reaction mixture was warmed to −25° C. (ice/MeOH/dry ice) for 1 hr, and then warmed to 0° C. After 45 min, Preparation A-1M (1 g) was added and the reaction mixture was stirred for 20 min. The reaction was quenched with water and 1N NaOH and was extracted with CH₂Cl₂. The organic layer was again extracted with 1N NaOH (2×) and the aqueous layers were combined. The aqueous layer was cooled in an ice/water bath and then acidified with concentrated HCl to pH 2. Next, the aqueous layer was extracted with EtOAc. The combined organics were washed with brine, dried over anhydrous sodium sulfate, and concentrated under reduced pressure. The residue was dried under high vacuum to provide a 1:5 (A-1E:A-1F) mixture (as determined by ¹H NMR) of Preparation A-1E and Preparation A-1F (5.925 g, 80%) as a pale yellow solid. ¹H NMR (500 MHz, CDCl₃) δ ppm 2.81 (1H, ddd, J=10.17, 6.32, 3.85 Hz), 2.63-2.76 (1H, m), 2.02-2.33 (4H, m), 1.86-1.99 (2H, m), 1.68-1.85 (2H, m), 1.47 (9H, s).

Preparation A-1E: (2R,3S)-3-(tert-Butoxycarbonyl)-6,6,6-trifluoro-2-(3,3,3-trifluoropropyl)hexanoic acid, and Preparation A-1F: (2R,3R)-3-(tert-Butoxycarbonyl)-6,6,6-trifluoro-2-(3,3,3-trifluoropropyl)hexanoic acid

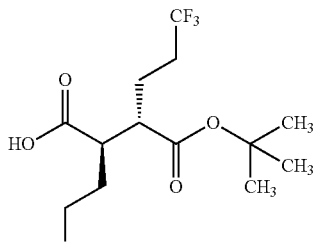

(A-1E)

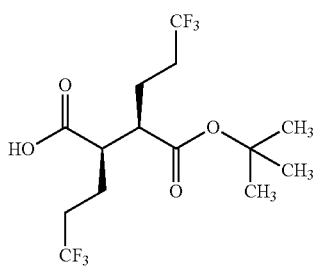

(A-1F)

A mixture of Preparation A-1E and Preparation A-1F (64 mg, 1.758 mmol) was dissolved in THF (6 mL) to give a colorless solution which was cooled to −78° C. Then, LDA (2.149 mL, 3.87 mmol) (1.8M in heptane/THF/ethylbenzene) was slowly added to the reaction mixture over 10 min. After stirring for 15 min the reaction mixture was placed in a room temperature water bath. After 15 min the reaction mixture was placed back in a −78° C. bath and then diethylaluminum chloride (3.87 mL, 3.87 mmol) (1M in hexane) was added slowly over 5 min. The reaction mixture was stirred at −78° C. After 15 min the reaction mixture was placed in a room temperature water bath for 10 min and then cooled back to −78° C. bath. After 15 min the reaction was quenched with MeOH (8 mL, 198 mmol), removed from the −78° C. bath and concentrated. To the reaction mixture was added ice and HCl (16 mL, 16.00 mmol), and the mixture was extracted with EtOAc (2×). The organic layer was washed with potassium fluoride (920 mg, 15.84 mmol) (in 25 mL H₂O) and HCl (4.5 mL, 4.50 mmol). The organics were dried over anhydrous magnesium sulfate and concentrated under reduced pressure to provide a 9:1 (A-1E:A-1F) enriched mixture of Preparation A-1E and Preparation A-1F (540 mg, 1.583 mmol, 90% yield) as a light yellow/orange solid. ¹H NMR (400 MHz, CDCl₃) δ ppm 2.64-2.76 (2H, m), 2.04-2.35 (4H, m), 1.88-2.00 (2H, m), 1.71-1.83 (2H, m), 1.48 (9H, s).

Alternate Procedure to Make Preparation A-1E

Preparation A-1Q: (2R,3S)-1-Benzyl 4-tert-butyl 2,3-bis(3,3,3-trifluoropropyl)succinate

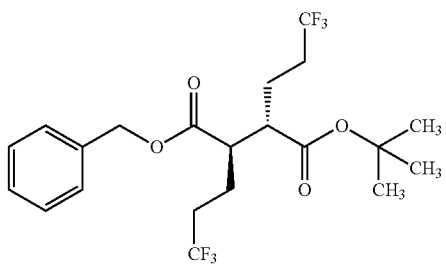

(A-1Q)

A clean and dry 5 L four neck round bottom flask equipped with mechanical stirring, thermometer socket and nitrogen bubbler at room temperature was charged with N,N-dimethyl formamide (2.07 L), a 1.2:1 mixture of Preparation A-1E and Preparation A-1F (207 g, 0.5651 moles), and potassium carbonate (117.1 g, 0.8476 moles) followed by benzyl bromide (116 g, 0.6781 moles) over 15-20 min. The reaction mixture was stirred for 2-3 hr. After completion of the reaction, the reaction mixture was concentrated to dryness at 50-55° C. under vacuum. Ethyl acetate (3.1 L, 30 Vol.) was charged into the concentrated reaction mass and the mixture was then washed with water (2.07 L) and brine (0.6 L) and then dried over anhydrous sodium sulfate (207 g), filtered and concentrated to dryness at 40-45° C. under vacuum. The residue was dissolved in dichloromethane (1.035 L, 5 vol.) and then absorbed onto silica gel (60-120) (607 g, 3.0 w/w), and then purified with column chromatography using petroleum ether and ethyl acetate as solvents. After pooling several batches, Preparation A-1Q (235 g) was obtained. HPLC purity: 99.77%.

Preparation A-1E: (2R,3S)-3-(tert-Butoxycarbonyl)-6,6,6-trifluoro-2-(3,3,3-trifluoropropyl)hexanoic acid

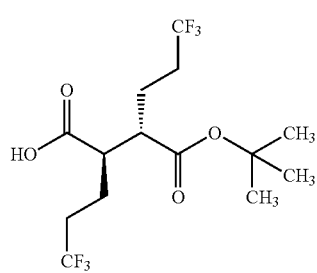

(A-1E)

A clean and dry 2 L autoclave was charged with methanol (540 mL) and was purged with nitrogen for 5-10 minutes. To the autoclave was added 10% palladium on carbon (12 g, 20%), and the vessel was purged with nitrogen once again for 5-10 min. Preparation A-1Q (60 g, 0.1315 moles) was added and the autoclave was flushed with methanol (60 mL) and stirred for 4-6 hr at 20-25° C. under 5 kg of hydrogen pressure. After completion of the reaction, the reaction mass was filtered through CELITE®, washed with methanol (180 mL), dried with anhydrous sodium sulfate (60 g), filtered and concentrated to dryness at 45-50° C. under vacuum to afford Preparation A-1E (45.8 g, 95%) as a colorless solid: HPLC purity: 98.9%.

Alternate Procedure to Make Preparation A-1E

Preparation A-1E: (2R,3S)-3-(tert-Butoxycarbonyl)-6,6,6-trifluoro-2-(3,3,3-trifluoropropyl)hexanoic acid

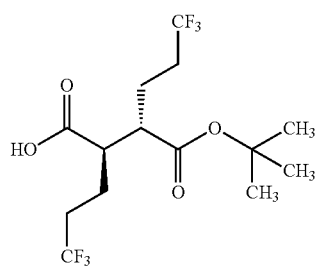

(A-1E)

Preparation A-1E was prepared in a procedure identical as above from a mixture of Preparations A-1E and A-1F (200 g, 0.5460 moles) using LDA (1.8 M solution in THF, ethyl benzene and heptane) (698 mL, 2.3 equiv.) and diethyl aluminum chloride (1.0 M solution in hexane) (1256 mL, 2.3 equiv) in THF (2.0 L). After workup as explained above, the resulting residue was treated as follows: The crude material was added to a 2L four neck round bottom flask, followed by the addition of MTBE (1.0 L), charged below 30° C. The resulting mixture was stirred for 5-10 minutes to obtain a clear solution. Hexanes (600 mL) was charged to the reaction mixture at a temperature below 30° C. The reaction mixture was stirred for 10 min. Next, tert-butylamine (43.8 g, 1.1 eq) was charged slowly over a period of 15 minutes below 30° C. The reaction mixture was stirred for 2 hrs below 30° C. and then filtered. The solid material was washed with 5:3 MTBE: hexane (200 mL), the filtrate was concentrated and transferred to an amber color bottle. The filtered solid was dissolved in dichloromethane (2.0 L) and washed with 1N HCl (2.0). The organic layer was washed with brine (1.0L×2), and then concentrated under reduced pressure below 45° C. This material was found to be 91.12% pure. The material was repurified by the above t-butylamine crystallization purification procedure to obtain Preparation A-1E (78 g, 39%): HPLC purity: 99.54%.

Alternate Procedure to Make Compound A

Preparation A-1I: tert-Butyl (2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoate

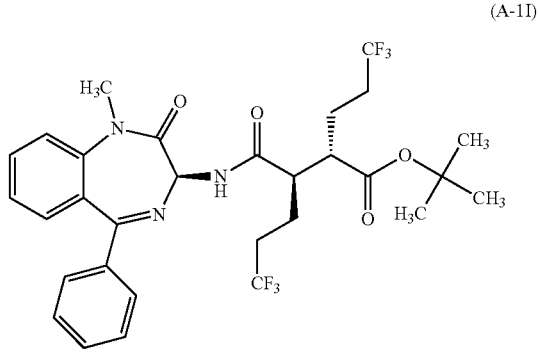 [SMILES: CN1C(=O)[C@@H](NC(=O)[C@H](CCC(F)(F)F)[C@H](CCC(F)(F)F)C(=O)OC(C)(C)C)N=C(c2ccccc2)c2ccccc21]

(A-1I)

A clean and dry 2 L four neck round bottom flask equipped with mechanical stirring, thermometer socket and nitrogen bubbler was charged with N,N-dimethylformamide (457 mL), Preparation A-1E (45.7 g, 0.1248 moles) and Preparation A-1G•CSA (62.08 g, 0.1248 moles) under a nitrogen atmosphere at 20-25° C. The reaction mixture was stirred for 15-20 minutes to make a clear solution at 20-25° C. To the reaction mixture was added TBTU (48.16 g, 0.1498 moles) at 20-25° C., followed by triethylamine (50.51 g, 0.4992 moles) over 15-20 minutes at 20-25° C. The reaction mixture was stirred for 60-120 minutes at 20-25° C. under a nitrogen atmosphere. After completion of the reaction, the reaction was poured into water (1.37L, 30 Vol.) at 20-25° C. with stirring. The reaction mixture was stirred for 30 minutes at 20-25° C. The reaction mixture was filtered and washed with water (228 mL). The resulting solid material was dissolved in ethyl acetate (457 mL), washed with water (2×137 mL), brine (137 mL), and then dried with anhydrous sodium sulfate (45.7 g). Activated charcoal (9.14 g, 20%) was charged into the reaction mixture and stirred for 30 minutes. The mixture was filtered through a CELITE® bed and 1 micron filter cloth, the charcoal bed was washed with ethyl acetate (137 mL), concentrated to 1.0 Vol. stage and then petroleum ether (457 mL, 10 Vol.) was charged and the mixture was stirred for 30 minutes at 20-25° C. The solid was collected by filtration, washed with petroleum ether (137 mL) and then dried under vacuum at 40-45° C. for 8 hr until loss on drying was less than 3.0%. Obtained Preparation A-1I (65.2 g, 85%): HPLC purity: 98.26%.

Preparation A-1K: (2S,3R)-6,6,6-Trifluoro-3-(((3S)-1-methyl-2-oxo-5-phenyl-2,3-dihydro-1H-1,4-benzodiazepin-3-yl)carbamoyl)-2-(3,3,3-trifluoropropyl) hexanoic acid

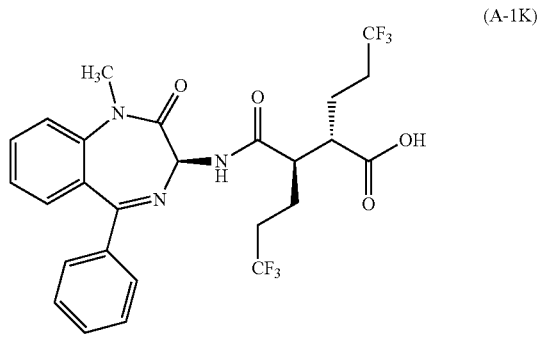

A clean and dry 3 L four neck round bottom flask equipped with mechanical stirring, thermometer socket and nitrogen bubbler was charged with dichloromethane (980 mL) under a nitrogen atmosphere followed by the addition of Preparation A-1I (140 g, 0.2282 moles) at 20-25° C. The reaction mixture was cooled to 0-5° C. and trifluoroacetic acid (980 mL) was charged slowly over 30-40 minutes. The resulting mixture was stirred for 2 hr at 0-5° C. under a nitrogen atmosphere. The reaction temperature was raised to 20-25° C., and the reaction mixture was stirred for 1-2 hr at 20 to 25° C. After completion of the reaction, the reaction mixture was concentrated to dryness at 50 to 55° C. under vacuum. Toluene (3×700 mL) was charged into the concentrated reaction mass, and then distilled off at 50 to 55° C. under vacuum. After complete concentration from toluene, ethyl acetate (280 mL) was charged into the reaction mass at 20 to 25° C., stirred for 60 minutes, and then the solid was collected by filtration. The resulting solid was washed with ethyl acetate (140 mL), dried under vacuum at 50 to 55° C. for 12 hr until loss on drying was less than 2.0%. Obtained Preparation A-1K (106 g, 84%): HPLC purity: 98.43%.

Compound A

A reaction vessel was charged with Preparation A-1K (30 g, 53.81 mmol), HOBt (8.7 g, 64.38 mmol), and THF (150 mL) at room temperature. To the homogeneous solution was added EDCI (12.4 g, 64.68 mmol), and the mixture was stirred for 15 min, and then cooled to 8° C. To the reaction mixture was added ammonia (2M in IPA) (81 mL, 162 mmol) over 5 min so as to maintain a temperature below 10° C. The resulting heavy slurry was stirred for 10 min, warmed to room temperature over 30 min, and then stirred for 4 hr. At the completion of the reaction, water (230 mL) was slowly added over 15 min to maintain a temperature below 20° C., and the resulting mixture was stirred for 2 hr. The solid was collected by filtration, washed with water (3×60 mL), and then dried under vacuum for 48 hr at 55° C. The above crude product was charged into a 1 L 3-necked round flask. IPA (200 mL) was added, and the mixture was heated to 80° C. resulting in a homogeneous solution. Water (170 mL) was slowly added (15 min) to maintain an internal temperature >75° C. The resulting slurry was stirred and cooled to room temperature for 2 hr. The solid was collected by filtration, washed with water (2×50 mL), then dried under vacuum (55° C. for 24 h, and 30° C. for 48 h). Obtained Compound A (23.4 g, 78% yield): HPLC purity: 99.43%.

Compound B (2R,3S)—N-((3S)-2-Oxo-5-phenyl-2,3-dihydro-1H-1,4-benzodiazepin-3-yl)-2,3-bis(3,3,3-trifluoropropyl)succinamide

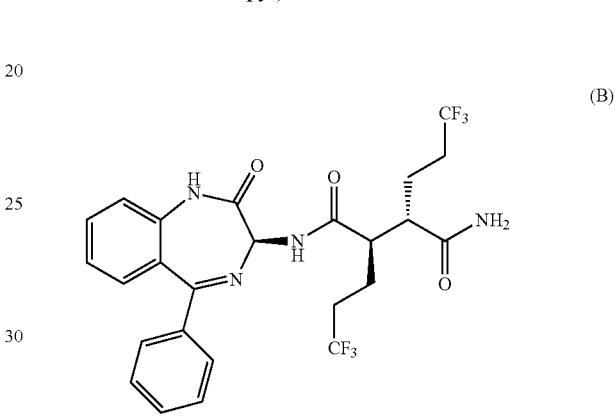

Preparation B-2A: (3S)-3-Amino-5-phenyl-1,3-dihydro-2H-1,4-benzodiazepin-2-one, and Preparation B-2B: (3R)-3-Amino-5-phenyl-1,3-dihydro-2H-1,4-benzodiazepin-2-one

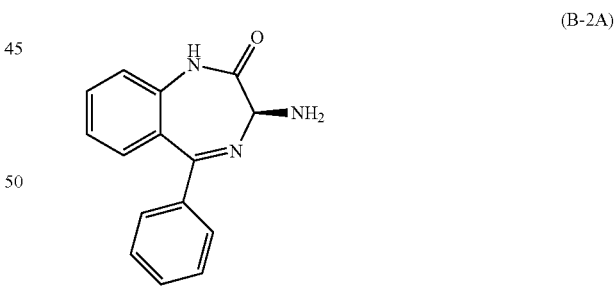

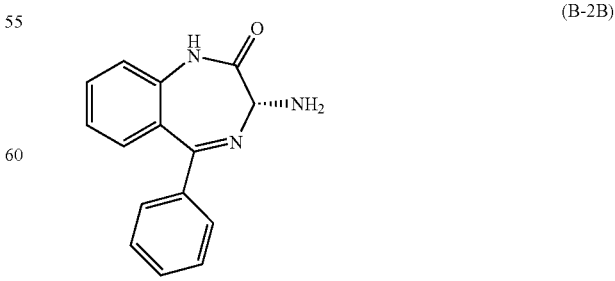

Racemic 3-amino-5-phenyl-1,3-dihydro-2H-1,4-benzodiazepin-2-one (*J. Med. Chem.*, 49:2311-2319 (2006), compound #5) was prepared according to the literature procedure. The enantiomers were separated on Berger SFC MGIII Column: Lux 25×3 cm, 5 cm; Mobile Phase: 30% MeOH+0.1% DEA in $CO_2$; Flow rate: 150 mL/min; Temperature: 40° C.; Detector wavelength: 250 nM. Obtained the S-enantiomer Preparation B-2A as a white solid: $^1$H NMR (400 MHz, DMSO-$d_6$) δ ppm 10.67 (1H, br. s.), 7.58 (1H, td, J=7.65, 1.76 Hz), 7.37-7.53 (5H, m), 7.23-7.30 (2H, m), 7.14-7.22 (1H, m), 4.23 (1H, s), 2.60 (2H, br. s.); HPLC:RT=3.0625 min (30% MeOH+0.1% DEA in $CO_2$ on OD-H Column, 3 mL/min, 35° C., 96 bar, 230 nm, 10 μl inj); $[α]_D$=−208.3° (5.05 mg/mL, MeOH). Also obtained the R-enantiomer Preparation B-2B as an off-white solid: HPLC:RT=3.970 min; $[α]_D$=182.1° (2.01 mg/mL, MeOH).

Preparation B-2C: tert-Butyl (2S,3R)-6,6,6-trifluoro-3-(((3S)-2-oxo-5-phenyl-2,3-dihydro-1H-1,4-benzodiazepin-3-yl)carbamoyl)-2-(3,3,3-trifluoropropyl) hexanoate, and Preparation B-2D: tert-Butyl (2R,3R)-6,6,6-trifluoro-3-(((3S)-2-oxo-5-phenyl-2,3-dihydro-1H-1,4-benzodiazepin-3-yl)carbamoyl)-2-(3,3,3-trifluoropropyl) hexanoate

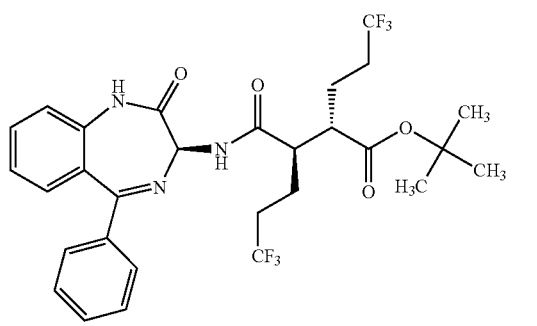

(B-2C)

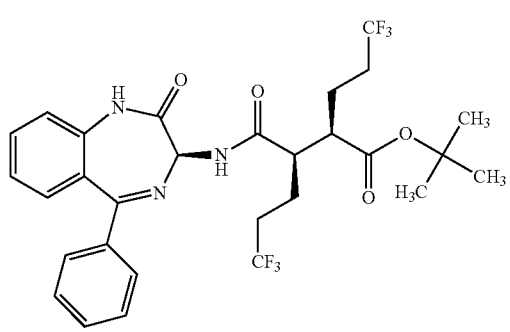

(B-2D)

Preparation B-2C was prepared from Preparation B-2A (564 mg, 2.244 mmol) and a mixture of Preparation A-1E and Preparation A-1F (822 mg, 2.244 mmol) according to the general procedure shown for Preparation A-1I. Obtained Preparation B-2C and Preparation B-2D (1.31 g, 97%): HPLC:RT=3.443 min (CHROMOLITH® ODS 4.6×50 mm (4 min grad) eluting with 10-90% aqueous MeOH over 4 minutes containing 0.% TFA, 4 mL/min, monitoring at 220 nm); MS(ES): m/z=600.3 $[M+H]^+$.

Preparation B-2E: (2S,3R)-6,6,6-Trifluoro-3-(((3S)-2-oxo-5-phenyl-2,3-dihydro-1H-1,4-benzodiazepin-3-yl)carbamoyl)-2-(3,3,3-trifluoropropyl)hexanoic acid, and Preparation B-2F: (2R,3R)-6,6,6-Trifluoro-3-(((3S)-2-oxo-5-phenyl-2,3-dihydro-1H-1,4-benzodiazepin-3-yl)carbamoyl)-2-(3,3,3-trifluoropropyl)hexanoic acid

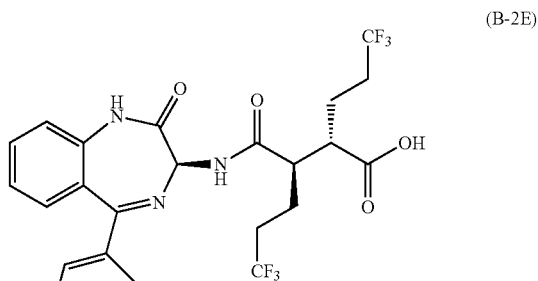

(B-2E)

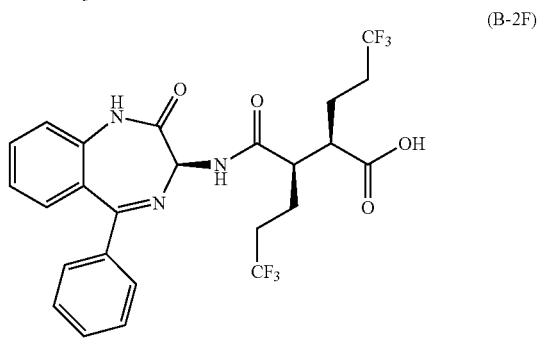

(B-2F)

A mixture of Preparation B-2E and Preparation B-2F was prepared from a mixture of Preparation B-2C and Preparation B-2D (1.31 g, 2.185 mmol) by the general methods shown for Preparation A-1K. Obtained a mixture of Preparation B-2E and Preparation B-2F (1.18 g, 99%): HPLC:RT=2.885 min (CHROMOLITH® ODS 4.6×50 mm (4 min grad) eluting with 10-90% aqueous MeOH over 4 minutes containing 0.% TFA, 4 mL/min, monitoring at 220 nm). MS(ES): m/z=544.2 $[M+H]^+$.

Compound B

Compound B was prepared from a mixture of Preparation B-2E and Preparation B-2F (354 mg, 0.651 mmol) by the general methods shown for Compound A. After separation of the diastereoisomers, Compound B was obtained (188 mg, 52%) as a white solid: HPLC:RT=9.063 min ($H_2O/CH_3CN$ with TFA, SunFire C18 3.5 um, 4.6×150 mm, 4.6×150 mm, gradient=15 min, wavelength=220 and 254 nm); MS(ES): m/z=543 $[M+H]^+$; $^1$H NMR (400 MHz, DMSO-$d_6$) δ ppm 10.87 (1H, br. s.), 9.50-9.55 (1H, m), 7.62-7.69 (2H, m), 7.40-7.57 (5H, m), 7.29-7.36 (2H, m), 7.22-7.28 (1H, m), 7.16 (1H, br. s.), 5.25 (1H, d), 3.30-3.32 (1H, m), 2.75-2.86 (1H, m), 2.44-2.48 (1H, m), 2.06-2.34 (3H, m), 1.51-1.77 (4H, m); $[α]_D$=−114.4° (8.04 mg/mL, DMSO).

Example 1

((3S)-3-(((2R,3S)-3-Carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl (4-(phosphonooxy)phenyl)acetate

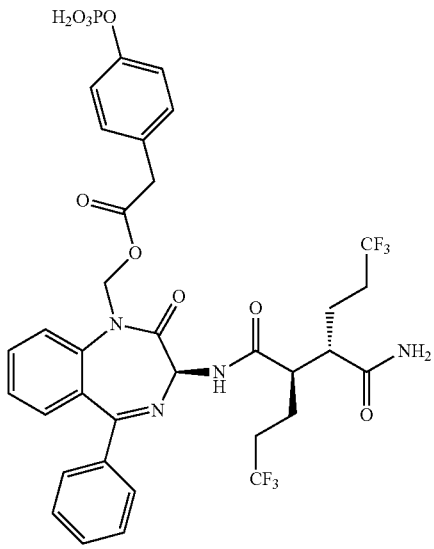
(1)

Preparation 1A: (2R,3S)—N1-((S)-1-((Methylthio)methyl)-2-oxo-5-phenyl-2,3-dihydro-1H-benzo[e][1,4]diazepin-3-yl)-2,3-bis(3,3,3-trifluoropropyl)succinamide

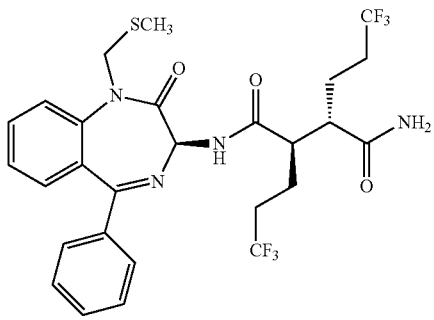
(1A)

To a solution of Compound B (0.020 g, 0.037 mmol) in DMF (0.5 mL) was added Cs$_2$CO$_3$ (0.036 g, 0.111 mmol). The reaction mixture was stirred under nitrogen for 10 minutes, and then (chloromethyl)(methyl) sulfane (8.90 mg, 0.092 mmol) was added. The reaction mixture was stirred at room temperature under nitrogen for 2 hr, and then diluted with EtOAc (3 mL) and washed with brine (2×2 mL), dried (Na$_2$SO$_4$), and concentrated under vacuum at 45° C. The crude material was purified by Prep-TLC (SiO$_2$, 50% EtOAc/petroleum ether) to afford 15 mg of the title compound, which was used in the next step. MS(ES): m/z=603 [M+H]$^+$.

Preparation 1B: (2R,3S)—N1-((S)-1-(Chloromethyl)-2-oxo-5-phenyl-2,3-dihydro-1H-benzo[e][1,4]diazepin-3-yl)-2,3-bis(3,3,3-trifluoropropyl)succinamide

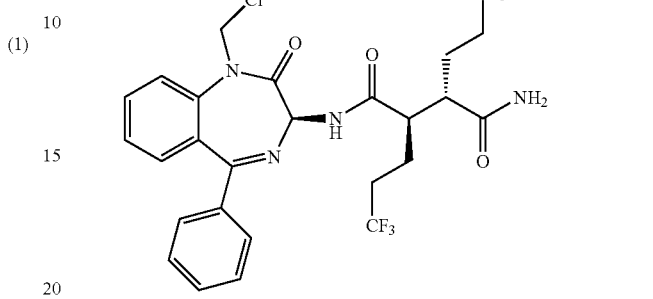
(1B)

To a solution of Preparation 1A (0.015 g, 0.025 mmol) in DCM (0.5 mL) was added triethylamine hydrochloride (5.14 mg, 0.037 mmol). The reaction mixture was stirred at room temperature for 5 min and then sulfuryl chloride (2.53 µl, 0.031 mmol) was added dropwise under nitrogen at 0° C. The reaction mixture was stirred at room temperature for 2 hr and then concentrated under reduced pressure at 10° C. The resulting crude sample was taken forward in the next step without further purification: MS(ES): m/z=587 [M+H]$^+$.

Preparation 1C: ((S)-3-((2R,3S)-3-Carbamoyl-6,6,6-trifluoro-2-(3,3,3-trifluoropropyl)hexanamido)-2-oxo-5-phenyl-2,3-dihydro-1H-benzo[e][1,4]diazepin-1-yl)methyl 2-(4-((di-tert-butoxyphosphoryl)oxy)phenyl)acetate

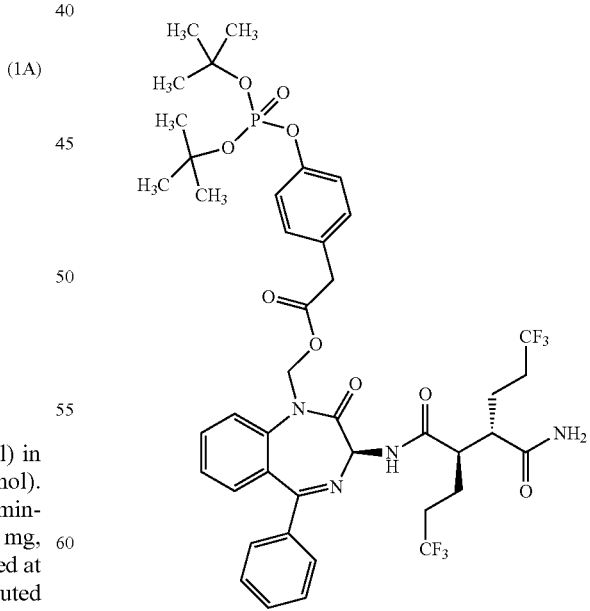
(1C)

To a solution of Preparation 1B (0.015 g, 0.025 mmol) in DMF (0.5 mL) was added 2-(4-((di-tert-butoxyphosphoryl)oxy)phenyl)acetic acid (0.015 g, 0.044 mmol), Cs$_2$CO$_3$ (0.035 g, 0.107 mmol), and sodium iodide (3.80 mg, 0.025 mmol). The reaction mixture was stirred at room temperature under a nitrogen atmosphere for 10 min. The mixture was then treated with water (5 mL) and extracted with EtOAc (3×3 mL). The combined organic layers were dried (Na₂SO₄), filtered and concentrated to dryness at 45° C. The crude material was purified by preparative reversed phase HPLC to afford Preparation 1C (0.020 g): MS(ES): m/z=899 [M+H]⁺.

Example 1

To a solution of Preparation 1C (0.020 g, 0.022 mmol) in DCM (0.5 mL) was added three equivalents of a 1M HCl in ether solution at 0° C. The reaction mixture was stirred at room temperature under a nitrogen atmosphere for 4 h, and then an additional 2 equivalents of a 1M HCl in ether solution was added to the reaction mixture and stirring was continued at room temperature for another 2 hours. A final addition of 1 M HCl in ether (2 equivalents) was added and the reaction mixture was stirred for an additional two hours until the starting material had disappeared. The solvent was removed under a stream of nitrogen and the resulting crude product was dried under reduced pressure. The crude material was purified by preparative reversed-phase HPLC (Column: Symmetry C18 (300×19) mm, 7 micron, flow: 17 mL/min, Mobile Phase A: 0.1% TFA in water, Mobile Phase B: ACN) to afford Example 1 (0.009 g, 49%): ¹H NMR (400 MHz, DMSO-d₆) δ ppm 9.58 (d, J=7.2 Hz, 1H), 7.66-7.76 (m, 3H), 7.40-7.59 (m, 6H), 7.28 (d, J=7.6 Hz, 1H), 7.15 (br s, 1H), 7.00 (s, 4H), 5.94 (d, J=10.4 Hz, 1H), 5.81 (d, J=10.4 Hz, 1H), 5.39 (d, J=7.2 Hz, 1H), 2.77-2.85 (m, 1H), 2.08-2.38 (m, 4H), 1.50-1.76 (m, 5H), 1.20-1.31 (m, 3H); HPLC:RT=11.765 min (Column: XBridge Phenyl (4.6×150) mm, 3.5 micron, Buffer: 0.05% TFA in water pH 2.5 adjusted with dilute NH₃, Mobile Phase A: Buffer: Acetonitrile (95:5), Mobile Phase B: Acetonitrile:Buffer (95:5), Flow rate: 1 ml\min, monitored at 220 nm); MS(ES): m/z=787 (M+H)⁺.

Example 2

((3S)-3-(((2R,3S)-3-Carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 4-((phosphonooxy)methyl)benzoate (2)

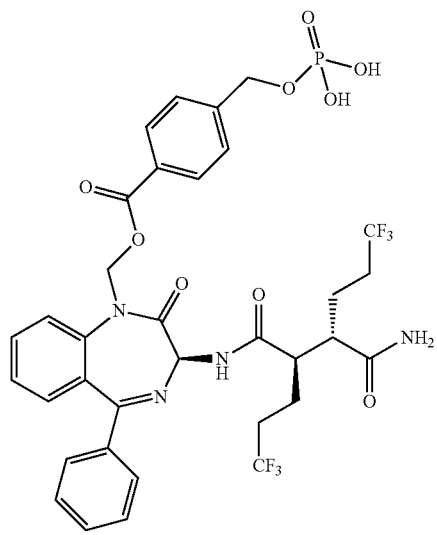

Preparation 2A: ((S)-3-((2R,3S)-3-Carbamoyl-6,6,6-trifluoro-2-(3,3,3-trifluoropropyl) hexanamido)-2-oxo-5-phenyl-2,3-dihydro-1H-benzo[e][1,4]diazepin-1-yl)methyl 4-(((di-tert-butoxyphosphoryl)oxy)methyl)benzoate (2A)

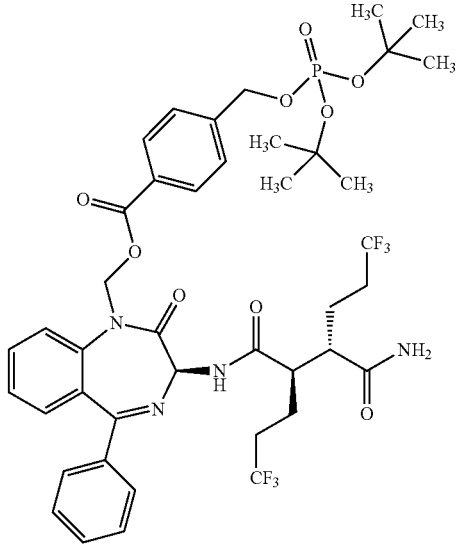

A solution of Preparation 1B (30 mg, 0.051 mmol), 4-(((di-tert-butoxyphosphoryl)oxy)methyl)benzoic acid (30.6 mg, 0.089 mmol), and Cs₂CO₃ (69.5 mg, 0.213 mmol) were combined in DMF (1 mL) and stirred at room temperature for 2 hours. The reaction mixture was then diluted with 10 mL of water and 30 mL of EtOAc. The layers were separated and the aqueous layer was extracted with EtOAc (2×20 mL). The combined organic extracts were washed with brine (20 mL), dried (Na₂SO₄), filtered and concentrated in vacuo. The crude material was purified by preparative TLC (SiO₂, 50% EtOAc/petroleum ether) to obtain Preparation 2A (22 mg, 0.015 mmol, 28.9% yield) which was taken directly into the next step. MS(ES): m/z=899 (M+H)⁺.

Example 2

To a stirred solution of Preparation 2A (22 mg, 0.024 mmol) in anhydrous DCM (0.5 mL) under nitrogen was added 1N HCl in ether (0.245 mL, 0.245 mmol) at room temperature. After 2 hours, an additional 0.5 mL of 1N HCl in ether was added and the reaction mixture was stirred for 45 min. Additional 1N HCl (0.5 mL) in ether was added after 1 hour and the reaction mixture was stirred until the starting material was consumed. The resulting reaction mixture was concentrated and the resulting crude product was purified by preparative reversed-phase HPLC (Column: Symmetry C18 (300×19) mm, 7 micron, flow: 17 mL/min, Mobile Phase A: 0.1% TFA in water, Mobile Phase B: ACN) to afford Example 2 (3.6 mg, 4.30 μmol, 17.58% yield) as a white solid. ¹H NMR (400 MHz, DMSO-d₆) δ ppm 9.58 (d, J=7.28 Hz, 1H), 7.86-7.89 (m, 1H), 7.75-7.82 (m, 1H), 7.64-7.73 (m, 3H), 7.31-7.53 (m, 9H) 7.12-7.17 (m, 1H), 6.10-6.17 (m, 2H), 5.45 (d, J=7.2 Hz, 1H), 4.91-4.93 (m, 2H), 2.77-2.85 (m, 1H), 2.32-2.38 (m, 1H), 2.08-2.30 (m, 3H), 1.50-1.76 (m, 5H); HPLC: RT=9.462 min (Column: SunFire C18 (4.6×150) mm, 3.5 micron, Buffer: 0.05% TFA in water pH 2.5 adjusted with dilute NH$_3$, Mobile Phase A: Buffer: Acetonitrile (95:5), Mobile Phase B: Acetonitrile:Buffer (95:5), Flow rate: 1 ml\min, monitored at 220 nm); MS(ES): m/z=787 (M+H)$^+$.

Example 3

(3-(((2R,3S)-3-Carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 3-(2,4-dimethyl-6-(phosphonooxy)phenyl)-3-methylbutanoate

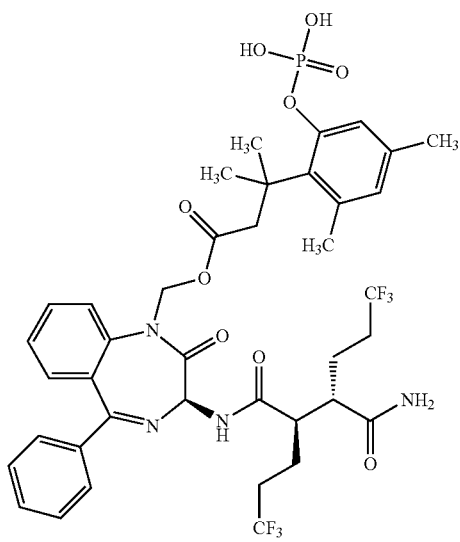

(3)

Preparation 3A: 2-(4-Hydroxy-2-methylbutan-2-yl)-3,5-dimethylphenol

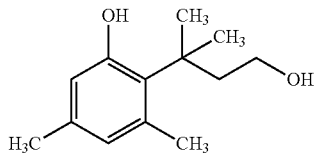

(3A)

To a stirred solution of 4,4,5,7-tetramethylchroman-2-one (2.7 g, 13.22 mmol) in THF (20 mL) at 0° C., was added 1M LAH in THF (33.0 mL, 66.1 mmol) slowly over 15 min and the reaction mixture was allowed to warm to room temperature over 2 h. The reaction mixture was quenched with 1.5N HCl, concentrated under reduced pressure and then diluted with EtOAC (100 mL). The organic layer was washed with brine (3×40 mL), dried over anhydrous Na$_2$SO$_4$, filtered and concentrated in vacuo. The residue obtained was purified by silica gel chromatography (SiO$_2$, 20% EtOAc in hexane) to afford Preparation 3A (1.72 g, 8.26 mmol, 62.5% yield) as a sticky oil. $^1$H NMR (400 MHz, CHCl$_3$-d) δ ppm 6.50 (d, J=0.75 Hz, 1H) 6.35 (s, 1H) 3.61 (t, J=7.15 Hz, 2H) 2.47 (s, 3H) 2.21 (t, J=7.15 Hz, 2H) 2.18 (s, 3H) 1.56 (s, 6H).

Preparation 3B: 2-(4-(tert-Butyldimethylsilyloxy)-2-methylbutan-2-yl)-3,5-dimethylphenol (3B)

To a stirred solution of Preparation 3A (1.72 g, 8.26 mmol) in DMF (10 mL) at 0° C., was added tert-butylchlorodimethylsilane (1.493 g, 9.91 mmol) and imidazole (1.405 g, 20.64 mmol) and the reaction mixture was allowed to warm to room temperature for 3 h. The reaction mixture was concentrated under reduced pressure, diluted with EtOAC (20 mL), washed with brine (2×20 mL), and then dried over anhydrous Na$_2$SO$_4$ and concentrated in vacuo. The brown residue obtained was purified by silica gel chromatography (SiO$_2$, 30% EtOAc in hexane) to afford Preparation 3B (2.5 g, 7.75 mmol, 94% yield) as an off-white solid. $^1$H NMR (400 MHz, CHCl$_3$-d) δ ppm 6.48 (d, J=0.50 Hz, 1H) 6.40 (d, J=1.50 Hz, 1H) 5.53 (s, 1H) 3.59 (t, J=6.88 Hz, 2H) 2.45 (s, 3H) 2.18 (s, 3H) 2.11 (t, J=7.00 Hz, 2H) 1.55 (s, 6H) 0.87 (s, 9H) 0.03 (s, 6H).

Preparation 3C: Dibenzyl 2-(4-(tert-butyldimethylsilyloxy)-2-methylbutan-2-yl)-3,5-dimethylphenyl phosphate

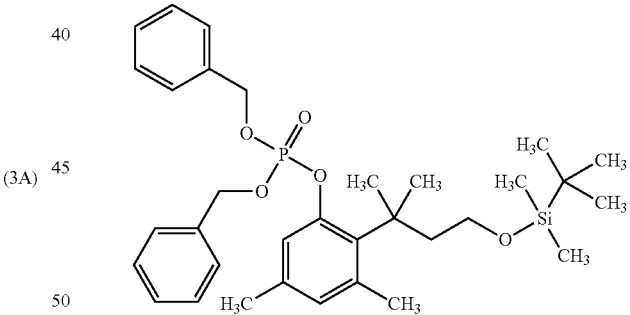

(3C)

To a stirred solution of Preparation 3B (0.6 g, 1.860 mmol) and potassium 2-methylpropan-2-olate (0.230 g, 2.046 mmol) in THF (6 mL), was added tetrabenzyl diphosphate (1.102 g, 2.046 mmol) and the reaction mixture was allowed to heated at 60° C. overnight. The reaction mixture was then concentrated under reduced pressure, diluted with EtOAC, and washed with brine (2×10 mL). The organic layer was dried over Na$_2$SO$_4$, filtered and concentrated in vacuo. The residue obtained was purified by silica gel chromatography (SiO$_2$, 20% EtOAc in hexane) to afford Preparation 3C (0.475 g, 0.815 mmol, 43.8% yield) as a pale yellow liquid. $^1$H NMR (400 MHz, CHCl$_3$-d) δ ppm 7.30-7.36 (m, 10H) 7.09-7.12 (m, 1H) 6.70-6.74 (m, 1H) 5.12 (d, J=8.28 Hz, 4H) 3.49 (t, J=7.40 Hz, 2H) 2.51 (s, 3H) 2.18 (s, 3H) 2.10 (t, J=7.40 Hz, 2H) 1.53 (s, 6H) 0.83-0.85 (m, 9H),) 0.03 (s, 6H).

Preparation 3D: 3-(2-(Bis(benzyloxy)phosphory-loxy)-4,6-dimethylphenyl)-3-methylbutanoic acid

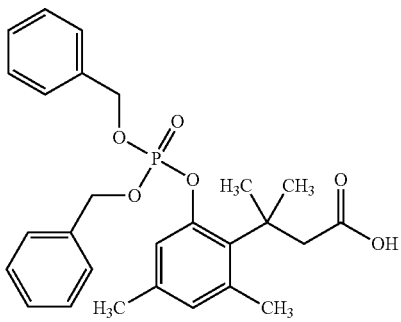

(3D)

To a stirred solution of Preparation 3C (0.288 g, 0.494 mmol) in acetone (10 mL) at 0° C., was added potassium iodide (0.328 g, 1.977 mmol) and the reaction mixture was stirred for 10 minutes. Chromium trioxide (1.35 M Jones reagent) (1.464 mL, 1.977 mmol) was then added slowly at 0° C. and the reaction mixture was allowed to warm to room temperature for 4 h. The reaction mixture was concentrated under reduced pressure, diluted with EtOAc (10 mL), washed with brine (3×20 mL), dried over anhydrous $Na_2SO_4$ and then concentrated in vacuo. The residue obtained was purified by silica gel chromatography ($SiO_2$, 30% EtOAc in hexane) to afford Preparation 3D (0.152 g, 0.315 mmol, 63.7% yield) as a pale yellow solid. $^1$H NMR (400 MHz, DMSO-$d_6$) δ ppm 11.78 (s, 1H) 7.35-7.40 (m, 9H) 6.93 (s, 1H) 6.75 (s, 1H) 5.15 (d, J=8.28 Hz, 4H) 2.80 (s, 2H) 2.49 (s, 3H) 2.12 (s, 3H) 1.52 (s, 6H).

Preparation 3E: ((S)-3-((2R,3S)-3-Carbamoyl-6,6,6-trifluoro-2-(3,3,3-trifluoropropyl)hexanamido)-2-oxo-5-phenyl-2,3-dihydro-1H-benzo[e][1,4]diaz-epin-1-yl)methyl 3-(2-((bis(benzyloxy)phosphoryl) oxy)-4,6-dimethylphenyl)-3-methylbutanoate

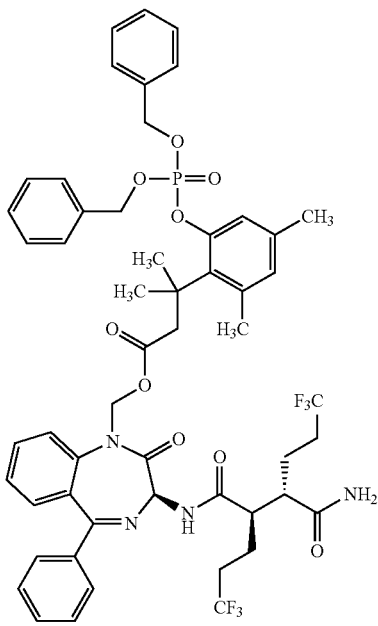

(3E)

To a stirred solution of Preparation 1A (69 mg, 0.115 mmol) in DCM (2 mL) at 0° C., was added triethylamine hydrochloride (23.64 mg, 0.172 mmol) and sulfuryl chloride (0.279 ml, 3.44 mmol) dropwise. The reaction mixture was allowed to warm to room temperature for 1 h. The reaction mixture was then concentrated under reduced pressure at room temperature under a nitrogen atmosphere, and taken immediately into the next step. The intermediate obtained above was dissolved in DMF (2 mL), and Preparation 3D (152 mg, 0.315 mmol), and cesium carbonate (187 mg, 0.573 mmol) were added at room temperature and the reaction mixture was stirred for 4 h. The reaction mixture was then concentrated under reduced pressure at room temperature, diluted with EtOAc (5 mL), and washed with brine (2×10 mL). The organic layer was dried ($Na_2SO_4$), filtered and then concentrated in vacuo. The residue obtained was purified by silica gel chromatography ($SiO_2$, 30% EtOAc in hexane) to afford Preparation 3E (100 mg, 0.096 mmol, 84% yield) as an off-white solid. HPLC RT: 2.330 min. (Column-Ascentis Express C8 (5×2.1 mm-2.7 µm), Mphase A: 2% ACN-98% $H_2O$-10 mM $NH_4COOH$, Mphase B: 98% ACN-2% $H_2O$-10 mM $NH_4COOH$, Flow=1 mL/min). MS(ES): m/z=1037 [M+H]$^+$.

Example 3

To a stirred solution of Preparation 3E (75 mg, 0.072 mmol) in ethanol (2 mL), was added 10% Pd/C (30 mg, 0.282 mmol) under a nitrogen atmosphere. The reaction mixture was then stirred under a hydrogen atmosphere for 20 minutes. The reaction mixture was filtered through a pad of CELITE® and the filtrate was concentrated under reduced pressure. The crude residue was purified by preparative reversed-phase HPLC (Inertsil ODS (4.6×250) mm, 5 micron, Mobile Phase A: 0.1% TFA in water: Acetonitrile (90:10), Mobile Phase B: methanol, Flow rate: 1 mL\min) Lyophilization of the appropriate fractions afforded 12.5 mg of Example 3 as an off-white solid. $^1$H NMR (400 MHz, DMSO-$d_6$) δ ppm 9.61 (d, J=7.78 Hz, 1H) 7.59-7.69 (m, 2H) 7.50-7.58 (m, 3H) 7.37-7.49 (m, 3H) 7.29-7.37 (m, 2H) 7.15 (s, 1H) 7.09 (d, J=8.28 Hz, 1H) 6.51 (s, 2H) 5.95 (d, J=10.54 Hz, 1H) 5.38 (d, J=7.78 Hz, 1H) 5.31 (d, J=10.29 Hz, 1H) 3.02 (d, J=15.81 Hz, 2H) 2.77-2.87 (m, 2H) 2.31 (s, 3H) 2.11-2.22 (m, 3H) 2.06 (s, 3H) 1.54-1.75 (m, 5H) 1.40 (s, 6H); HPLC:RT=11.331 min (SunFire C18 (4.6×150) mm, 3.5 micron Buffer: 0.05% TFA in water pH 2.5 adjusted with Ammonia Mobile Phase A:Buffer: Acetonitrile (95:5) Mobile Phase B:Acetonitrile:Buffer (95: 5) FLOW: 1 ml\min, monitored at 220 nm); MS(ES): m/z=857 [M+H]$^+$.

Example 4

((3S)-3-(((2R,3S)-3-Carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 2-methylalaninate

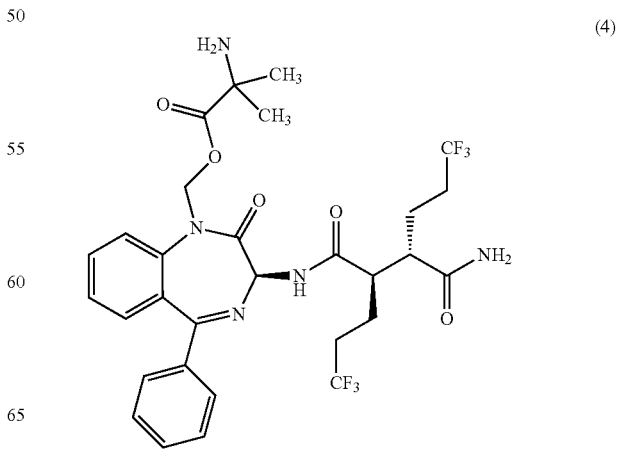

(4)

Preparation 4A: Chloromethyl-2-(tert-butoxycarbonylamino)-2-methylpropanoate

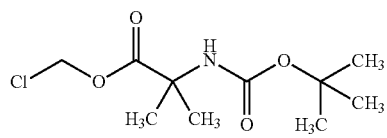

(4A)

To a stirred solution of 2-((tert-butoxycarbonyl)amino)-2-methylpropanoic acid (1 g, 4.92 mmol), sodium carbonate (2.61 g, 24.60 mmol) and tetrabutylammonium hydrogen sulfate (0.334 g, 0.984 mmol) in a mixture of DCM (10 mL) and water (5 mL) at 0° C., was added chloromethyl chlorosulfate (1.624 g, 9.84 mmol). The reaction mixture was allowed to warm to room temperature overnight. The mixture was diluted with DCM (10 mL), 10 mL water was added and the organic layer was separated, washed with brine (2×10 mL) and dried over anhydrous $Na_2SO_4$. The mixture was filtered and concentrated in vacuo and the residue obtained was purified by flash chromatography ($SiO_2$, 0-10% EtOAc in hexane) to afford Preparation 4A (0.8 g, 3.18 mmol, 64.6% yield) as an off-white solid: $^1$H NMR (400 MHz, chloroform-d) δ ppm 5.75 (s, 2H), 4.90 (br s., 1H), 1.51 (s, 6H), 1.43 (s, 9H).

Preparation 4B: Iodomethyl-2-(tert-butoxycarbonylamino)-2-methylpropanoate

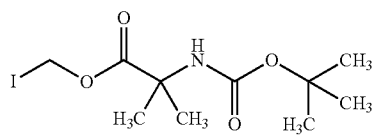

(4B)

To a stirred solution of Preparation 4A (0.2 g, 0.795 mmol) in acetone (2 mL), was added sodium iodide (0.476 g, 3.18 mmol). The reaction mixture was stirred at room temperature overnight. The mixture was diluted with EtOAc (10 mL), 15 mL of water was added and the organic layer was separated, washed with brine (2×10 mL) and dried over anhydrous $Na_2SO_4$. The mixture was filtered and concentrated in vacuo to afford Preparation 4B (0.21 g, 0.612 mmol, 77% yield) as a brown liquid. $^1$H NMR (400 MHz, $CHCl_3$-d) δ ppm 5.96 (s, 2H), 4.88 (br s., 1H), 1.47 (s, 6H), 1.44 (s, 9H).

Preparation 4C: ((S,Z)-3-((2R,3S)-3-Carbamoyl-6,6,6-trifluoro-2-(3,3,3-trifluoropropyl) hexanamido)-2-oxo-5-phenyl-2,3-dihydro-1H-benzo[e][1,4]diazepin-1-yl)methyl 2-(tert-butoxycarbonylamino)-2-methylpropanoate

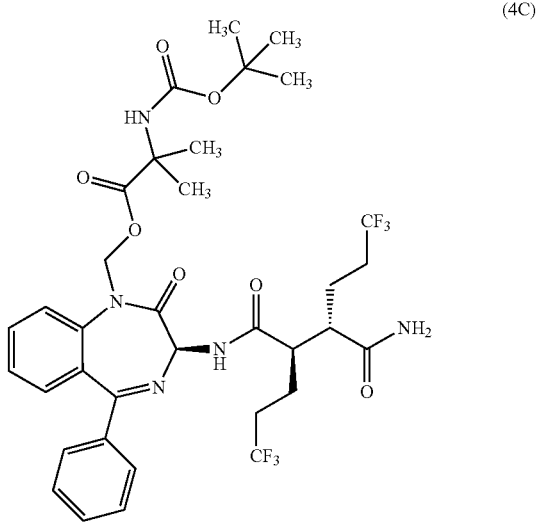 [SMILES: CC(C)(C)OC(=O)NC(C)(C)C(=O)OCN1C(=O)[C@@H](NC(=O)[C@H](CCC(F)(F)F)[C@H](CCC(F)(F)F)C(N)=O)N=C(c2ccccc2)c2ccccc21]

(4C)

To a mixture of Compound B (20 mg, 0.037 mmol) and cesium carbonate (24.02 mg, 0.074 mmol) in DMF (1 mL), was added a solution of Preparation 4B (63.3 mg, 0.184 mmol) in DMF (0.5 mL). The reaction mixture was stirred at room temperature overnight. Water (5 mL) was added to the reaction mixture, and the mixture was extracted with EtOAc (3×5 mL). The combined organic layers were dried over anhydrous $Na_2SO_4$, filtered and concentrated to dryness. The crude material was purified by preparative-TLC (60% EtOAc in hexane) to afford Preparation 4C (14 mg, 0.018 mmol, 50% yield) as an off-white solid. HPLC RT: 2.003 min (Column: ZORBAX® SB C18 (4.6×50) mm, 5 µm, Positive mode Mphase A: 10% MeOH-90% $H_2O$-0.1% TFA Mphase B: 90% MeOH-10% $H_2O$-0.1% TFA Flow: 5 ml/min). MS(ES): m/z=758 $[M+H]^+$.

Example 4

To a solution of Preparation 4C (28 mg, 0.037 mmol) in DCM (0.5 mL) at 0° C., was added 4M HCl in dioxane (1 mL, 0.111 mmol) dropwise. The mixture was allowed to warm to room temperature and stirred at 24° C. for 4 h. The reaction mixture was then concentrated to dryness. The yellow solid obtained was taken into a water/diethyl ether (4 mL, 1:1) mixture, where the desired compound was extracted into the water and impurities were washed off in the diethyl ether layer. The aqueous layer was lyophilized to obtain Example 4 (19 mg, 0.029 mmol, 78% yield)) as an off-white solid. $^1$H NMR (400 MHz, DMSO-$d_6$) δ ppm 9.63 (d, J=7.28 Hz, 1H) 8.45 (br. s., 3H) 7.74-7.84 (m, 2H) 7.67 (br. s., 1H) 7.54-7.61 (m, 3H) 7.43-7.52 (m, 3H) 7.38-7.42 (m, 1H) 7.16 (br. s., 1H) 6.17 (d, J=10.79 Hz, 1H) 5.83 (d, J=10.54 Hz, 1H) 5.43 (d, J=7.28 Hz, 1H) 2.77-2.87 (m, 1H) 2.15 (dd, J=19.07, 10.04 Hz, 4H) 1.52-1.76 (m, 5H) 1.43 (s, 2H) 1.31 (s, 3H) 1.27 (s, 3H). HPLC:RT=10.054 min (SunFire C18 (4.6×150) mm, 3.5 micron, Buffer: 0.05% TFA in water pH 2.5 Mobile Phase A: Buffer:Acetonitrile (95:5) Mobile Phase B:Acetonitrile: Buffer (95:5) FLOW: 1 mL\min, monitored at 220 nm); MS(ES): m/z=658 $[M+H]^+$.

Example 5

((3S)-3-(((2R,3S)-3-Carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl L-alaninate

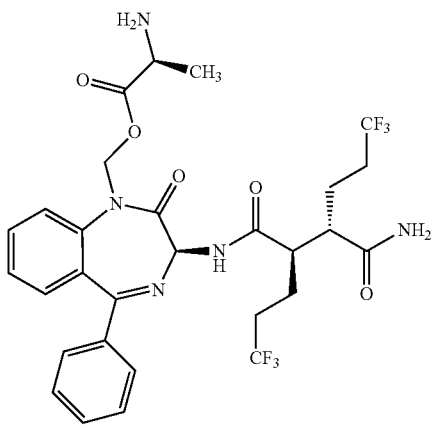

(5)

Preparation 5A: (S)-Chloromethyl 2-((tert-butoxycarbonyl)amino)propanoate

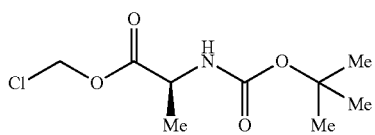

(5A)

To a vigorously stirred mixture of (S)-2-((tert-butoxycarbonyl)amino)propanoic acid (1 g, 5.29 mmol), tetrabutylammonium hydrogen sulfate (0.359 g, 1.057 mmol), and $Na_2CO_3$ (2.80 g, 26.4 mmol) in DCM 20 (mL) and water (20 mL) cooled in an ice/water bath was slowly added chloromethyl chlorosulfate (1.09 mL, 10.57 mmol) over a 4 min period. After stirring in ice/water bath for 30 min the cold bath was removed and the reaction allowed to stir at room temperature. After stirring 16 h at room temperature the reaction was diluted with water and extracted with DCM. The aqueous layer was back extracted with DCM and the combined organic layers were dried over $MgSO_4$, filtered and concentrated to afford Preparation 5A (1.64 g).

Preparation 5B: (S)—((S,Z)-3-((2R,3S)-3-Carbamoyl-6,6,6-trifluoro-2-(3,3,3-trifluoropropyl)hexanamido)-2-oxo-5-phenyl-2,3-dihydro-1H-benzo[e][1,4]diazepin-1-yl)methyl 2-(tert-butoxycarbonylamino)propanoate

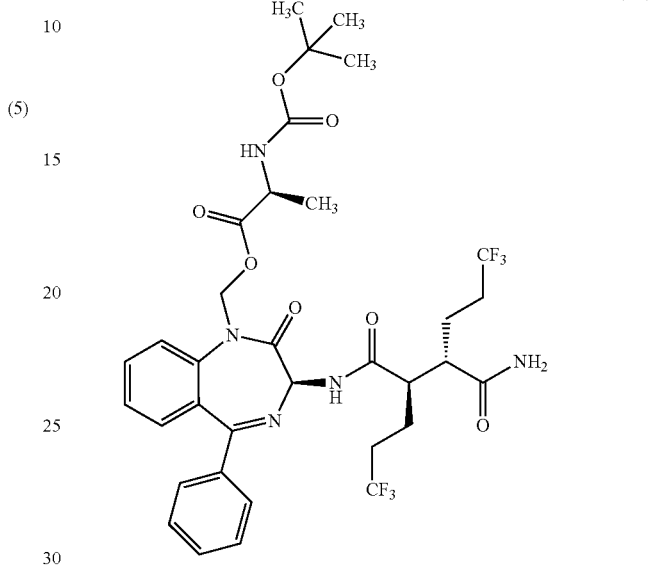

(5B)

A suspension of Compound B (50 mg, 0.092 mmol) and $K_2CO_3$ (38.2 mg, 0.277 mmol) in DMF (2 mL) was treated with Preparation 5A (54.8 mg, 0.230 mmol) and the reaction was stirred at room temperature overnight. The reaction was diluted with water (10 mL) and EtOAc (10 mL). The layers were separated and the organic layer was washed once with water, dried ($Na_2SO_4$), filtered and then concentrated to dryness. The product was dissolved in a small amount of DCM and purified by flash chromatography ($SiO_2$, 0% ethyl acetate/hexanes to 70% ethyl acetate/hexanes, 24 g column, 30 min gradient) to afford Preparation 5B (28 mg, 40.8%). HPLC RT=2.918 min (CHROMOLITH® SpeedROD, 5.0 um, 4.6 mm×50 mm, 10-90% aqueous methanol containing 0.1% TFA, 4 min gradient, monitored at 220 nm). MS(ES): m/z=744.5 $[M+H]^+$.

Example 5

A solution of Preparation 5B (19 mg, 0.026 mmol) in DCM (1 mL) was treated with 4N HCl in dioxane (0.064 mL, 0.255 mmol) and stirred at room temperature for 4 hours. The resulting suspension was concentrated to dryness. The crude reaction product was dissolved in a small amount of MeOH and purified by reversed phase HPLC (YMC ODS C18 5 μm 20×100 mm, 10-90% aqueous methanol containing 0.1% TFA, 20 mL/min, 20 min gradient, monitored at 220 nm). The product (retention time=12.838 minutes) was isolated and lyophilized to dryness to afford Example 5 (7.3 mg, 36.3%). HPLC RT=7.075 min (Xbridge Phenyl 3.5 μm, 3×150 mm, 10% 95/5 water/ACN with 0.05% TFA to 100% 5/95 water/ACN with 0.05% TFA, 15 minute gradient, flow rate=0.5 mL/min, monitored at 220 and 254 nm). MS(ES): m/z=644.4 $[M+H^+]$. $^1$H NMR (400 MHz, DMSO-$d_6$) δ 9.61 (d, J=7.3 Hz, 1H), 8.27 (br. s., 3H), 7.83-7.71 (m, 2H), 7.64 (br. s., 1H), 7.60-7.52 (m, 3H), 7.51-7.42 (m, 3H), 7.37 (d, J=7.3 Hz, 1H), 7.14 (s, 1H), 6.20 (d, J=10.6 Hz, 1H), 5.73 (d, J=10.6 Hz, 1H), 5.41 (d, J=7.3 Hz, 1H), 4.10 (br. s., 1H), 2.87-2.77 (m, 1H), 2.46-2.37 (m, 2H), 2.29-2.05 (m, 3H), 1.78-1.48 (m, 4H), 1.16 (d, J=7.3 Hz, 3H).

Example 6

((3S)-3-(((2R,3S)-3-Carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl L-valinate

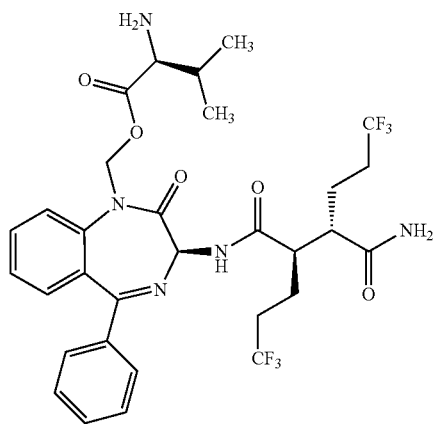

(6)

Preparation 6A: (S)-Chloromethyl 2-(tert-butoxycarbonylamino)-3-methylbutanoate

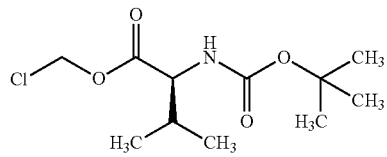

(6A)

To a vigorously stirred mixture of (S)-2-((tert-butoxycarbonyl)amino)-3-methylbutanoic acid (4 g, 18.41 mmol), tetrabutylammonium hydrogen sulfate (1.25 g, 3.68 mmol), and Na$_2$CO$_3$ (9.76 g, 92 mmol) in DCM (80 mL) and water (80 mL) cooled in an ice/water bath was slowly added chloromethyl chlorosulfate (3.8 mL, 36.8 mmol) over 4 min. After stirring in the ice/water bath for 30 min, the cold bath was removed and the reaction was allowed to stir at room temperature. After stirring 16 h at room temperature the reaction was diluted with water and extracted with DCM. The aqueous layer was back extracted with DCM and the combined organic layers were dried over MgSO$_4$, filtered and concentrated. The crude material (5.45 g) was used as is without purification.

Preparation 6B: (S)—((S,Z)-3-((2R,3S)-3-Carbamoyl-6,6,6-trifluoro-2-(3,3,3-trifluoropropyl)hexanamido)-2-oxo-5-phenyl-2,3-dihydro-1H-benzo[e][1,4]diazepin-1-yl)methyl 2-(tert-butoxycarbonylamino)-3-methylbutanoate

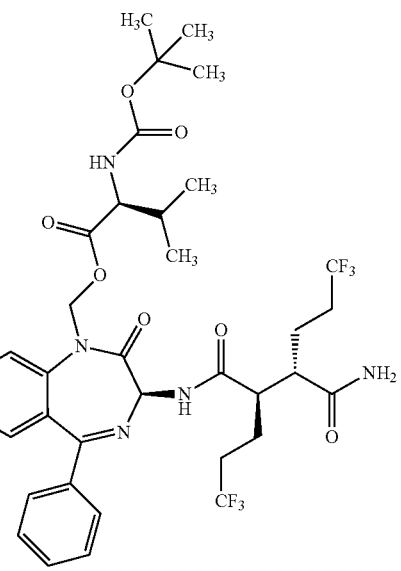

(6B)

A suspension of Compound B (50 mg, 0.092 mmol) and K$_2$CO$_3$ (38.2 mg, 0.277 mmol) in DMF (2 mL) was treated with Preparation 6A (61.2 mg, 0.230 mmol) and the reaction was stirred at room temperature overnight. After 18 h, additional Preparation 6A (61.2 mg, 0.230 mmol) and K$_2$CO$_3$ (38.2 mg, 0.277 mmol) were added and the reaction was again stirred overnight. The reaction was then diluted with water (10 mL) and EtOAc (10 mL). The layers were separated and the organic layer was washed once with water, dried (Na$_2$SO$_4$), filtered and then concentrated to dryness. The crude product was dissolved in a small amount of DCM and purified by flash chromatography (SiO$_2$, 0% ethyl acetate/hexanes to 70% ethyl acetate/hexanes, 24 g column, 30 min gradient) to afford Preparation 6B (19 mg, 26.7%). HPLC RT=3.128 min (CHROMOLITH® SpeedROD, 5.0 um, 4.6 mm×50 mm, 10-90% aqueous methanol containing 0.1% TFA, 4 min gradient, monitored at 220 nm). MS(ES): m/z=772.5 [M+H]$^+$.

Example 6

A solution of Preparation 6B (19 mg, 0.025 mmol) in DCM (1 mL) was treated with 4N HCl in dioxane (0.062 mL, 0.246 mmol) and stirred at room temperature for 4 hours. The resulting suspension was concentrated to dryness. The crude reaction product was dissolved in a small amount of MeOH and purified by reversed phase HPLC (YMC ODS C18 5 µm 20×100 mm, 10-90% aqueous methanol containing 0.1% TFA, 20 mL/min, 20 min gradient, monitored at 220 nm). The product (retention time=13.726 minutes) was isolated and lyophilized to dryness to afford Example 6 (7.3 mg, 35.9%). HPLC RT=7.333 min(Xbridge Phenyl 3.5 µm, 3×150 mm, 10% 95/5 water/ACN with 0.05% TFA to 100% 5/95 water/ACN with 0.05% TFA, 15 minute gradient, flow rate=0.5 mL/min, monitored at 220 and 254 nm). MS(ES): m/z=672.4 [M+H]⁺. ¹H NMR (400 MHz, DMSO-d₆) δ 9.64 (d, J=7.3 Hz, 1H), 8.34 (br. s., 3H), 7.81-7.74 (m, 2H), 7.65 (br. s., 1H), 7.61-7.53 (m, 4H), 7.51-7.42 (m, 4H), 7.41-7.37 (m, 1H), 7.13 (br. s., 1H), 6.27 (d, J=10.8 Hz, 1H), 5.65 (d, J=10.6 Hz, 1H), 5.40 (d, J=7.3 Hz, 1H), 3.96 (br. s., 1H), 2.84-2.76 (m, 1H), 2.48-2.39 (m, 2H), 2.30-2.06 (m, 4H), 2.04-1.92 (m, 1H), 1.74-1.46 (m, 4H), 0.80 (d, J=7.0 Hz, 3H), 0.76 (d, J=7.0 Hz, 3H).

Example 7

((3S)-3-(((2R,3S)-3-Carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 1-aminocyclopropanecarboxylate (7)

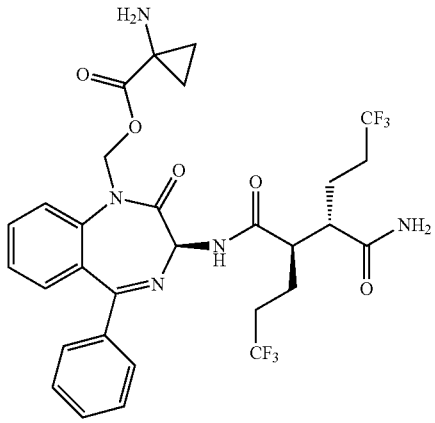

Preparation 7A: ((S)-3-((2R,3S)-3-Carbamoyl-6,6,6-trifluoro-2-(3,3,3-trifluoropropyl)hexanamido)-2-oxo-5-phenyl-2,3-dihydro-1H-benzo[e][1,4]diazepin-1-yl)methyl 1-((tert-butoxycarbonyl)amino)cyclopropanecarboxylate (7A)

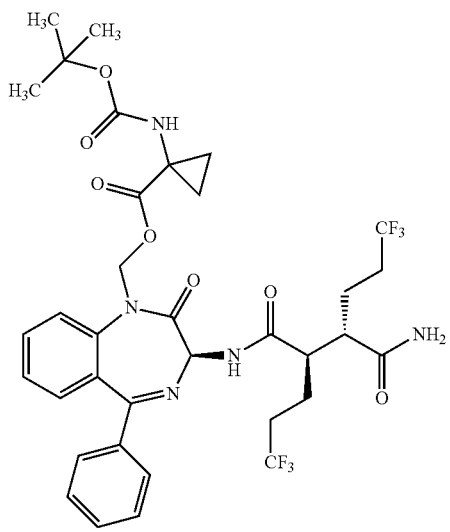

To a solution of Compound B (0.015 g, 0.028 mmol) in DMF (1 mL) was added K₂CO₃ (7.64 mg, 0.055 mmol), and the reaction mixture was stirred at room temperature under a nitrogen atmosphere for 10 min. Then chloromethyl 1-((tert-butoxycarbonyl)amino)cyclopropanecarboxylate (0.035 g, 0.138 mmol) in DMF was added and the mixture was stirred overnight at room temperature. Additional chloromethyl 1-((tert-butoxycarbonyl)amino)cyclopropanecarboxylate (0.035 g, 0.138 mmol) and K₂CO₃ (7.64 mg, 0.055 mmol) were added and the mixture was stirred at room temperature overnight. The crude mixture was diluted with EtOAc and washed with water (2×1 mL). The EtOAc layer was dried (Na₂SO₄), filtered and concentrated to dryness. The crude product was purified using preparative TLC (50% EtOAc/Petroleum ether) to afford Preparation 7A (12 mg). MS(ES): m/z=756 (M+H)⁺.

Example 7

To a solution of Preparation 7A (12 mg, 0.16 mmol) in DCM (0.5 mL) at −10° C. was added a 1M solution of HCl in dioxane (0.2 mL). The reaction mixture was stirred at −10° C. for 2 hours and then additional 1M HCl in dioxane (0.2 mL) was added at 0° C. After 1 hour, the reaction mixture was concentrated and purified by preparative reversed-phase HPLC (TFA/MeCN) to afford 5 mg of Example 7. ¹H NMR (400 MHz, DMSO-d₆) δ ppm 9.57 (d, J=7.03 Hz, 1H), 8.28-8.72 (m, 1H), 7.77 (d, J=3.51 Hz, 2H), 7.63-7.69 (m, 1H), 7.53-7.60 (m, 3H), 7.42-7.52 (m, 3H), 7.38 (s, 1H), 7.15 (br s, 1H), 6.09 (d, J=10.54 Hz, 1H), 5.82 (d, J=10.54 Hz, 1H), 5.42 (d, J=7.2 Hz, 1H), 2.79-2.98 (m, 2H), 2.06-2.29 (m, 3H), 1.47-1.82 (m, 5H), 1.06-1.30 (m, 5H); HPLC:RT=11.050 min (SunFire C18 (4.6×150) mm, 3.5 micron, Buffer: 0.05% TFA in water pH 2.5 adjusted with NH₃, Mobile Phase A: Buffer: Acetonitrile (95:5), Mobile Phase B: Acetonitrile:Buffer (95:5), Flow rate: 1 mL/min, monitored at 220 nm); MS(ES): m/z=656 [M+H]⁺.

Example 8

(2S,3R)—N-((2-Aminoethyl)sulfanyl)-N'-((3S)-2-oxo-5-phenyl-2,3-dihydro-1H-1,4-benzodiazepin-3-yl)-2,3-bis(3,3,3-trifluoropropyl)succinamide (8)

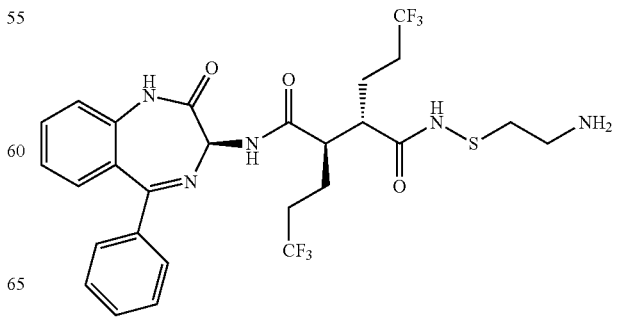

Preparation 8A: tert-Butyl (2-(((2S,3R)-6,6,6-trifluoro-3-(((S)-2-oxo-5-phenyl-2,3-dihydro-1H-benzo[e][1,4]diazepin-3-yl)carbamoyl)-2-(3,3,3-trifluoropropyl)hexanamido)thio)ethyl)carbamate

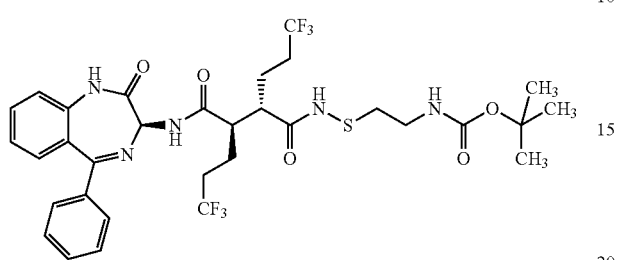

(8A)

A suspension of silver nitrate (23.49 mg, 0.138 mmol) in MeOH (1 mL) was treated with di-tert-butyl (disulfanediylbis(ethane-2,1-diyl))dicarbamate (48.7 mg, 0.138 mmol). The reaction mixture was stirred for 30 minutes and then Compound B (25 mg, 0.046 mmol) and TEA (0.019 mL, 0.138 mmol) were added, resulting in a light yellow solution. After 18 hours, the reaction mixture was concentrated in vacuo. The crude red oil was dissolved in a small amount of DCM and purified by flash chromatography (SiO$_2$, 0% to 50% EtOAc in hexanes) to afford tert-butyl (2-(((2S,3R)-6,6,6-trifluoro-3-(((S)-2-oxo-5-phenyl-2,3-dihydro-1H-benzo[e][1,4]diazepin-3-yl)carbamoyl)-2-(3,3,3-trifluoropropyl)hexanamido)thio)ethyl)carbamate. MS(ES): m/z=718 (M+H)$^+$.

Example 8

A solution of Preparation 8A (44 mg, 0.061 mmol) in DCM (2 mL) at 0° C. was treated with TFA (0.236 mL, 3.07 mmol). The reaction mixture was warmed to room temperature and left stirring for 4 h. The reaction mixture was then concentrated and the crude material was purified by preparative reversed-phase chromatography (Column: Symmetry C18 (300×19) mm, 7 micron, flow: 1 mL/min, Mobile Phase A: 0.1% TFA in water, Mobile Phase B: ACN) to afford Example 8 (19.6 mg, 0.032 mmol, 51.8% yield) as a white solid. $^1$H NMR (400 MHz, DMSO-d$_6$) δ ppm 10.87 (s, 1H), 9.58 (s, 1H), 9.47 (s, 1H), 7.87 (br s, 3H), 7.63-7.69 (m, 1H), 7.42-7.56 (m, 5H), 7.23-7.35 (m, 3H), 5.26 (d, J=7.28 Hz, 1H), 3.49-3.52 (m, 1H), 2.85-3.02 (m, 5H), 2.65-2.73 (m, 1H), 2.08-2.29 (m, 3H), 1.57-1.84 (m, 3H), 1.40-1.51 (m, 1H); HPLC:RT=11.765 min (Column: SunFire C18 (4.6×150) mm, 3.5 micron, Buffer: 0.05% TFA in water pH 2.5 adjusted with dilute NH$_3$, Mobile Phase A: Buffer:Acetonitrile (95:5), Mobile Phase B: Acetonitrile:Buffer (95:5), Flow rate: 1 ml\min, monitored at 220 nm); MS(ES): m/z=618 (M+H)$^+$.

Example 9

S-(((2S,3R)-6,6,6-Trifluoro-3-(((3S)-2-oxo-5-phenyl-2,3-dihydro-1H-1,4-benzodiazepin-3-yl)carbamoyl)-2-(3,3,3-trifluoropropyl)hexanoyl)amino)-L-cysteine (9)

Example 9A: (2R,2'R)-Di-tert-butyl 3,3'-disulfanediylbis(2-((tert-butoxycarbonyl)amino)propanoate (9A)

A solution of (2R,2'R)-di-tert-butyl 3,3'-disulfanediylbis(2-aminopropanoate) (1.9 g, 5.39 mmol) in THF (10.78 ml) was treated with triethylamine (1.502 ml, 10.78 mmol) and stirred at room temperature for 10 min. Di-tert-butyl dicarbonate (2.59 g, 11.86 mmol) was added, and the mixture was stirred at room temperature for 12 h. The reaction mixture was diluted with ethyl acetate (100 mL) and washed with 1N HCl (2×50 mL). The organic layer was then washed with H$_2$O (50 mL) and brine (50 mL). The organic layer was then dried over anhydrous Na$_2$SO$_4$, filtered and concentrated to give a pale yellow oil which was further purified by flash chromatography (SiO$_2$, ethyl acetate/hexanes) to afford (2R,2'R)-di-tert-butyl 3,3'-disulfanediylbis(2-((tert-butoxycarbonyl)amino)propanoate) (1.4 g, 2.53 mmol, 47.0% yield) as a white solid. $^1$H NMR (400 MHz, CHCl$_3$-d) δ ppm 5.33 (br s, 2H), 4.46 (br s, 2H), 3.08-3.27 (m, 4H), 1.48 (s, 18H), 1.45 (s, 18H).

Example 9B: (R)-tert-Butyl 2-((tert-butoxycarbonyl)amino)-3-(((2S,3R)-6,6,6-trifluoro-3-((((S)-2-oxo-5-phenyl-2,3-dihydro-1H-benzo[e][1,4]diazepin-3-yl)carbamoyl)-2-(3,3,3-trifluoropropyl)hexanamido)thio)propanoate

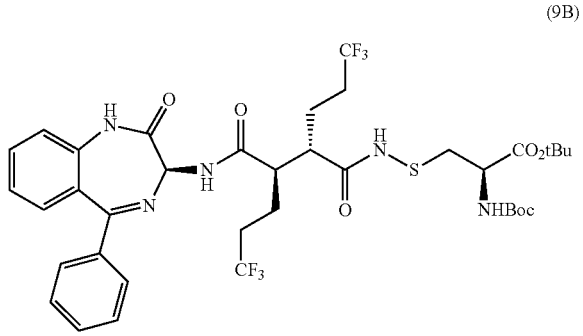 [SMILES: CC(C)(C)OC(=O)N[C@@H](CSNC(=O)[C@@H](CCC(F)(F)F)[C@@H](CCC(F)(F)F)C(=O)N[C@H]1N=C(c2ccccc2)c2ccccc2NC1=O)C(=O)OC(C)(C)C]

(9B)

A slight suspension of silver nitrate (31.3 mg, 0.184 mmol) in methanol (5 mL) was treated with Preparation 9A (102 mg, 0.184 mmol). After stirring for 30 min, Compound B (25 mg, 0.046 mmol) and TEA (25.7 μL, 0.184 mmol) were added. The resulting mixture was stirred at room temperature overnight. The reaction was then concentrated to dryness. The crude product was dissolved in a small amount of DCM and purified by flash chromatography (SiO$_2$, 0% ethyl acetate/hexanes to 60% ethyl acetate/hexanes, 24 g column, 40 min gradient) to afford Preparation 9B (19 mg, 50.4%). HPLC RT=3.356 min (CHROMOLITH® SpeedROD, 5.0 um, 4.6 mm×50 mm, 10-90% aqueous methanol containing 0.1% TFA, 4 min gradient, monitored at 220 nm). MS(ES): m/z=818.5 [M+H$^+$]. $^1$H NMR (400 MHz, chloroform-d) δ 8.40 (br. s., 1H), 7.78 (s, 1H), 7.64 (d, J=7.7 Hz, 1H), 7.60-7.50 (m, 3H), 7.49-7.32 (m, 4H), 7.26-7.15 (m, 2H), 5.57 (d, J=7.7 Hz, 1H), 5.45 (d, J=8.4 Hz, 1H), 4.26 (br. s., 1H), 3.45 (d, J=14.3 Hz, 1H), 2.88-2.79 (m, 1H), 2.72 (br. s., 1H), 2.45-2.07 (m, 6H), 2.03-1.91 (m, 2H), 1.82-1.67 (m, 1H), 1.47 (d, J=5.1 Hz, 18H).

Example 9

A solution of Preparation 9B (18 mg, 0.022 mmol) in DCM (3 mL) was treated with TFA (0.3 mL, 3.89 mmol) and stirred at room temperature for 8 hours and then concentrated to dryness. The crude reaction product was dissolved in a small amount of MeOH and purified by reversed phase HPLC (YMC ODS C18 5 μm 20×100 mm, 10-90% aqueous methanol containing 0.1% TFA, 20 mL/min, 20 min gradient, monitored at 220 nm). The product (retention time=14.069 minutes) was isolated and lyophilized to dryness to afford Example 9 (10.3 mg, 60.3%). HPLC RT=8.928 min (SunFire C18 3.5 μm, 3×150 mm, 10% 95/5 water/ACN with 0.05% TFA to 100% 5/95 water/ACN with 0.05% TFA, 15 minute gradient, flow rate=0.5 mL/min, monitored at 220 and 254 nm). MS(ES): m/z=622.4 [M+H$^+$]. $^1$H NMR (400 MHz, DMSO-d$_6$) δ 10.86 (s, 1H), 9.60 (s, 1H), 9.56 (d, J=7.5 Hz, 1H), 8.42 (br. s., 3H), 7.65 (t, J=7.0 Hz, 1H), 7.57-7.39 (m, 5H), 7.32 (d, J=7.5 Hz, 2H), 7.28-7.22 (m, 1H), 5.25 (d, J=7.5 Hz, 1H), 3.98 (br. s., 1H), 3.27 (dd, J=14.9, 3.6 Hz, 1H), 3.02 (dd, J=15.1, 8.9 Hz, 1H), 2.94-2.84 (m, 1H), 2.77-2.64 (m, 1H), 2.28-2.10 (m, 2H), 1.85-1.54 (m, 2H), 1.45 (d, J=9.2 Hz, 1H).

Example 10

(2S,3R)—N-((Isobutylamino)methyl)-N'-((3S)-1-methyl-2-oxo-5-phenyl-2,3-dihydro-1H-1,4-benzodiazepin-3-yl)-2,3-bis(3,3,3-trifluoropropyl)succinamide

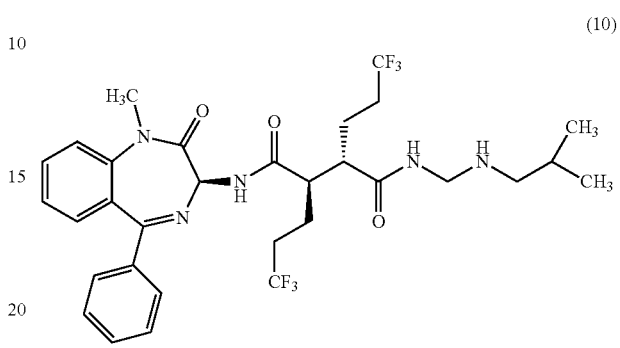

(10)

2-Methylpropan-1-amine (0.714 mL, 7.19 mmol) was dissolved in an ethanolic solution (1.5 mL) of Compound A (0.020 g, 0.036 mmol). Then formaldehyde (0.535 mL, 7.19 mmol) was added slowly with constant stirring. The reaction mixture was heated at 75° C. for 48 h. The reaction mixture was then concentrated to dryness, diluted with water (5 mL) and extracted with EtOAc. The combined organic layers were dried with Na$_2$SO$_4$, filtered and concentrated to dryness. The crude material was purified by preparative reversed-phase HPLC (Column: Symmetry C18 (300×19) mm 7μ, Mobile Phase A: 0.1% TFA in water: Acetonitrile (90:10), Mobile Phase B: Acetonitrile, Flow rate: 15 ml/min) to afford Example 10 (0.0082 g, 35.6%): $^1$H NMR (400 MHz, DMSO-d$_6$) δ ppm 9.53 (d, J=7.2 Hz, 1H), 8.28-8.48 (m, 1H), 7.69-7.80 (m, 2H), 7.51-7.59 (m, 3H), 7.42-7.49 (m, 2H), 7.32-7.38 (m, 2H), 5.32 (d, J=7.53 Hz, 1H), 4.12-4.20 (m, 1H), 3.90-4.09 (m, 1H), 3.40 (s, 1H), 3.18-3.22 (m, 1H), 2.82-2.90 (m, 1H), 2.29 (d, J=6.8 Hz, 1H), 2.09 (m, 6H), 1.57-1.80 (m, 4H), 0.85 (d, J=4.0 Hz, 6H); HPLC:RT=15.808 min (Column: XBridge Phenyl (4.6×150) mm, 3.5 micron, Buffer: 0.05% TFA in water pH 2.5 adjusted with dilute NH$_3$, Mobile Phase A: Buffer: Acetonitrile (95:5), Mobile Phase B: Acetonitrile:Buffer (95:5), Flow rate: 1 ml\min, monitored at 220 nm); MS(ES): m/z=642 (M+H)$^+$.

Example 11

(2S,3R)—N-((2-Aminoethyl)sulfanyl)-N'-((3S)-1-methyl-2-oxo-5-phenyl-2,3-dihydro-1H-1,4-benzodiazepin-3-yl)-2,3-bis(3,3,3-trifluoropropyl)succinamide

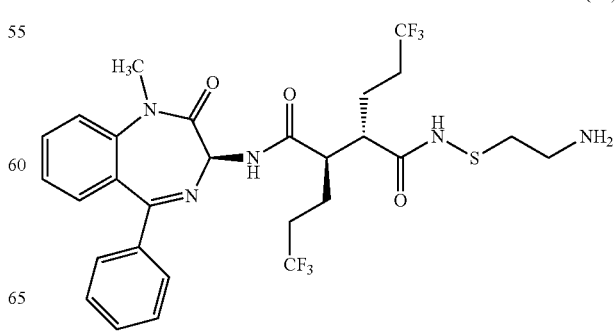

(11)

Preparation 11A: tert-Butyl 2-((2S,3R)-6,6,6-trifluoro-3-((S,Z)-1-methyl-2-oxo-5-phenyl-2,3-dihydro-1H-benzo[e][1,4]diazepin-3-ylcarbamoyl)-2-(3,3,3-trifluoropropyl)hexanamidothio)ethylcarbamate

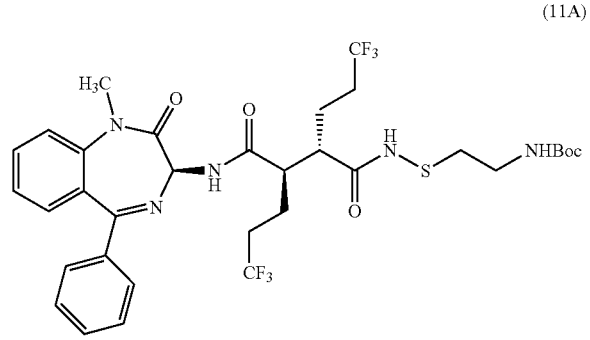 [SMILES: CN1C(=O)[C@@H](NC(=O)[C@H](CCC(F)(F)F)[C@H](CCC(F)(F)F)C(=O)NSCCNC(=O)OC(C)(C)C)N=C(c2ccccc2)c2ccccc21]

(11A)

To a suspension of silver nitrate (0.018 g, 0.108 mmol) in MeOH (1.2 mL), was added di-tert-butyl (disulfanediylbis(ethane-2,1-diyl))dicarbamate (0.038 g, 0.108 mmol) and the mixture was stirred at 24° C. for 20 min. Then Compound A (0.020 g, 0.036 mmol) was added to the reaction mixture followed by the addition of TEA (0.015 mL, 0.108 mmol). After stirring for 4 h, the mixture was concentrated in vacuo. The crude was partially purified by column chromatography (SiO$_2$, 0-10% EtOAc in hexane) to remove silver related impurities. The crude material was further purified by preparative TLC (0-50% EtOAc/hexane) to afford Preparation 11A (0.028 g, 108%): HPLC:RT=18.653 min (Column: XBridge Phenyl (4.6×150) mm, 3.5 micron, Buffer: 0.05% TFA in water pH 2.5 adjusted with dilute NH$_3$, Mobile Phase A: Buffer:Acetonitrile (95:5), Mobile Phase B: Acetonitrile: Buffer (95:5), Flow rate: 1 ml\min, monitored at 220 nm); MS(ES): m/z=732 (M+H)$^+$.

Example 11

To a solution of Preparation 11A (0.028 g, 0.038 mmol) in DCM (1.2 ml) at 0° C., was added TFA (0.147 ml, 1.913 mmol) dropwise and the mixture was allowed to warm to room temperature. After stirring for 24 h, the reaction mixture was concentrated to dryness. The crude material was purified by preparative reversed-phase HPLC (Column: Inertsil ODS (250×19 mm) 5μ, Mobile Phase A: 0.1% TFA in water, Mobile Phase B: Acetonitrile, Flow rate: 16 ml/min) to afford Example 11 (0.008 g, 33.1%): $^1$H NMR (400 MHz, DMSO-d$_6$) δ ppm 9.60 (d, J=7.28 Hz, 1H), 9.46 (s, 1H), 7.85 (br. s., 3H), 7.67-7.78 (m, 2H), 7.52-7.59 (m, 3H), 7.43-7.50 (m, 2H), 7.32-7.38 (m, 2H), 5.31 (d, J=7.28 Hz, 1H), 3.40 (s, 3H), 2.84-3.02 (m, 5H), 2.63-2.72 (m, 1H), 2.07-2.35 (m, 4H), 1.56-1.84 (m, 3H), 1.39-1.49 (m, 1H). HPLC:RT=7.700 min (Column: SunFire C18 (4.6×150) mm, 3.5 micron, Buffer: 0.05% TFA in water pH 2.5 adjusted with dilute NH$_3$, Mobile Phase A: Buffer: Acetonitrile (95:5), Mobile Phase B: Acetonitrile: Buffer (95:5), Flow rate: 1 ml\min, monitored at 220 nm); MS(ES): m/z=632 (M+H)$^+$.

Example 12

S-(((2S,3R)-6,6,6-Trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoyl)amino)-L-cysteine

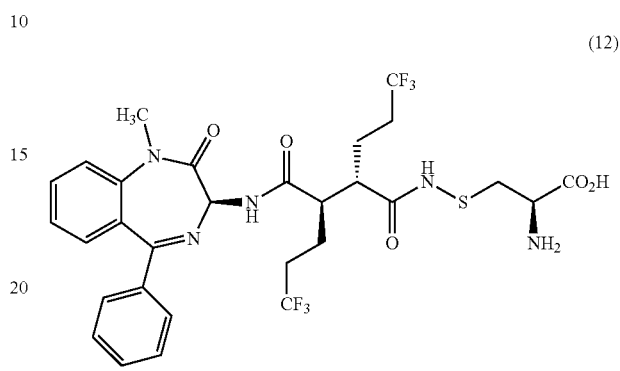

(12)

Preparation 12A: S-tert-Butyl 2-((tert-butoxycarbonyl)amino)-3-(((2S,3R)-6,6,6-trifluoro-3-(((S)-1-methyl-2-oxo-5-phenyl-2,3-dihydro-1H-benzo[e][1,4]diazepin-3-yl)carbamoyl)-2-(3,3,3-trifluoropropyl)hexanamido)thio)propanoate

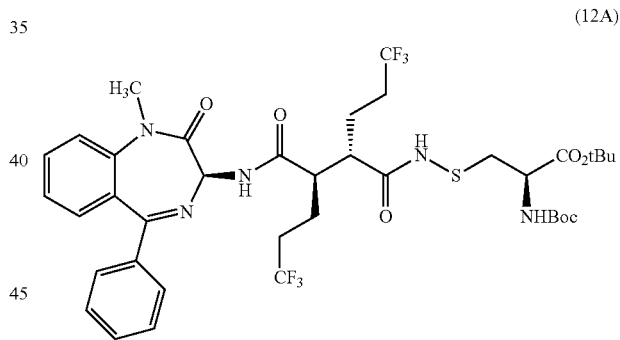

(12A)

A suspension of silver nitrate (8.39 mg, 0.049 mmol) in MeOH (1 mL) was treated with Preparation 9A (37.2 mg, 0.067 mmol). The mixture was stirred for 30 minutes and then treated with Compound A (20 mg, 0.036 mmol) and TEA (10.02 μl, 0.072 mmol). After 2 hours, an additional 1.5 eq. of Preparation 9A, 1.1 eq. of the silver nitrate, and 1.6 eq. of TEA were added and the reaction mixture was allowed to stir at room temperature overnight. The mixture was then concentrated in vacuo. The crude oil was dissolved in a small amount of DCM and purified by flash chromatography (SiO$_2$, 0% to 50% EtOAc in hexanes) to afford Preparation 12A (30.6 mg, 0.037 mmol, 82% yield) as a light brown oil. MS(ES): m/z=832 [M+H]$^+$.

Example 12

A solution of Preparation 12A (15 mg, 0.018 mmol) in DCM (1 mL) at 0° C. was treated with TFA (0.069 mL, 0.902 mmol). The reaction mixture was stirred for 30 min at 0° C. and then warmed to room temperature for 3.5 h. Additional TFA (0.069 mL, 0.902 mmol) was added at 0° C. and the reaction mixture was stirred for another 2 h at room temperature. Additional TFA (0.069 mL, 0.902 mmol) was added at 0° C. and the reaction mixture was stirred at room temperature overnight. The resulting solution was concentrated and the residue was purified by preparative reversed-phase HPLC (Column: Inertsil ODS (250×19 mm) 5µ, Mobile Phase A: 0.1% TFA in water, Mobile Phase B: Acetonitrile, Flow rate: 16 ml/min) to afford Example 12 (3 mg, 4.44 µmol, 24.62% yield) as a white powder after lyophilization. $^1$H NMR (400 MHz, DMSO-$d_6$) δ ppm 9.57-9.64 (m, 2H), 8.41 (br s, 3H), 7.66-7.79 (m, 2H), 7.52-7.59 (m, 3H), 7.44-7.48 (m, 2H), 7.32-7.39 (m, 2H), 5.31 (d, 7.2 Hz, 1H), 3.97 (br s, 1H), 2.98-3.06 (m, 2H), 2.52-2.68 (m, 5H), 2.11-2.28 (m, 3H), 1.72-1.83 (m, 1H), 1.56-1.71 (m, 2H), 1.43 (t, J=12.30 Hz, 1H), 1.15-1.26 (m, 1H); HPLC:RT=7.893 min (SunFire C18 (4.6×150) mm, 3.5 micron, Buffer: 0.05% TFA in water pH 2.5 adjusted with $NH_3$, Mobile Phase A: Buffer:Acetonitrile (95:5), Mobile Phase B: Acetonitrile:Buffer (95:5), Flow rate: 1 mL/min, monitored at 220 nm); MS(ES): m/z=676 $[M+H]^+$.

Example 13

(2S,3R)—N-((2-(Dimethylamino)ethyl)sulfanyl)-N'-((3S)-1-methyl-2-oxo-5-phenyl-2,3-dihydro-1H-1,4-benzodiazepin-3-yl)-2,3-bis(3,3,3-trifluoropropyl) succinamide (13)

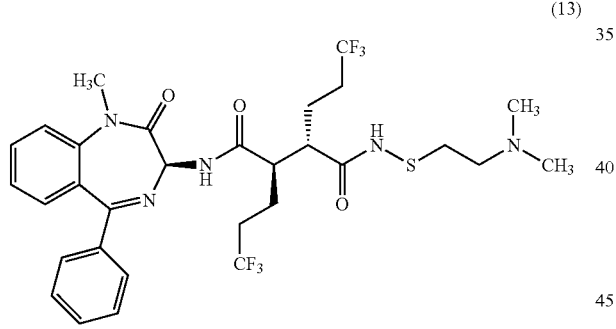

To a suspension of silver nitrate (0.183 g, 1.078 mmol) in MeOH (1.2 mL), was added 2,2'-disulfanediylbis(N,N-dimethylethanamine) (0.112 g, 0.539 mmol) and the mixture was stirred at 24° C. for 20 min. Then Compound A (0.020 g, 0.036 mmol) was added to the reaction mixture followed by the addition of TEA (0.025 mL, 0.180 mmol). After stirring at room temperature for 24 h, the mixture was concentrated in vacuo to dryness. The crude material was partially purified by column chromatography ($SiO_2$, 0-10% EtOAc in hexane) to remove metallic impurities. It was further purified by preparative reversed-phase HPLC (Column: Symmetry C18 (300×19) mm 7µ, Mobile Phase A: 0.1% TFA in water, Mobile Phase B: Acetonitrile, Flow rate: 15 ml/min) to afford Example 13 (0.0042 g, 17.72%): $^1$H NMR (400 MHz, DMSO-$d_6$) δ ppm 9.60 (d, J=7.53 Hz, 1H), 9.45 (s, 1H), 9.15 (br s, 1H), 7.67-7.78 (m, 2H), 7.52-7.59 (m, 3H), 7.44-7.50 (m, 2H), 7.33-7.38 (m, 2H), 5.30 (d, J=7.28 Hz, 1H), 3.38-3.44 (m, 5H), 3.19-3.27 (m, 6H), 2.87-2.96 (m, 2H), 2.65-2.69 (m, 4H), 2.31-2.35 (m, 2H), 1.42-1.71 (m, 4H); HPLC: RT=9.168 min (Column: XBridge Phenyl (4.6×150) mm, 3.5 micron, Buffer: 0.05% TFA in water pH 2.5 adjusted with dil.$NH_3$, Mobile Phase A: Buffer: Acetonitrile (95:5), Mobile Phase B: Acetonitrile:Buffer (95:5), Flow rate: 1 ml\min, monitored at 220 nm); MS(ES): m/z=660 $(M+H)^+$.

Example 14

Methyl S-(((2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoyl)amino)-L-cysteinate (14)

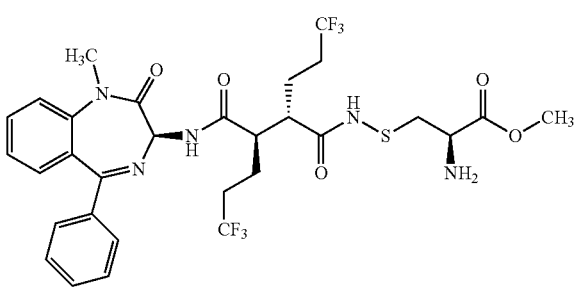

Preparation 14A: Methyl 2-(tert-butoxycarbonylamino)-3-((2S,3R)-6,6,6-trifluoro-3-((S,Z)-1-methyl-2-oxo-5-phenyl-2,3-dihydro-1H-benzo[e][1,4] diazepin-3-ylcarbamoyl)-2-(3,3,3-trifluoropropyl) hexanamidothio)propanoate (14A)

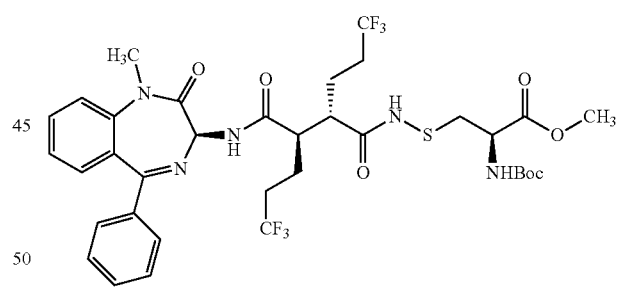

A suspension of silver nitrate (22.89 mg, 0.135 mmol) in MeOH (1 mL) was treated with (2R,2'R)-dimethyl 3,3'-disulfanediylbis(2-((tert-butoxycarbonyl)amino)propanoate) (63.2 mg, 0.135 mmol). After stirring for 30 minutes, Compound A (25 mg, 0.045 mmol) and TEA (0.019 mL, 0.135 mmol) were added resulting in a light yellow solution. The reaction mixture was stirred at room temperature for 4 h and then an additional 3 eq. of the disulfide, 3 eq. of silver nitrate, and 3 eq. of TEA were added. After stirring for 40 h, the reaction mixture was concentrated in vacuo. The crude material was dissolved in a small amount of DCM and purified by flash chromatography ($SiO_2$, 0% to 50% EtOAc in hexanes) to afford Preparation 14A as an off-white solid. MS(ES): m/z=790 $[M+H]^+$.

Example 14

A solution of Preparation 14A (56 mg, 0.071 mmol) in DCM (2 mL) at 0° C. was treated with TFA (0.273 mL, 3.55 mmol). The reaction mixture was warmed to room temperature and stirred for 6 h. The reaction mixture was then concentrated and purified by Prep-HPLC (Column: XTERRA® RP18 (250×4.6) mm, 5 micron, flow: 1 mL/min, Mobile Phase A: 0.1% TFA in water/ACN (90/10), Mobile Phase B: ACN) to afford Example 14 (19.6 mg, 39.3%) as a white solid. $^1$H NMR (400 MHz, DMSO-$d_6$) δ ppm 9.56-9.64 (m, 2H), 8.54 (br. s., 3H), 7.66-7.78 (m, 2H), 7.52-7.60 (m, 3H), 7.47 (m, 2H), 7.32-7.39 (m, 2H), 5.32 (d, J=7.28 Hz, 1H), 4.14 (dd, J=8.28, 4.27 Hz, 1H), 3.76 (s, 3H), 3.31-3.41 (m, 3H) 3.26 (dd, J=15.31, 4.27 Hz, 2H), 3.04 (dd, J=15.06, 8.53 Hz, 1H), 2.91 (td, J=10.42, 3.26 Hz, 1H), 2.63-2.73 (m, 1H), 2.11-2.28 (m, 3H), 1.72-1.84 (m, 1H), 1.54-1.71 (m, 2H), 1.38-1.48 (m, 1H); MS(ES): m/z=690 [M+H]$^+$.

Example 15

(2R,3S)—N-((3S)-1-Methyl-2-oxo-5-phenyl-2,3-dihydro-1H-1,4-benzodiazepin-3-yl)-N'-((4-methyl-1-piperazinyl)methyl)-2,3-bis(3,3,3-trifluoropropyl)succinamide

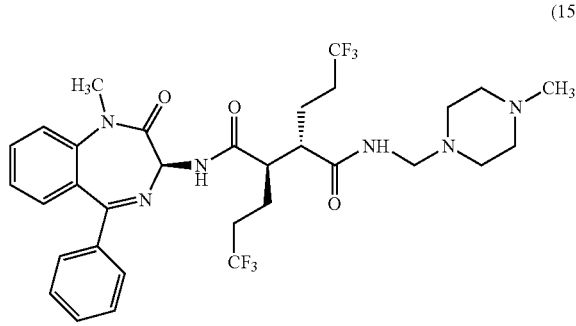

(15)

To a solution of Compound A (0.020 g, 0.036 mmol) in ethanol (1.2 mL), was added 1-methylpiperazine (0.720 g, 7.19 mmol) followed by the addition of formaldehyde (0.198 mL, 7.19 mmol) and the mixture was heated at 75° C. for 18 h. The mixture was concentrated under reduced pressure, diluted with water (7 mL) and extracted with EtOAc (2×5 mL). The combined organic layers were dried over anhydrous Na$_2$SO$_4$, filtered and concentrated to dryness. The crude material was purified by preparative reversed-phase HPLC (Column: Symmetry C18 (300×19) mm 7μ, Mobile Phase A: 0.1% TFA in water: Acetonitrile (90:10), Mobile Phase B: Acetonitrile, Flow rate: 15 ml/min) to afford Example 15 (0.0156 g, 64.9%): $^1$H NMR (400 MHz, DMSO-$d_6$) δ ppm 9.57 (d, J=7.28 Hz, 1H), 9.4 (br s, 1H), 8.61 (t, J=5.65 Hz, 1H), 7.66-7.78 (m, 2H), 7.52-7.59 (m, 3H), 7.43-7.49 (m, 2H), 7.33-7.37 (m, 2H), 5.31 (d, J=7.28 Hz, 1H), 4.03-4.10 (m, 1H), 3.93-4.01 (m, 1H), 3.40 (s, 3H), 2.82-3.01 (m, 6H), 2.78 (s, 3H), 2.62-2.74 (m, 1H), 2.08-2.31 (m, 4H), 1.48-1.80 (m, 4H); HPLC:RT=7.233 min (Column: SunFire C18 (4.6×150) mm, 3.5 micron, Buffer: 0.05% TFA in water pH 2.5 adjusted with dil.NH$_3$, Mobile Phase A: Buffer: Acetonitrile (95:5), Mobile Phase B: Acetonitrile: Buffer (95:5), Flow rate: 1 ml\min, monitored at 220 nm); MS(ES): m/z=669 (M+H)$^+$.

Example 16

(2R,3S)—N-((3S)-1-Methyl-2-oxo-5-phenyl-2,3-dihydro-1H-1,4-benzodiazepin-3-yl)-N'-(1-piperidinylmethyl)-2,3-bis(3,3,3-trifluoropropyl)succinamide

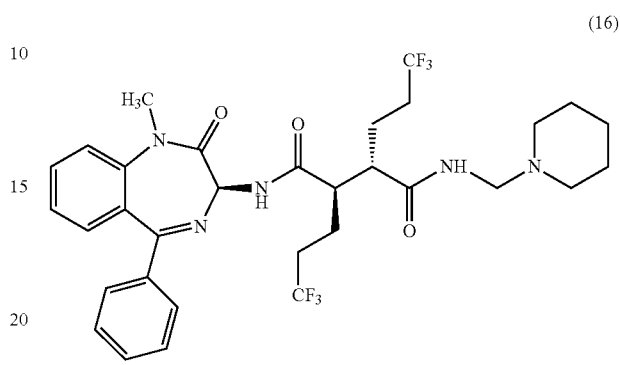

(16)

Compound A (0.020 g, 0.036 mmol) was dissolved in a solution of piperidine (0.712 mL, 7.19 mmol) and formaldehyde (0.535 mL, 7.19 mmol) and was stirred at 24° C. for 18 h. The mixture was concentrated under reduced pressure, diluted with water (7 ml) and extracted with EtOAc (2×5 mL). The combined organic layers were dried over anhydrous Na$_2$SO$_4$, filtered and concentrated to dryness. The crude material was purified by preparative reversed-phase HPLC (Column: Symmetry C18 (300×19) mm 7μ, Mobile Phase A: 0.1% TFA in water: Acetonitrile (90:10), Mobile Phase B: Acetonitrile, Flow rate: 15 ml/min) to afford Example 16 (0.0129 g, 54.9%): $^1$H NMR (400 MHz, DMSO-$d_6$) δ ppm 9.60 (d, J=7.28 Hz, 1H), 9.45 (br s, 1H), 9.37 (t, J=6.65 Hz, 1H), 7.67-7.78 (m, 2H), 7.52-7.59 (m, 3H), 7.44-7.50 (m, 2H), 7.32-7.38 (m, 2H), 5.32 (d, J=7.28 Hz, 1H), 4.39-4.53 (m, 2H), 3.40 (s, 3H), 2.98-3.06 (m, 3H), 2.92 (td, J=10.35, 3.39 Hz, 2H), 2.64 (td, J=9.98, 3.64 Hz, 2H), 2.13-2.34 (m, 4H), 1.52-1.86 (m, 7H), 1.22-1.40 (m, 2H); HPLC:RT=7.527 min (Column: SunFire C18 (4.6×150) mm, 3.5 micron SC/862, Buffer: 0.05% TFA in water pH 2.5 adjusted with dilute NH$_3$, Mobile Phase A: Buffer: Acetonitrile (95:5), Mobile Phase B: Acetonitrile:Buffer (95:5), Flow rate: 1 ml\min, monitored at 220 nm); MS(ES): m/z=654 (M+H)$^+$.

Example 17

(2S,3R)—N-((4-Amino-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide

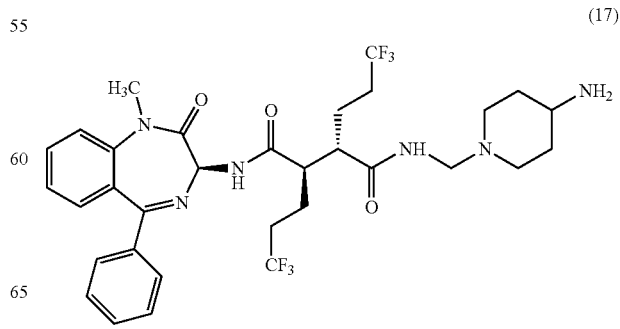

(17)

Example 17A: tert-Butyl 1-(((2S,3R)-6,6,6-trifluoro-3-(((S,Z)-1-methyl-2-oxo-5-phenyl-2,3-dihydro-1H-benzo[e][1,4]diazepin-3-ylcarbamoyl)-2-(3,3,3-trifluoropropyl) hexanamido)methyl)piperidin-4-ylcarbamate (17A)

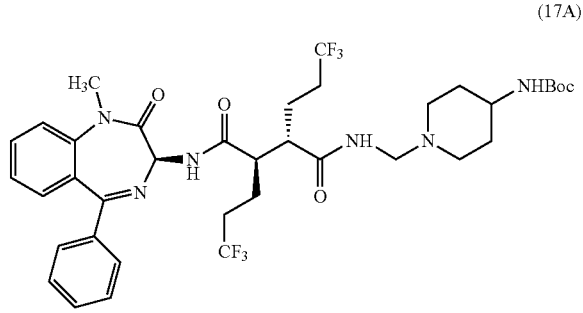 [SMILES: CN1C(=O)[C@@H](NC(=O)[C@H](CCC(F)(F)F)[C@H](CCC(F)(F)F)C(=O)NCN2CCC(NC(=O)OC(C)(C)C)CC2)N=C(c2ccccc2)c2ccccc21]

To a solution of Compound A (0.020 g, 0.036 mmol) in ethanol (1.0 mL), was added tert-butyl piperidin-4-ylcarbamate (1.440 g, 7.19 mmol) followed by the addition of formaldehyde (0.535 mL, 7.19 mmol) and the mixture was heated at 75° C. for 18 h. The mixture was concentrated under reduced pressure, diluted with water (7 mL) and extracted with EtOAc (2×5 mL). The combined organic layers were dried over anhydrous Na$_2$SO$_4$, filtered and concentrated to dryness. The crude material was purified by preparative-TLC (0-50% EtOAc/hexane) to afford Preparation 17A: (0.036 g, 129%): MS(ES): m/z=769 (M+H)$^+$.

Example 17

To a solution of Preparation 17A (0.036 g, 0.047 mmol) in DCM (2 mL) at 0° C., was added TFA (0.361 mL, 4.68 mmol) dropwise and the mixture was warmed to room temperature. After 4 h, the reaction mixture was concentrated to dryness. The crude material was purified by preparative reversed-phase HPLC (Column: Symmetry C18 (300×19) mm 7μ, Mobile Phase A: 0.1% TFA in water, Mobile Phase B: Acetonitrile, Flow rate: 15 ml/min) to afford Example 17 (0.009 g, 28.7%): $^1$H NMR (400 MHz, DMSO-d$_6$) δ ppm 9.59 (d, J=7.28 Hz, 1H), 7.95 (br s, 3H), 7.68-7.78 (m, 2H), 7.53-7.59 (m, 3H), 7.44-7.49 (m, 2H), 7.33-7.38 (m, 2H), 5.32 (d, J=7.53 Hz, 1H), 4.20-4.59 (m, 2H), 3.40 (s, 3H), 2.89-2.95 (m, 2H), 2.66-2.69 (m, 1H), 2.15-2.30 (m, 4H), 2.01 (br s, 2H), 1.47-1.74 (m, 9H) 1.36-1.46 (m, 1H); HPLC:RT=6.447 min (Column: SunFire C18 (4.6×150) mm, 3.5 micron, Buffer: 0.05% TFA in water pH 2.5 adjusted with dilute NH$_3$, Mobile Phase A: Buffer: Acetonitrile (95:5), Mobile Phase B: Acetonitrile: Buffer (95:5), Flow rate: 1 ml\min, monitored at 220 nm); MS(ES): m/z=669 (M+H)$^+$.

Example 18

(2S,3R)—N-((4-(Dimethylamino)-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (18)

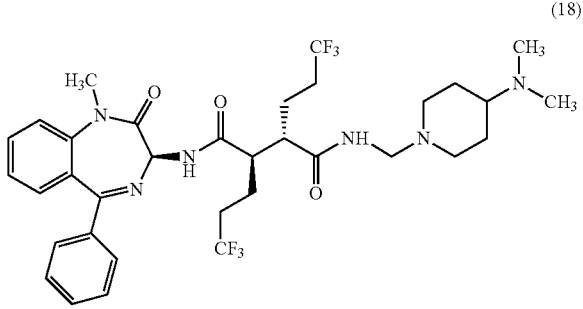 [SMILES: CN1C(=O)[C@@H](NC(=O)[C@H](CCC(F)(F)F)[C@H](CCC(F)(F)F)C(=O)NCN2CCC(N(C)C)CC2)N=C(c2ccccc2)c2ccccc21]

To a solution of Compound A (0.020 g, 0.036 mmol) in ethanol (1.2 mL), was added N,N-dimethylpiperidin-4-amine (0.922 g, 7.19 mmol) followed by the addition of formaldehyde (0.535 mL, 7.19 mmol) and the mixture was heated at 75° C. for 18 h. The mixture was concentrated under reduced pressure, diluted with water (7 mL) and extracted with EtOAc (2×5 mL). The combined organic layers were dried with Na$_2$SO$_4$, filtered and concentrated to dryness. The crude material was purified by preparative reversed-phase HPLC (Column: Symmetry C18 (300×19) mm 7μ, Mobile Phase A: 0.1% TFA in water: Acetonitrile (90:10), Mobile Phase B: Acetonitrile, Flow rate: 15 ml/min) to afford Example 18 (0.0195 g, 78%): $^1$H NMR (400 MHz, DMSO-d$_6$) δ ppm 9.75 (br s, 1H), 9.59 (d, J=7.28 Hz, 1H), 7.67-7.79 (m, 1H), 7.53-7.59 (m, 3H), 7.43-7.50 (m, 2H), 7.32-7.38 (m, 2H), 5.32 (d, J=7.53 Hz, 1H), 4.33 (br s, 2H), 3.40 (s, 3H), 2.90 (t, J=10.54 Hz, 2H), 2.60-2.77 (m, 9H), 2.07-2.31 (m, 6H), 1.50-1.84 (m, 8H). HPLC:RT=7.854 min (Column: XBridge Phenyl (4.6×150) mm, 3.5 micron, Buffer: 0.05% TFA in water pH 2.5 adjusted with dilute NH$_3$, Mobile Phase A: Buffer: Acetonitrile (95:5), Mobile Phase B: Acetonitrile:Buffer (95:5), Flow rate: 1 ml\min, monitored at 220 nm); MS(ES): m/z=697 (M+H)$^+$.

Example 19

(2S,3R)—N-((4-Hydroxy-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (19)

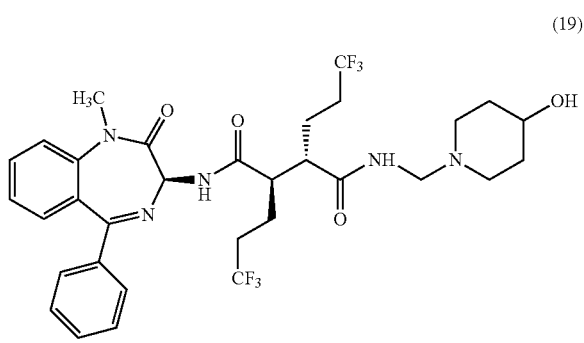 [SMILES: CN1C(=O)[C@@H](NC(=O)[C@H](CCC(F)(F)F)[C@H](CCC(F)(F)F)C(=O)NCN2CCC(O)CC2)N=C(c2ccccc2)c2ccccc21]

Compound A (0.020 g, 0.036 mmol) was dissolved in a solution of piperidin-4-ol (0.727 g, 7.19 mmol) and formaldehyde (0.535 mL, 7.19 mmol) in MeOH (1.2 mL) and heated at 75° C. for 18 h. The mixture was concentrated, diluted with water (7 mL) and extracted with EtOAc (2×5 mL). The combined organic layers were dried over anhydrous Na$_2$SO$_4$, filtered and concentrated to dryness. The crude material was purified by preparative reversed-phase HPLC (Column: Inertsil ODS-3 (250×20) mm 5μ, Mobile Phase A: 0.1% TFA in water, Mobile Phase B: Acetonitrile, Flow rate: 14 ml/min) to afford Example 19 (0.019 g, 79%): $^1$H NMR (400 MHz, DMSO-d$_6$) δ ppm 9.61 (d, J=7.28 Hz, 1H), 9.38 (dd, J=13.18, 6.65 Hz, 2H), 7.72-7.79 (m, 1H), 7.67-7.71 (m, 1H), 7.52-7.59 (m, 3H), 7.44-7.50 (m, 2H), 7.33-7.39 (m, 2H), 5.32 (d, J=7.28 Hz, 1H), 4.42-4.55 (m, 2H), 3.93 (br s, 1H), 3.40 (s, 3H), 3.33 (d, J=8.53 Hz, 1H), 3.05-3.22 (m, 3H), 2.87-2.96 (m, 2H), 2.60-2.69 (m, 1H), 2.14-2.35 (m, 3H), 1.72-1.99 (m, 4H), 1.50-1.72 (m, 5H). HPLC:RT=7.381 min (Column: SunFire C18 (4.6×150) mm, 3.5 micron, Buffer: 0.05% TFA in water pH 2.5 adjusted with dilute NH$_3$, Mobile Phase A: Buffer: Acetonitrile (95:5), Mobile Phase B: Acetonitrile: Buffer (95:5), Flow rate: 1 ml\min, monitored at 220 nm); MS(ES): m/z=670 (M+H)$^+$.

Example 20

(2S,3R)—N-((3-Hydroxy-1-pyrrolidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide

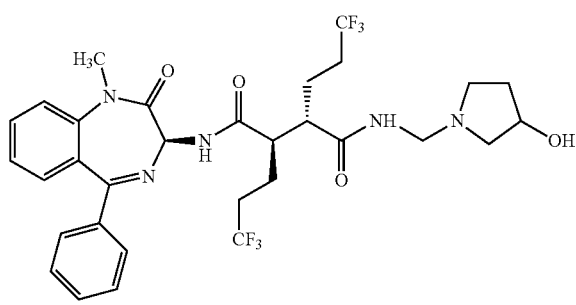

(20)

Compound A (0.020 g, 0.036 mmol) was dissolved in a solution of pyrrolidin-3-ol (0.626 g, 7.19 mmol) and formaldehyde (0.535 mL, 7.19 mmol) in MeOH (1.0 mL). Then the reaction mixture was heated at 75° C. for 18 h. The mixture was then concentrated under reduced pressure, diluted with water (7 mL) and extracted with EtOAc (2×5 mL). The combined organic layers were dried over anhydrous $Na_2SO_4$, filtered and concentrated to dryness. The crude material was purified by preparative reversed-phase HPLC (Column: SunFire C18 (150×19) mm 5μ, Mobile Phase A: 0.1% TFA in water, Mobile Phase B: Acetonitrile, Flow rate: 14 ml/min) to afford Example 20 (0.0185 g, 79%): $^1$H NMR (400 MHz, DMSO-$d_6$) δ ppm 9.61 (d, J=7.28 Hz, 1H), 9.40 (br s, 1H), 7.68-7.79 (m, 2H), 7.53-7.60 (m, 3H), 7.44-7.50 (m, 2H), 7.34-7.38 (m, 2H), 5.45 (br s, 1H), 5.32 (d, J=7.53 Hz, 1H), 4.39-4.62 (m, 3H), 3.40 (s, 3H), 3.03-3.31 (m, 4H), 2.92 (t, J=9.41 Hz, 1H), 2.62 (br s, 1H), 2.10-2.32 (m, 4H), 1.73-2.00 (m, 3H), 1.51-1.72 (m, 3H). HPLC:RT=8.532 min (Column: XBridge Phenyl (4.6×150) mm, 3.5 micron, Buffer: 0.05% TFA in water pH 2.5 adjusted with dilute $NH_3$, Mobile Phase A: Buffer: Acetonitrile (95:5), Mobile Phase B: Acetonitrile: Buffer (95:5), Flow rate: 1 ml\min, monitored at 220 nm); MS(ES): m/z=656 (M+H)$^+$.

Example 21

(2S,3R)—N-((3-(Dimethylamino)-1-pyrrolidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide

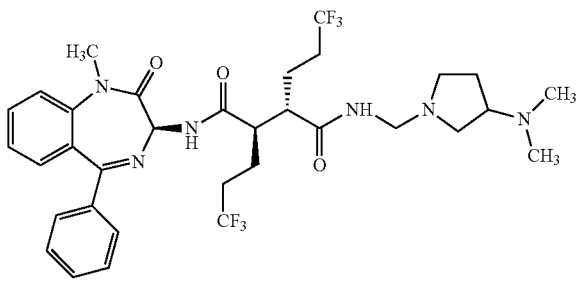

(21)

Compound A (0.020 g, 0.036 mmol) was dissolved in a solution of N,N-dimethylpyrrolidin-3-amine (0.821 g, 7.19 mmol) and formaldehyde (0.535 mL, 7.19 mmol) in MeOH (1.2 mL). The reaction mixture was heated at 75° C. for 18 h. The mixture was concentrated, diluted with water (7 mL) and extracted with EtOAc (2×5 mL). The combined organic layers were dried over anhydrous $Na_2SO_4$, filtered and concentrated to dryness. The crude material was purified by preparative reversed-phase HPLC (Column: Symmetry C18 (250×20 mm), Mobile Phase A: 0.1% TFA in water: Acetonitrile (90:10), Mobile Phase B: Acetonitrile, Flow rate: 15 ml/min) to afford Example 21 (0.019 g, 77%): $^1$H NMR (400 MHz, DMSO-$d_6$) δ ppm 9.57 (d, J=7.28 Hz, 1H), 8.65 (br s, 1H), 7.72-7.78 (m, 1H), 7.67-7.71 (m, 1H), 7.52-7.59 (m, 3H), 7.44-7.50 (m, 2H), 7.33-7.38 (m, 2H), 5.31 (d, J=7.53 Hz, 1H), 4.00-4.22 (m, 2H), 3.40 (s, 3H), 2.77-2.91 (m, 6H), 2.73 (br s, 7H), 2.11-2.28 (m, 4H), 1.94 (d, J=7.03 Hz, 1H), 1.51-1.80 (m, 5H). HPLC:RT=8.287 min (Column: XBridge Phenyl (4.6×150) mm, 3.5 micron, Buffer: 0.05% TFA in water pH 2.5 adjusted with dilute $NH_3$, Mobile Phase A: Buffer: Acetonitrile (95:5), Mobile Phase B: Acetonitrile:Buffer (95:5), Flow rate: 1 mL\min, monitored at 220 nm); MS(ES): m/z=683 (M+H)$^+$.

Example 22

(2R,3S)—N-((3S)-1-Methyl-2-oxo-5-phenyl-2,3-dihydro-1H-1,4-benzodiazepin-3-yl)-N'-(1-pyrrolidinylmethyl)-2,3-bis(3,3,3-trifluoropropyl)succinamide

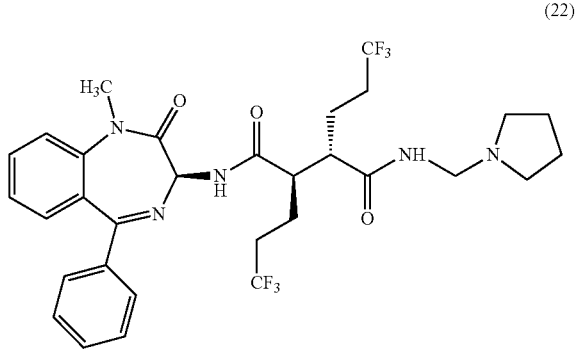 [SMILES: CN1C(=O)[C@@H](NC(=O)[C@H](CCC(F)(F)F)[C@H](CCC(F)(F)F)C(=O)NCN2CCCC2)N=C(c2ccccc2)c2ccccc21]

(22)

Compound A (0.020 g, 0.036 mmol) was dissolved in a solution of formaldehyde (0.535 mL, 7.19 mmol) and pyrrolidine (0.595 mL, 7.19 mmol) in MeOH (1.2 mL). The mixture was stirred at room temperature for 18 h. The mixture was then concentrated to dryness, diluted with water (7 mL) and extracted with EtOAc (2×5 mL). The combined organic layers were dried over anhydrous $Na_2SO_4$, filtered and concentrated to dryness. The crude material was purified by preparative reversed-phase HPLC (Column: SunFire C18 (150×20) mm 5μ, Mobile Phase A: 10 mM $NH_4OAc$ in water: Acetonitrile (90:10), Mobile Phase B: Acetonitrile, Flow rate: 14 ml/min) to afford Example 16 (0.0182 g, 79%): $^1$H NMR (400 MHz, DMSO-$d_6$) δ ppm 9.55 (d, J=7.53 Hz, 1H), 8.51 (t, J=6.02 Hz, 1H), 7.67-7.77 (m, 2H), 7.52-7.59 (m, 3H), 7.43-7.49 (m, 2H), 7.33-7.37 (m, 2H), 5.31 (d, J=7.28 Hz, 1H), 4.13 (dd, J=12.42, 6.40 Hz, 1H), 3.95 (dd, J=12.55, 5.52 Hz, 1H), 3.40 (s, 3H), 2.81-2.89 (m, 1H), 2.06-2.30 (m, 8H), 1.54-1.68 (m, 9H). HPLC:RT=14.937 min (Column: XBridge Phenyl (4.6×150) mm, 3.5 micron, Buffer: 0.05% TFA in water pH 2.5 adjusted with dilute $NH_3$, Mobile Phase A: Buffer:Acetonitrile (95:5), Mobile Phase B: Acetonitrile: Buffer (95:5), Flow rate: 1 ml\min, monitored at 220 nm); MS(ES): m/z=640 (M+H)$^+$.

BIOLOGICAL ASSAYS

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1×glutamine/penicillin/streptomycin and 10% Fetal Bovine serum, were transiently transfected in a T175 Flask ($4.5 \times 10^6$ cells/flask) using the Monster Transfection Kit (Minis #MIR2906) according to manufacturers specifications. Table 1 denotes respective DNA quantity for the transfections.

TABLE 1

|  | DNA (µg) | CBF1 (µg) | Vector (µg) | Total DNA (µg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of $5 \times 10^3$ cells/well in 95 µL assay media (DMEM (high glucose with HEPES), 1× glutamine/penicillin/streptomycin, 0.0125% BSA, 1× non-essential amino acids). Assay media (5 µL) containing test compounds in final concentrations ranging from 5 µM to $8.4 \times 10^{-5}$ µM (3 fold serial dilutions) were added to the cells and the cell plates were then incubated for 18 hours at 37° C. and 5% $CO_2$. Control wells contained DMSO vehicle (total counts) or 0.5 µM of an in-house small molecule inhibitor (background counts). Duplicates were used for each sample. Luciferase activity was measured after a 20-minute incubation with 50 µl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100× [1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 2 below lists the Notch 1 and Notch 3 $IC_{50}$ values for Compound A and Compound B measured in the Notch-CBF1 Transactivation Assay hereinabove. The results in Table 2 were rounded to 2 digits.

TABLE 2

| Compound | Notch 1 ($IC_{50}$, nM) | Notch 3 ($IC_{50}$, nM) |
|---|---|---|
| Compound A | 1.6 | 3.4 |
| Compound B | 1.7 | 3.3 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining) In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 3.

TABLE 3

| Metabolic Stability - Result Interpretation Guidelines | | | | | |
|---|---|---|---|---|---|
| CYP-Mediated | Percent Remaining after 10 minutes | | | | |
| Clearance | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Table 4 below lists the CYP-mediated metabolic stability for Compound A and Compound B measured in the human and mouse metabolic stability assays. The results in Table 4 were rounded to 2 digits. In the liver microsome assays, a value of 0% remaining indicated complete CYP-mediated metabolism of a test compound, and a value of 100% indicated no detectable CYP-mediated metabolism of a test compound. Compound A and B had metabolic stability values of 97% and 88% remaining for human liver microsomes (HLM), respectively; and 91% and 86% remaining for mouse liver microsomes (MsLM), respectively.

TABLE 4

| Compound | 0.5 µM HLM (% Remaining) | 0.5 µM MsLM (% Remaining) |
|---|---|---|
| Compound A | 97 | 91 |
| Compound B | 88 | 86 |

Methods and Materials
Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 µl of liver microsome suspension, protein concentration of 1.1 mg/ml in 100 mM $NaP_i$, pH 7.4, 5 mM $MgCl_2$ buffer, was pre-warmed at 37° C.

2. 1.7 µl of 50 µM compound (98.6% ACN, 1.4% DMSO) was added to the same tube and pre-incubated at 37° C. for 5 minutes.

3. The reaction was initiated by the addition of 17 µl of pre-warmed 10 mM NADPH solution in 100 mM $NaP_i$, pH 7.4.

The reaction components were mixed well, and 75 µl of the reaction mixture was immediately transferred into 150 µl quench/stop solution (zero-time point, $T_0$). Reactions were incubated at 37° C. for 10 minutes and then an additional 75 µl aliquot was transferred into 150 µl quench solution. Acetonitrile containing 100 µM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 5

Metabolic Stability Assay - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl2 | 5.0 mM |
| 37° C. Incubation time | 0 minutes and 10 minutes |
| Quench/Stop Solution (ACN + 100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-$H_2O$. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 6

Metabolic Stability - Structural Integrity Gradient

| Gradient Time (min) | A % | B % |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 7

Metabolic Stability - Sample Analysis Gradient

| Gradient Time (min) | A % (or C %) | B % (or D %) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10 minute}$ samples to those from the $T_{0 minute}$ samples for each compound.

Quality Control

A set of three compounds was tested along with the test compound in each assay plate. Data was accepted and uploaded only if the results for these control compounds fall into the expected ranges shown below.

TABLE 8

Metabolic Stability Assay - Control Compound Values by Microsome Species

| Com- pound | Average Percent Remaining ± SD | | | | |
|---|---|---|---|---|---|
| | Human | Rat | Mouse | Dog | Monkey |
| Nefazo- done | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carba- mezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al., 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45-minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table.

TABLE 9

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD-Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 µl of liver microsome suspension, protein concentration of 1.1 mg/ml in 100 mM $NaP_i$, pH 7.4, 5 mM $MgCl_2$ buffer, was pre-warmed at 37° C.

2. 5 µl of 50 µM compound (98.6% ACN, 1.4% DMSO) was added to the same tube and pre-incubated at 37° C. for 5 minutes.

3. The reaction was initiated by the addition of 50 µl of pre-warmed 10 mM NADPH solution in 100 mM $NaP_i$, pH 7.4.

Reaction components were mixed well, and 65 µl were immediately transferred into 130 µl quench/stop solution (zero-time point, $T_0$). Reactions were incubated at 37° C. for 5, 10, 15, 30 and 45 minutes and at each time-point a 65 µl aliquot was transferred into 130 µl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for LC/MS-MS analysis to determine the percent of parent compound that was remaining in the mixture.

TABLE 10

Metabolic Stability Half-Life Assays - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 µM DMN) | 130 µl |
| Sample of Reaction | 65 µl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Human Tumor Xenograft Models in Mice

All rodents were obtained from Harlan Sprague Dawley Co. (Indianapolis, Ind.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain (Table 11) using tumor fragments obtained from donor mice.

TABLE 11

Histological types and Host Mouse Strain/Gender Requirement for the Propagation of Various Human Tumor Xenografts in Mice

| Tumor Type | Histology | Mouse Strain | Sex |
|---|---|---|---|
| TALL-1 | T-ALL | NOD-SCID | female |
| MDA-MB-468 | Breast carcinoma | NOD-SCID | female |
| MDA-MB-157 | Breast carcinoma | NOD-SCID | female |
| PAT-70 | Pancreatic carcinoma | NOD-SCID | female |
| PAT-78 | Non-small cell lung carcinoma | NOD-SCID | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

Tumor weight=(length×width)÷2

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e., TGI≥50%) or log cell kill of 0.5 or greater (LCK≥0.5) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

In in vitro studies, all agents were dissolved in 100% DMSO and serially diluted in media/10% fetal bovine serum. For administration of Notch inhibitors to rodents, two different excipients were used: [1] 94% Labrafil/5% ETOH/1% TW80 or [2] ETOH/TPGS/PEG300 (10:10:80). Notch inhibitors were typically administered orally on a schedule of QD×15, 10 day-on-2 day-off, although other schedules had also been evaluated and shown to be efficacious. For example, dosing regimen consisting of QD×12, 4 day-on-3 day-off was shown to be equally efficacious as QD×15, 10 day-on-2 day-off.

In Vivo Antitumor Activity

Compound A demonstrates broad-spectrum antineoplastic activity against a wide array of human cancer xenografts grown in mice. Significant antitumor activity was demonstrated in 16 human cancer xenografts, including human T-cell acute lymphoblastic leukemia, breast carcinoma, pancreatic carcinoma, ovarian carcinoma, glioblastoma, non-small cell lung carcinoma, colon carcinoma, osteogenic sarcoma, and neuroblastoma (Table 12).

TABLE 12

| Tumor | Histology | Antitumor Activity (% TGI)[a] |
|---|---|---|
| TALL1 | T-Cell acute lymphoblastic leukemia | 112 |
| Pat-24 | pancreatic cancer | 111 |
| BT-474 | HER2+ breast cancer | 96 |
| Pat-26 | pancreatic cancer | 93 |
| MDA-MB468 | TN breast cancer | 91 |
| Pat-50 | ovarian cancer | 91 |
| Pat-34 | ovarian cancer | 89 |
| U-87 | glioblastoma multiforme (GBM) | 82 |
| MDA-MB157 | TN breast cancer | 81 |
| Calu-6 | Non small cell lung cancer | 81 |
| HCT116 | colon cancer | 75 |
| G292 | osteogenic sarcoma | 75 |
| Pat-21/Abx R | TN breast cancer (abx R) | 73 |
| MCF7 | estrogen-dependent breast cancer | 73 |
| SK-N-AS | neuroblastoma | 67 |
| MCF7i | estrogen-independent breast cancer | 63 |

[a]All treatments were PO, QDx15, 10 day-on-2 day-off, at dosages ranging from 5-10 mg/kg/adm.

TABLE 13

| Cell proliferation $IC_{50}$ (nM) | Compound A |
|---|---|
| TALL-1 leukemia | 3.9 |
| MDA-MB-468 breast cancer | 3.8 |

Thermodynamic Equilibrium Aqueous Solubility Assay

Standards Preparation: The calibration standard was prepared by accurately weighing 0.5-0.7 mg of sample in 5 ml of methanol. If the material was not fully soluble in methanol, other solvents such as DMSO or mixed solvents were used.

Test Sample Preparation: An excess amount of powder prodrug was equilibrated with 1 mL of buffer (50 mM potassium phosphate, pH 6.5 and 50 mM sodium acetate, pH 4.0) in a 2 mL glass vial. The solution was sonicated and vortexed for ~30 seconds. The vials were shaken at 300 rpm at room temperature for 24 hrs. The exact incubation time for a specific prodrug was based on the prior aqueous stability data. If the compound was stable in the buffer up to 24 hrs, then the solubility was measured after 24 hrs, otherwise kinetic solubility data was reported. The final saturated solution was then transferred to a 1.5 mL Eppendorf tube and centrifuged for ~2 min. at 10000 rpms. The supernatant from the saturated solution was transferred to a glass HPLC vial and the solubility was analyzed by HPLC using a four point calibration curve.

TABLE 14

Solubility Data for Examples 1 to 22

| | Solubility (mg/mL) | |
|---|---|---|
| Example | pH 4.0 | pH 6.5 |
| 1 | 0.01 | >1.22 |
| 2 | 0.99 | 0.42 |
| 3 | >0.28 | >0.52 |
| 4 | >3.23 | >1.07 |
| 5 | 2.30 | 3.20 |
| 6 | 0.30 | 0.50 |
| 7 | 1.78 | 2.09 |
| 8 | 0.52 | >0.47 |
| 9 | 0.75 | 0.64 |
| 10 | >0.27 | <0.001 |
| 11 | >2.67 | >3.4 |
| 12 | 0.82 | 0.63 |
| 13 | >0.92 | 0.94 |
| 14 | 0.42 | 0.02 |
| 15 | 0.27 | >0.41 |
| 16 | 0.23 | 0.01 |
| 17 | 0.56 | >1.9 |
| 18 | 0.29 | >1.05 |
| 19 | 0.97 | >1.42 |
| 20 | 0.43 | 0.39 |
| 21 | 0.64 | 0.63 |
| 22 | >0.39 | 0.03 |

Solution Stability Assay

Acetonitrile Stock Solution: Acetonitrile Stock Solution of the prodrug was prepared by dissolving 1.5-2.0 mg of weighted compound in 5.0 mL of acetonitrile in a 5 mL volumetric flask.

pH 6.5 Buffer Working Solution: A pH 6.5 Buffer Working Solution of drug was prepared by adding 1.5 mL of the Acetonitrile Stock Solution to 3.5 mL of stability buffer (50 mM potassium phosphate, pH 6.5) in a 10 mL vial, and mixing. Using a 3 mL syringe, ~3 mL of solution was withdrawn and filtered using the Gelman 0.45 μm syringe filter into a clean 1.5 mL LC vial. This filtered solution will was used to evaluate the prodrug degradation throughout the course of the study. Target concentration: 90-120 μg/mL (70% Aqueous: 30% Acetonitrile)

pH 4.0 Acidic Working Solution: A pH 4.0 Working Solution of drug was prepared by adding 1.5 mL of the Acetonitrile Stock Solution to 3.5 mL of stability buffer (50 mM sodium acetate, pH 4.0) in a 10 mL vial and mixing. Using a 3 mL syringe, ~3 mL of solution was withdrawn and filtered using the Gelman 0.45 μm syringe filter into a clean 1.5 mL LC vial. This filtered solution was used to evaluate the prodrug degradation throughout the course of the study. Target concentration: 90-120 μg/mL (70% Aqueous: 30% Acetonitrile)

Experimental Methods: Following the sample preparation procedure described above a single sample (n=1) was prepared for each pH condition. The samples were then placed in an HPLC autosampler maintained at 37° C. and samples were analyzed over a 24 h period. Prodrug remaining (%) was reported relative to the initial peak area (t=0 h). In cases where a conversion to parent half-life could be calculated, a $t_{1/2}$ was generated. Confirmation of the conversion to parent from the prodrug was obtained by LCMS and HPLC analysis of the final timepoint samples.

Typical LC parameters are shown below:

HPLC System: HP1100 Series, Hewlett Packard., Heated autosampler

Analytical column: Synergi 4 u Hydro C18, 4.6 mm×5.0 cm, PHENOMENEX®

Column temperature: 40° C.

Autosampler temp: 37° C.

Flow rate: 1.0 mL/min

Injection Volume: 10 μL

Mobile Phase: A: Acetonitrile

B: 0.1% Phosphoric acid in water

Run Time: 14.0 minutes
Typical LCMS parameters are shown below:
LC-MS System: Surveyor HPLC system, ThermoFinnigan LCQ Deca XP Max (Ion trap)
Analytical column: Synergi 4 u Hydro C18, 4.6 mm×5.0 cm, PHENOMENEX®
Column temperature: 40° C.
Autosampler temp: 22° C.
Flow rate: 1.0 mL/min
Injection Volume: 5 μL
Mobile Phase: A: 95% Acetonitrile/5% 20 mM Ammonium Acetate
B: 5% Acetonitrile/95% 20 mM Ammonium Acetate
LCQ Parameters:
  Sheath Flow Rate: 81.64
  Aux/Sweep Flow Rate: 19.01
  Current (uA): 10.89
  Voltage (kV): 5.00
  Capillary (C): 348.10
  Capillary Voltage (V): 30.44

TABLE 15

Aqueous Stability Data for Examples 1 to 22

| Example | Stability ($t_{1/2}$, h) | |
|---|---|---|
| | pH 4.0 | pH 6.5 |
| 1 | >500 | >500 |
| 2 | >500 | >500 |
| 3 | >500 | >500 |
| 4 | 64 | 8 |
| 5 | 92 | 5 |
| 6 | >500 | 41 |
| 7 | >500 | >500 |
| 8 | >500 | 334 |
| 9 | 335 | 58 |
| 10 | NA | 32 |
| 11 | 215 | 29 |
| 12 | 376 | 251 |
| 13 | 334 | 108 |
| 14 | 73 | 44 |
| 15 | >500 | >500 |
| 16 | 250 | 16 |
| 17 | 250 | 300 |
| 18 | >500 | >500 |
| 19 | >500 | 56 |
| 20 | 97 | 15 |
| 21 | 334 | 376 |
| 22 | NA | 7 |

Prodrug Evaluation: Single-Dose Pharmacokinetics in Rats

Male Sprague-Dawley rats (250-300 g) were used for the pharmacokinetic studies. Rats were fasted overnight prior to dosing and fed 4 h post dose. In each study, groups of animals (N=2-3) received the test compound as an intravenous (IV) infusion (over 10 min) via the jugular vein. Blood samples (~0.3 mL) were collected from the jugular vein into $K_2$EDTA-containing tubes at 0.5, 1, 3, 5, 7, and 24 h post dose. Plasma samples, obtained by centrifugation at 4° C. (1500-2000×g), were stored at −20° C. until analysis by LC/MS/MS.

Data Analysis for Pharmacokinetic Assays

The pharmacokinetic parameters were obtained by non-compartmental analysis of plasma concentration (determined by LC/MS/MS) vs. time data (ThermoKinetica Software version 4.4.1). The peak concentration ($C_{max}$) and time for $C_{max}$, $T_{max}$, were recorded directly from experimental observations. The area under the curve from time zero to the last sampling time ($AUC_{0-t}$) was calculated using a combination of linear and log trapezoidal summations. The total plasma clearance (CLTp), steady-state volume of distribution (Vss), apparent elimination half-life ($t_{1/2}$) and mean residence time (MRT) were estimated after IV administration. Estimation of T½ was made using a minimum of 3 time points with quantifiable concentrations. The absolute oral bioavailability F was estimated as the ratio of dose-normalized AUC values following oral and IV doses. The plasma exposures of Compound A or Compound B ($AUC_{0-24h}$ or $AUC_{0-7}$h) after administration of the prodrugs were compared with the exposure after administration of parent Compound A or B. The relative bioavailabilities of the prodrugs to Compound A or B were estimated (Tables 16-17).

TABLE 16

Administration of Prodrug Example Compound to Rat: Blood Levels of Compound B

| Example | Dose (mg/kg) | $AUC_{0-24h}$ of Compound B after Administration of Prodrug (nM · hr) | % Relative Bioavailability to Compound B |
|---|---|---|---|
| 1 | 2.8 | 2919 | 47 |
| 6 | 0.6 | 569* | 94 |
| 9 | 3.0 | 7266 | 118 |

*$AUC_{0-7h}$

TABLE 17

Administration of Prodrug Example Compound to Rat: Blood Levels of Compound A

| Example | Dose (mg/kg) | AUC0-24 h of Compound A after Administration of Prodrug (nM · hr) | % Relative Bioavailability to Compound A |
|---|---|---|---|
| 11 | 1.3 | 686 | 81 |
| 12 | 1.4 | 743 | 88 |

Example 12 and Compound A were evaluated for in vivo efficacy against TALL1 Human T-cell acute lymphoblastic leukemia. Example 12 is a prodrug of Compound A. As illustrated in FIG. 1, Compound A and Example 12 were active as defined by the tumor growth inhibition (TGI).

What is claimed is:

1. A compound of Formula (I):

(I)

[Chemical structure of Formula (I)]

wherein:
a) $R_1$ is H or —$CH_3$, and $R_2$ is $R_y$; or
b) $R_1$ is $R_x$ and $R_2$ is H;
$R_x$ is: —$CH_2OC(O)$—$(CH_2)_n$—$(CR_aR_b)_n$—X;
X is —$NR_eR_f$, —$OP(=O)(OH)_2$,

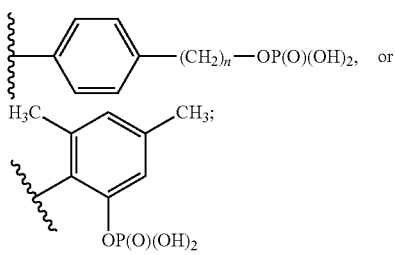 or

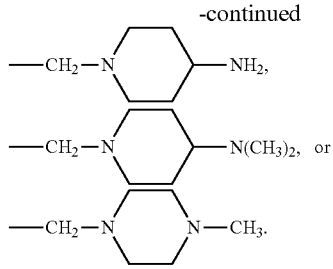

$R_a$ and $R_b$ are independently H and/or $C_{1-3}$ alkyl, or together with the carbon atom to which they are attached form a $C_{3-5}$ cycloalkyl ring;
each n is independently zero and/or 1;
$R_y$ is Z or —S—Z;
Z is $C_{1-6}$ alkyl substituted with —$NR_cR_d$ and/or —$CO_2R_g$;
$R_c$ and $R_d$ are independently H and/or $C_{1-4}$ alkyl, or together with the nitrogen to which they are attached form a heterocycle containing 1 to 2 nitrogen atoms, wherein said heterocycle is substituted with zero to 2 substituents independently selected from —OH, $C_{1-4}$ alkyl, and/or $NR_eR_f$;
$R_e$ and $R_f$ are independently H and/or $C_{1-4}$ alkyl; and
$R_g$ is H or $C_{1-4}$ alkyl;
or a salt thereof.

2. A compound according to claim 1 or a salt thereof, wherein:
$R_x$ is: —$CH_2OC(O)C(CH_3)_2NH_2$, —$CH_2OC(O)CH(CH_3)NH_2$, —$CH_2OC(O)CH(CH(CH_3)_2)NH_2$,

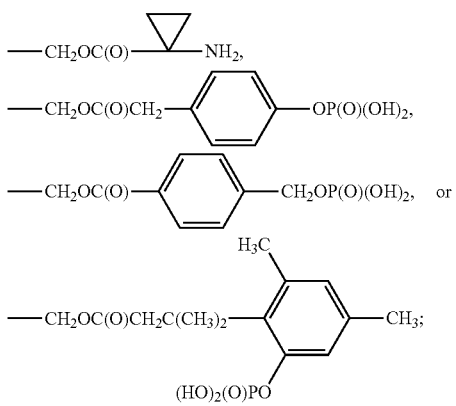

and
$R_y$ is: —$SCH_2CH_2NH_2$, —$SCH_2CH_2N(CH_3)_2$, —$SCH_2CH(NH_2)C(O)OH$, —$SCH_2CH(NH_2)C(O)OCH_3$, —$CH_2NHCH_2CH(CH_3)_2$,

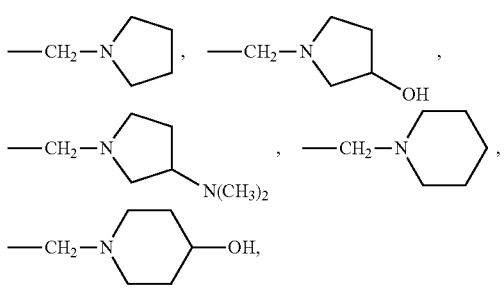

-continued

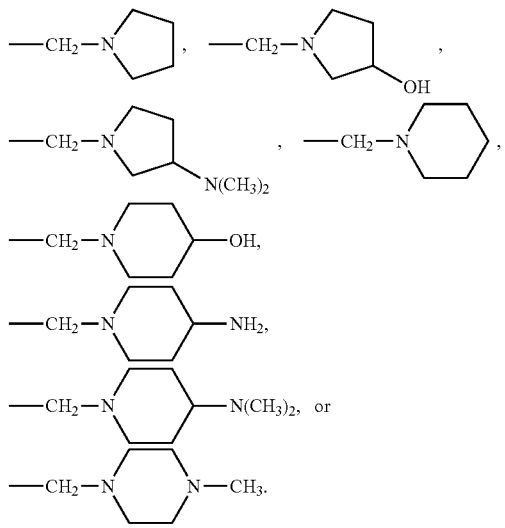

3. The compound according to claim 2 or a salt thereof, wherein $R_1$ is H and $R_2$ is $R_y$.

4. The compound according to claim 3 or a salt thereof, wherein $R_y$ is —$SCH_2CH_2NH_2$, —$SCH_2CH(NH_2)C(O)OH$, or

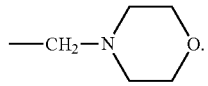

5. The compound according to claim 2 or a salt thereof, wherein $R_1$ is —$CH_3$ and $R_2$ is $R_y$.

6. The compound according to claim 5 or a salt thereof, wherein $R_y$ is —$CH_2NHCH_2CH(CH_3)_2$, —$SCH_2CH_2NH_2$, —$SCH_2CH_2N(CH_3)_2$, —$SCH_2CH(NH_2)C(O)OH$, —$SCH_2CH(NH_2)C(O)OCH_3$, 7. The compound according to claim 5 or a salt thereof, wherein $R_1$ is $R_x$ and $R_2$ is H.

8. The compound according the claim 1 selected from: ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl (4-(phosphonooxy)phenyl)acetate (1); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl 4-((phosphonooxy)methyl)benzoate (2); (3-(((2R,3S)-3-carbamoyl-6,6,6-trifluoro-2-(3,3,3-trifluoropropyl)hexanoyl) amino)-2-oxo-5-phenyl-2,3-dihydro-1H-1,4-benzodiazepin-1-yl)methyl 3-(2,4-dimethyl-6-(phosphonooxy)phenyl)-3-methylbutanoate (3); ((3S)-3-(((2R,3S)-3-carbamoyl-6,6,6- trifluoro-2-(3,3,3-trifluoropropyl)hexanoyl)amino)-2-oxo-5-phenyl-2,3-dihydro-1H-1,4-benzodiazepin-1-yl)methyl 2-methylalaninate (4); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl L-alaninate (5); ((3S)-3-(((2R,3S)-3-carbamoyl-6,6,6-trifluoro-2-(3,3,3-trifluoropropyl)hexanoyl)amino)-2-oxo-5-phenyl-2,3-dihydro-1H-1,4-benzodiazepin-1-yl)methyl L-valinate (6); ((3S)-3-(((2R,3S)-3-carbamoyl-6,6,6-trifluoro-2-(3,3,3-trifluoropropyl) hexanoyl)amino)-2-oxo-5-phenyl-2,3-dihydro-1H-1,4-benzodiazepin-1-yl)methyl 1-aminocyclopropanecarboxylate (7); (2S,3R)—N-((2-aminoethyl)sulfanyl)-N'-((3S)-2-oxo-5-phenyl-2,3-dihydro-1H-1,4-benzodiazepin-3-yl)-2,3-bis(3,3,3-trifluoropropyl)succinamide (8); S-(((2S,3R)-6,6,6-trifluoro-3-(((3S)-2-oxo-5-phenyl-2,3-dihydro-1H-1,4-benzodiazepin-3-yl)carbamoyl)-2-(3,3,3-trifluoropropyl)hexanoyl)amino)-L-cysteine (9); (2S,3R)—N-((isobutylamino)methyl)-N'-((3S)-1-methyl-2-oxo-5-phenyl-2,3-dihydro-1H-1,4-benzodiazepin-3-yl)-2,3-bis(3,3,3-trifluoropropyl) succinamide (10); (2S,3R)—N-((2-aminoethyl)sulfanyl)-N'-((3S)-1-methyl-2-oxo-5-phenyl-2,3-dihydro-1H-1,4-benzodiazepin-3-yl)-2,3-bis(3,3,3-trifluoropropyl) succinamide (11); S-(((2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoyl)amino)-L-cysteine (12); (2S,3R)—N-((2-(dimethylamino)ethyl)sulfanyl)-N'-((3S)-1-methyl-2-oxo-5-phenyl-2,3-dihydro-1H-1,4-benzodiazepin-3-yl)-2,3-bis(3,3,3-trifluoropropyl) succinamide (13); Methyl S-(((2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoyl)amino)-L-cysteinate (14); (2R,3S)—N-((3S)-1-methyl-2-oxo-5-phenyl-2,3-dihydro-1H-1,4-benzodiazepin-3-yl)-N'-((4-methyl-1-piperazinyl)methyl)-2,3-bis(3,3,3-trifluoropropyl)succinamide (15); (2R,3S)—N-((3S)-1-methyl-2-oxo-5-phenyl-2,3-dihydro-1H-1,4-benzodiazepin-3-yl)-N'-(1-piperidinylmethyl)-2,3-bis(3,3,3-trifluoropropyl)succinamide (16); (2S,3R)—N-((4-amino-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (17); (2S,3R)—N-((4-(dimethylamino)-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (18); (2S,3R)—N-((4-hydroxy-1-piperidinyl)methyl)-N'-((3S)-1-methyl-2-oxo-5-phenyl-2,3-dihydro-1H-1,4-benzodiazepin-3-yl)-2,3-bis(3,3,3-trifluoropropyl)succinamide (19); (2S,3R)—N-((3-hydroxy-1-pyrrolidinyl)methyl)-N'-((3S)-1-methyl-2-oxo-5-phenyl-2,3-dihydro-1H-1,4-benzodiazepin-3-yl)-2,3-bis(3,3,3-trifluoropropyl) succinamide (20); (2S,3R)—N-((3-(dimethylamino)-1-pyrrolidinyl)methyl)-N'-((3S)-1-methyl-2-oxo-5-phenyl-2,3-dihydro-1H-1,4-benzodiazepin-3-yl)-2,3-bis(3,3,3-trifluoropropyl) succinamide (21); (2R,3S)—N-((3S)-1-methyl-2-oxo-5-phenyl-2,3-dihydro-1H-1,4-benzodiazepin-3-yl)-N'-(1-pyrrolidinylmethyl)-2,3-bis(3,3,3-trifluoropropyl)succinamide (22); and salts thereof.

9. A pharmaceutical composition comprising a compound according to claim 1 or a pharmaceutically acceptable salt thereof; and a pharmaceutically acceptable carrier.

* * * * *